United States Patent
Kim et al.

(10) Patent No.: US 10,121,976 B2
(45) Date of Patent: Nov. 6, 2018

(54) ORGANOMETALLIC COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Sung-Wook Kim, Yongin (KR); Myeong-Suk Kim, Yongin (KR); Hwan-Hee Cho, Yongin (KR)

(73) Assignee: SAMSUNG DISPLAY CO., LTD., Yongin, Gyeonggi-do (KR)

( * ) Notice: Subject to any disclaimer, the term of this patent is extended or adjusted under 35 U.S.C. 154(b) by 452 days.

(21) Appl. No.: 14/740,807

(22) Filed: Jun. 16, 2015

(65) Prior Publication Data

US 2016/0190483 A1 Jun. 30, 2016

(30) Foreign Application Priority Data

Dec. 30, 2014 (KR) .................. 10-2014-0194319

(51) Int. Cl.
 *H01L 51/00* (2006.01)
 *C07F 15/00* (2006.01)
 *H01L 51/50* (2006.01)

(52) U.S. Cl.
 CPC ...... *H01L 51/0085* (2013.01); *C07F 15/0033* (2013.01); *H01L 51/0094* (2013.01);
 (Continued)

(58) Field of Classification Search
 None
 See application file for complete search history.

(56) References Cited

U.S. PATENT DOCUMENTS

2007/0172698 A1* 7/2007 Iwakuma .......... C09K 11/06 428/690
2008/0001530 A1* 1/2008 Ise .................. C09K 11/06 313/504

(Continued)

FOREIGN PATENT DOCUMENTS

JP 2013-147497 A 8/2013
KR 10-2007-0090953 A 9/2007

(Continued)

OTHER PUBLICATIONS

Ho, et al., "Small-molecular blue phosphorescent dyes for organic light-emitting devices;" New J. Chem. vol. 37 pp. 1665-1683 (2013).

*Primary Examiner* — Kevin M Bernatz
(74) *Attorney, Agent, or Firm* — Lee & Morse, P.C.

(57) ABSTRACT

An organometallic compound and an organic light-emitting device, the organometallic compound being represented by the following Formula 1:

$$M(L_1)_{n1}(L_2)_{n2} \qquad \text{<Formula 1>}$$

wherein in Formula 1, M is selected from iridium (Ir), platinum (Pt), osmium (Os), titanium (Ti), zirconium (Zr), hafnium (Hf), europium (Eu), terbium (Tb), thulium (Tm), and rhodium (Rh); n1 is 0, 1, 2, or 4; n2 is 1, 2, or 3; when n1 is two or more, two or more $L_1$ are identical or different, and when n2 is two or more, two or more $L_2$ are identical to different; $L_1$ is selected from a monovalent organic ligand, a divalent organic ligand, a trivalent organic ligand, and a tetravalent organic ligand, and is different from $L_2$; $L_2$ is a ligand represented by the following Formula 2;

(Continued)

<Formula 2>

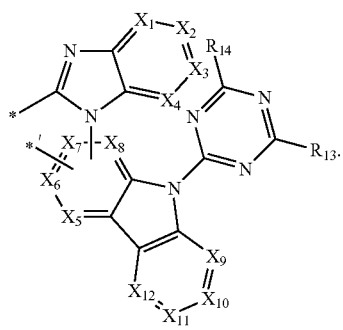

14 Claims, 1 Drawing Sheet

(52) U.S. Cl.
CPC ...... *H01L 51/0058* (2013.01); *H01L 51/0072* (2013.01); *H01L 51/5016* (2013.01)

(56) References Cited

U.S. PATENT DOCUMENTS

| | | | |
|---|---|---|---|
| 2008/0018221 A1 | 1/2008 | Egen et al. | |
| 2012/0326103 A1* | 12/2012 | Mak | C07F 15/0033 252/582 |
| 2013/0181190 A1* | 7/2013 | Ma | C07F 15/0033 257/40 |
| 2013/0306940 A1* | 11/2013 | Zeng | H01L 51/0085 257/40 |
| 2014/0110691 A1* | 4/2014 | Lin | C07F 15/0033 257/40 |
| 2014/0167001 A1* | 6/2014 | Lee | C09K 11/06 257/40 |
| 2015/0034927 A1* | 2/2015 | Nakano | C07F 9/65517 257/40 |
| 2015/0207084 A1* | 7/2015 | Hwang | H01L 51/0085 257/40 |
| 2015/0333278 A1* | 11/2015 | Kim | C07F 15/0033 257/40 |

FOREIGN PATENT DOCUMENTS

| | | |
|---|---|---|
| KR | 10-2013-0042865 A | 4/2013 |
| KR | 10-2013-0131230 A | 12/2013 |
| KR | 10-2014-0041552 A | 4/2014 |

* cited by examiner

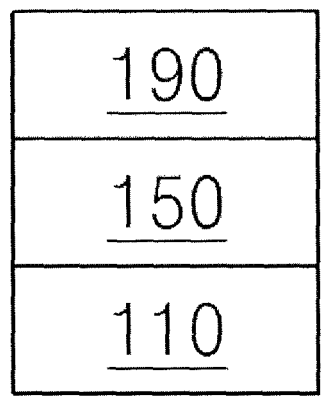

ORGANOMETALLIC COMPOUND AND ORGANIC LIGHT-EMITTING DEVICE INCLUDING THE SAME

CROSS-REFERENCE TO RELATED APPLICATION

Korean Patent Application No. 10-2014-0194319, filed on Dec. 30, 2014, in the Korean Intellectual Property Office, and entitled: "Organometallic Compound and Organic Light-Emitting Device Including The Same," is incorporated by reference herein in its entirety.

BACKGROUND

1. Field

Embodiments relate to an organometallic compound and an organic light-emitting device including the same.

2. Description of the Related Art

Organic light emitting devices are self-emission devices that have wide viewing angles, high contrast ratios, short response times, and excellent brightness, driving voltage, and response speed characteristics, and produce full-color images.

The organic light-emitting device may include a first electrode disposed on a substrate, and a hole transport region, an emission layer, an electron transport region, and a second electrode, which are sequentially disposed on the first electrode. Holes provided from the first electrode may move toward the emission layer through the hole transport region, and electrons provided from the second electrode may move toward the emission layer through the electron transport region. Carriers, such as holes and electrons, are recombined in the emission layer to produce excitons. These excitons change from an excited state to a ground state, thereby generating light.

SUMMARY

Embodiments are directed to an organometallic compound and an organic light-emitting device including the same.

An aspect provides an organometallic compound represented by Formula 1 below:

$$M(L_1)_{n1}(L_2)_{n2} \quad \text{<Formula 1>}$$

wherein in Formula 1,

M is selected from iridium (Ir), platinum (Pt), osmium (Os), titanium (Ti), zirconium (Zr), hafnium (Hf), europium (Eu), terbium (Tb), thulium (Tm), and rhodium (Rh);

$L_1$ is selected from a monovalent organic ligand, a divalent organic ligand, a trivalent organic ligand, and a tetravalent organic ligand, and is different from $L_2$;

$L_2$ is selected from a ligand represented by Formula 2;

n1 is 0, 1, 2, or 4;

n2 is 1, 2, or 3;

when n1 is two or more, two or more $L_1$ are identical or different, and when n2 is two or more, two or more $L_2$ are identical to different:

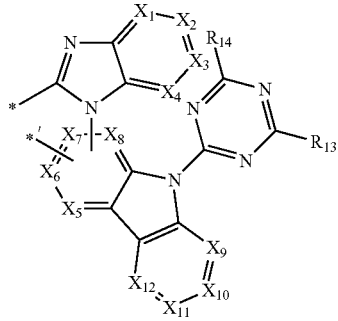
<Formula 2> wherein in Formula 2, $X_1$ is N (nitrogen) or $C(R_1)$, $X_2$ is N or $C(R_2)$, $X_3$ is N or $C(R_3)$, and $X_4$ is N or $C(R_4)$;

$X_5$ is N, C (carbon), or $C(R_5)$, $X_6$ is N, C, or $C(R_6)$, $X_7$ is N, C, or $C(R_7)$, $X_8$ is N, C, or $C(R_8)$, two selected from $X_5$ to $X_8$ are C, when $X_5$ is C, $X_5$ binds to M or N of a benzimidazole-based ring in Formula 1; when $X_6$ is C, $X_6$ binds to M or N of the benzimidazole-based ring in Formula 1; when $X_7$ is C, $X_7$ binds to M or N of a benzimidazole-based ring in Formula 1; when $X_8$ is C, $X_8$ binds to M or N of a benzimidazole-based ring in Formula 1;

$X_9$ is N or $C(R_9)$, $X_{10}$ is N or $C(R_{10})$, $X_{11}$ is N or $C(R_{11})$, $X_{12}$ is N or $C(R_{12})$;

$R_1$ to $R_{14}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —$N(Q_1)(Q_2)$, —$Si(Q_3)(Q_4)(Q_5)$, —$B(Q_6)(Q_7)$, and —$C(=O)(Q_8)$;

two selected from $R_1$ to $R_4$ may optionally bind to each other to form a saturated or unsaturated ring, two selected from $R_9$ to $R_{12}$ may optionally bind to each other to form a saturated or unsaturated ring. $R_{13}$ and $R_{14}$ may optionally bind to each other to form a saturated or unsaturated ring:

* and *' each indicate a binding site to M in Formula 1;

at least one substituent of the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arythio group, the substituted $C_1$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —C(=O)($Q_{18}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic heterocondensed polycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —C(=O)($Q_{28}$); and —N($Q_{31}$)($Q_{32}$), —Si($Q_{33}$)($Q_{34}$)($Q_{35}$), —B($Q_{36}$)($Q_{37}$), and —C(=O)($Q_{38}$);

wherein $Q_1$ to $Q_8$, $Q_{11}$ to $Q_{18}$, $Q_{21}$ to $Q_{28}$, and $Q_{31}$ to $Q_{38}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arythio group, a $C_1$-$C_{60}$ heteroaryl group, a monovalent non-aromatic condensed polycyclic group, and a monovalent non-aromatic condensed heteropolycyclic group.

Another aspect provides an organic light-emitting device including: a first electrode; a second electrode facing the first electrode; and an organic layer that is disposed between the first electrode and the second electrode and includes an emission layer, wherein the organic layer includes at least one organometallic compound represented by Formula 1.

BRIEF DESCRIPTION OF THE DRAWING

Features will be apparent to those of skill in the art by describing in detail exemplary embodiments with reference to the attached drawing in which:

FIG. 1 illustrates a schematic view of an organic light-emitting device according to an embodiment.

DETAILED DESCRIPTION

Example embodiments will now be described more fully hereinafter with reference to the accompanying drawing; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing FIGURE, the dimensions of layers and regions may be exaggerated for clarity of illustration. Like reference numerals refer to like elements throughout.

An organometallic compound according to an embodiment may be represented by Formula 1 below.

$$M(L_1)_{n1}(L_2)_{n2} \qquad \text{<Formula 1>}$$

In Formula 1, M may be selected from, e.g., iridium (Ir), platinum (Pt), osmium (Os), titanium (Ti), zirconium (Zr), hafnium (Hf), europium (Eu), terbium (Tb), thulium (Tm), and rhodium (Rh).

In Formula 1, $L_1$ may be selected from, e.g., a monovalent organic ligand, a divalent organic ligand, a trivalent organic ligand, and a tetravalent organic ligand. $L_2$ may be, e.g., a ligand represented by the following Formula 2. $L_1$ may be different from $L_2$.

In Formula 1, n1 may be 0, 1, 2, or 4, and n2 may be 1, 2, or 3.

In an implementation, when M is iridium (Ir), n1 may be 0, 1 or 2, n2 may be 1, 2 or 3, and a sum of n1 and n2 may be 3. In an implementation, when M is platinum (Pt), n1 may be 0, 1, or 2, n2 may be 1 or 2, and the sum of n1 and n2 may be 2.

n1 in Formula 1 indicates the number of $L_1$, and may be 0, 1, 2, or 4. When n1 is 2 or more, 2 or more $L_1$ may be identical or different.

n2 in Formula 1 indicates the number of $L_2$, and may be 1, 2, or 3. When n2 is 2 or more, 2 or more $L_2$ may be identical or different.

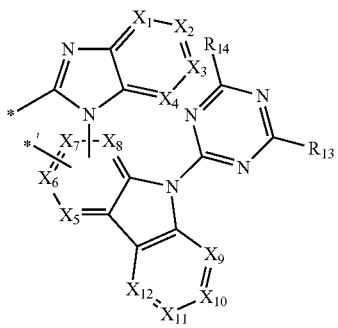

<Formula 2>

In Formula 2, $X_1$ may be N (nitrogen) or $C(R_1)$, $X_2$ may be N or $C(R_2)$, $X_3$ may be N or $C(R_3)$, and $X_4$ may be N or $C(R_4)$. $R_1$ to $R_4$ are described below.

In an implementation, $X_1$ may be $C(R_1)$, $X_2$ may be $C(R_2)$, $X_3$ may be $C(R_3)$, and $X_4$ may be $C(R_4)$.

In Formula 2, $X_5$ may be N, C (carbon), or $C(R_5)$, $X_6$ may be N, C, or $C(R_6)$, may be N, C, or $C(R_7)$, $X_8$ may be N, C, or $C(R_8)$, and two selected from $X_5$ to $X_8$ may be C. $R_5$ to $R_8$ are described below.

In an implementation, when $X_5$ is C, $X_5$ may bind to M or N of the benzimidazole-based moiety in Formula 1 (e.g., of Formula 2); when $X_6$ is C, $X_6$ may bind to M or N of the benzimidazole-based moiety in Formula 2; when $X_7$ is C, $X_7$ may bind to M or N of the benzimidazole-based moiety in Formula 2; or when $X_8$ is C, $X_8$ may bind to M or N of the benzimidazole-based moiety in Formula 2.

In an implementation, $X_5$ and $X_6$ may be C; $X_6$ and $X_7$ may be C; or $X_7$ and $X_8$ may be C.

In Formula 2, $X_9$ may be N or $C(R_9)$, $X_{10}$ may be N or $C(R_{10})$, $X_{11}$ may be N or $C(R_{11})$, and $X_{12}$ may be N or $C(R_{12})$. $R_9$ to $R_{12}$ are described below.

In an implementation, $X_9$ may be $C(R_9)$, $X_{10}$ may be $C(R_{10})$, $X_{11}$ may be $C(R_{11})$, and/or $X_{12}$ may be $C(R_{12})$.

$R_1$ to $R_{14}$ may each independently be selected from or include, e.g., a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic heterocondensed polycyclic group, —$N(Q_1)(Q_2)$, —$Si(Q_3)(Q_4)(Q_5)$, —$B(Q_6)(Q_7)$, and —$C(=O)(Q_8)$. $Q_1$ to $Q_8$ are described below.

In an implementation, $R_1$ to $R_{12}$ in Formula 2 may each independently be selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and —Si($Q_{33}$)($Q_{34}$)($Q_{35}$); and
—Si($Q_3$)($Q_4$)($Q_5$), wherein $Q_3$ to $Q_5$ and $Q_{33}$ to $Q_{35}$ may each independently be selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

In an implementation, $R_1$ to $R_{12}$ in Formula 2 may each independently be selected from:

a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group;

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group, each substituted with at least one selected from —F, a cyano group, a nitro group, a phenyl group, a naphthyl group, a pyridinyl group, a pyrimidinyl group, a triazinyl group, and —Si($Q_{33}$)($Q_{34}$)($Q_{35}$); and
—Si($Q_3$)($Q_4$)($Q_5$), wherein $Q_3$ to $Q_5$ and $Q_{33}$ to $Q_{35}$ may each independently be selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

In an implementation, $R_1$ to $R_4$ may be separate or two of $R_1$ to $R_4$ may bind to each other to form a saturated or unsaturated ring and/or $R_9$ to $R_{12}$ may be separate or two of $R_9$ to $R_{12}$ may bind to each other to form a saturated or unsaturated ring.

In an implementation, $R_{13}$ and $R_{14}$ in Formula 2 may each independently be selected from:

a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, and a pentoxy group;

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, and a pentoxy group, each substituted with at least one selected from —F, a cyano group, a nitro group, a phenyl group, a naphthyl group, a pyridinyl group, a pyrimidinyl group, and a triazinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, or an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and —Si($Q_{33}$)($Q_{34}$)($Q_{35}$); and —Si($Q_3$)($Q_4$)($Q_5$), wherein $Q_3$ to $Q_5$ and $Q_{33}$ to $Q_{35}$ may be each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

In an implementation, $R_{13}$ and $R_{14}$ in Formula 2 may each independently be selected from:

a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, and a pentoxy group;

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, and a pentoxy group, each substituted with at least one selected from —F, a cyano group, a nitro group, a phenyl group, a naphthyl group, a pyridinyl group, a pyrimidinyl group, and a triazinyl group;

a phenyl group, a naphthyl group, an anthracenyl group, a triphenylenyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, an imidazopyridinyl group, and an imidazopyrimidinyl group; and a phenyl group, a naphthyl group, an anthracenyl group, a triphenylenyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an anthracenyl group, a triphenylenyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, an imidazopyridinyl group, and an imidazopyrimidinyl group.

In an implementation, $R_{13}$ and $R_{14}$ in Formula 2 may each independently be a hydrogen or a phenyl group.

In an implementation, $R_{13}$ and $R_{14}$ may be separate or $R_{13}$ and $R_{14}$ may bind to each other to form a saturated or unsaturated ring.

* and *' in Formula 2 are binding sites to M in Formula 1.

In an implementation, $L_2$ in Formula 1 may be a ligand represented by one of the following Formulae 2A to 2F.

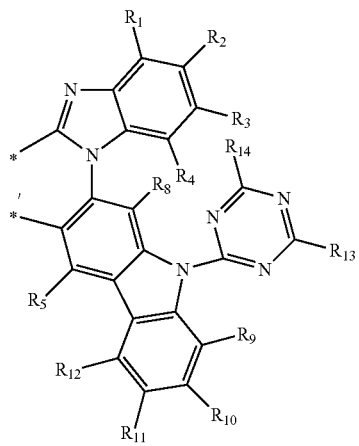

<Formula 2A>

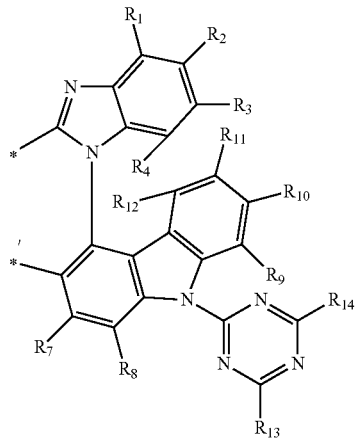

<Formula 2B>

<Formula 2C>

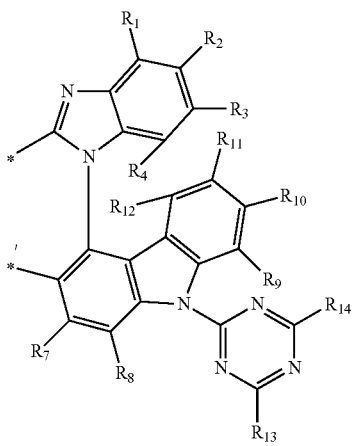

<Formula 2D>

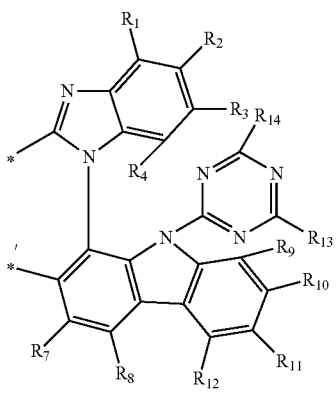

<Formula 2E>

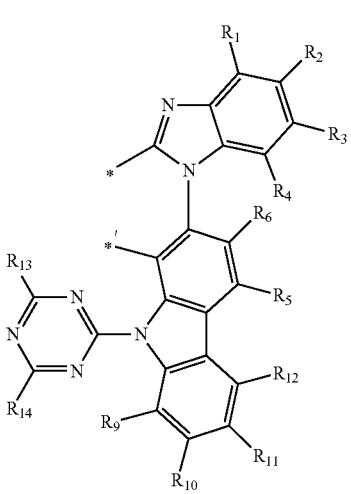

<Formula 2F>

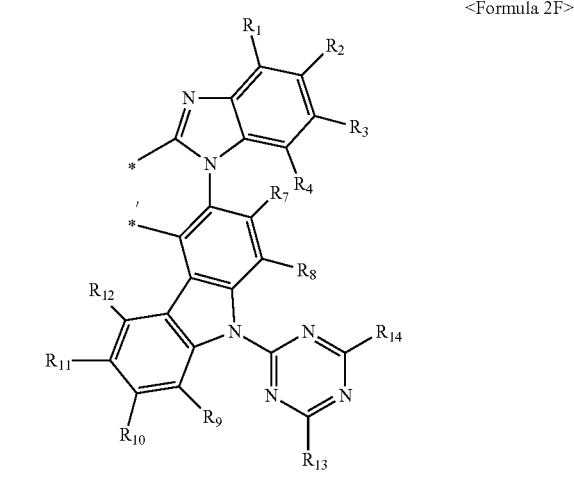

$R_1$ to $R_{14}$, *, and *' in Formulae 2A to 2F may be the same as defined above with respect to Formula 2.

In an implementation, $L_1$ in Formula 1 may be a ligand represented by the following Formula 3.

<Formula 3>

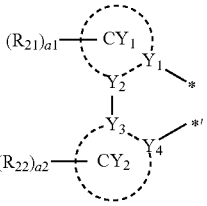

$Y_1$ to $Y_4$ in Formula 3 may each independently be carbon (C) or nitrogen (N).

In an implementation, in Formula 3, $Y_1$ may be C and $Y_4$ may be N.

In an implementation, in Formula 3, $Y_2$ and $Y_3$ may be C.

$Y_1$ and $Y_2$ in Formula 3 may be linked to each other via a single bond or a double bond, and $Y_3$ and $Y_4$ may be linked to each other via a single bond or a double bond.

$CY_1$ and $CY_2$ in Formula 3 may each independently be or form a $C_5$-$C_{60}$ cyclic group or a $C_1$-$C_{60}$ heterocyclic group. For example, $CY_1$ includes $Y_1$ and $Y_2$ to form a $C_5$-$C_{60}$ cyclic group or a $C_1$-$C_{60}$ heterocyclic group, and $CY_2$ includes $Y_3$ and $Y_4$ to form a $C_5$-$C_{60}$ cyclic group or a $C_1$-$C_{60}$ heterocyclic group.

$R_{21}$ and $R_{22}$ in Formula 3 may each independently be selected from or include, e.g., a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic heterocondensed polycyclic group, —N($Q_1$)($Q_2$), —Si($Q_3$)($Q_4$)($Q_5$), and B($Q_6$)($Q_7$). $Q_1$ to $Q_7$ are described below.

In an implementation, $CY_1$ and $CY_2$ may each independently be selected from or form (e.g., with $Y_1$ to $Y_4$) benzene group, a naphthalene group, a fluorene group, a spirofluorene group, an indene group, a pyrrol group, a thiophene group, a furan group, a imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzoimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and/or a dibenzothiophene group.

In an implementation, $R_{21}$ and $R_{22}$ may each independently be selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —SF$_5$, a $C_1$-$C_{20}$ alkyl group, and a $C_1$-$C_{20}$ alkoxy group;

a $C_1$-$C_{20}$ alkyl group and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and —Si($Q_{41}$)($Q_{42}$)($Q_{43}$), each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group;

$Q_{41}$ to $Q_{43}$ may be each independently selected from a hydrogen, a $C_1$-$C_{10}$ alkyl group, a $C_1$-$C_{10}$ alkoxy group, a phenyl group, a naphthyl group, a pyridinyl group, a pyrimidinyl group, and a triazinyl group.

In an implementation, $CY_1$ may be or form, e.g., a benzene group, a pyridine group, a pyrimidine group, or a triazine group, and $CY_2$ may be or form, e.g., a pyridine group, an imidazole group, a pyrazole group, a triazole group, or a tetrazole group.

In an implementation, $R_{21}$ and $R_{22}$ may each independently be selected from:

a hydrogen, —F, a cyano group, a nitro group. —SF$_5$, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group; and a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group and a dibenzothiophenyl group, each substituted with at least one selected from —F, a cyano group and a nitro group.

a1 and a2 in Formula 3 may each independently be an integer selected from 1, 2, 3, 4, and 5. For example, a1 and a2 may each independently be 0, 1, 2, or 3.

a1 in Formula 3 indicates the number of $R_{21}$, and when a1 is 2 or more, two or more $R_{21}$ may be identical or different.

a2 in Formula 3 indicates the number of $R_{22}$, and when a2 is 2 or more, two or more $R_{22}$ may be identical or different.

\* and \*' in Formula 3 are binding sites to M in Formula 1.

In an implementation, $L_1$ in Formula 1 may be a ligand represented by one of the following Formulae 3-1 to 3-24.

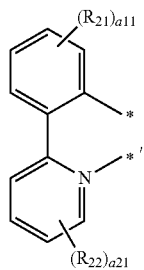

Formula 3-1

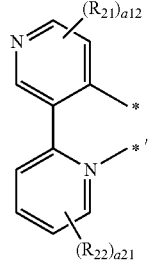

Formula 3-2

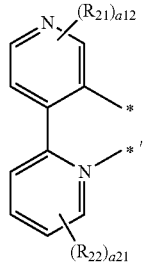

Formula 3-3

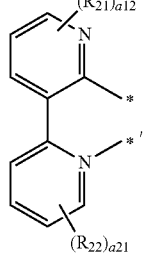

Formula 3-4

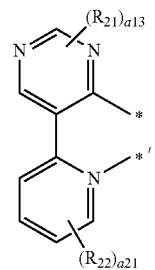

Formula 3-5

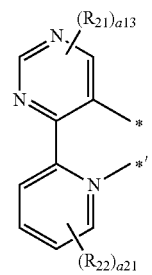

Formula 3-6

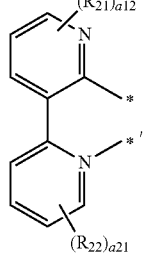

Formula 3-7

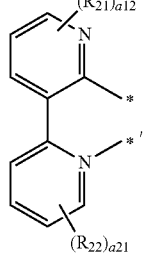

Formula 3-8

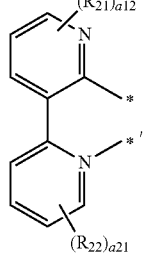

Formula 3-9

-continued
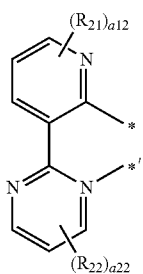
Formula 3-10
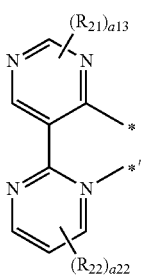
Formula 3-11
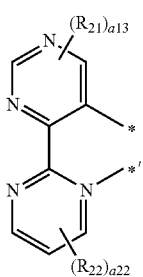
Formula 3-12
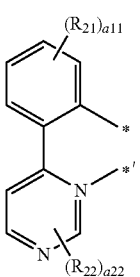
Formula 3-13
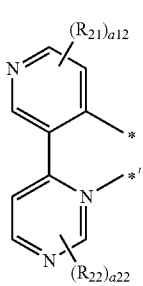
Formula 3-14
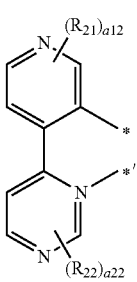
Formula 3-15
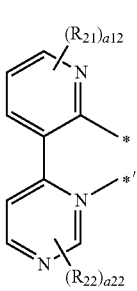
Formula 3-16
Formula 3-17
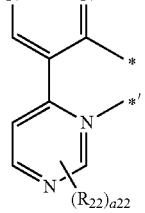
Formula 3-18
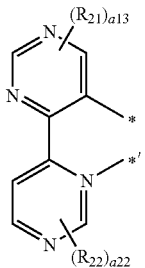
Formula 3-19
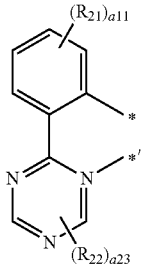

-continued

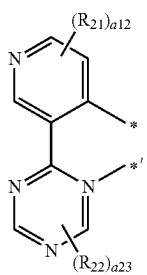
Formula 3-20

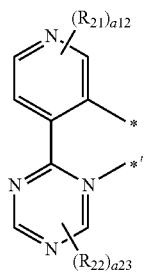
Formula 3-21

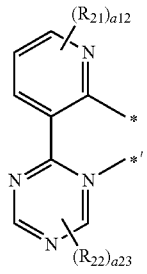
Formula 3-22

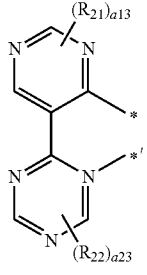
Formula 3-23

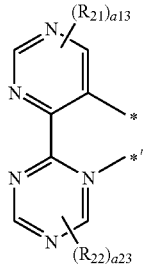
Formula 3-24

In Formulae 3-1 to 3-24, $R_{21}$ and $R_{22}$ may each independently be selected from:

a hydrogen, —F, a cyano group, a nitro group, —$SF_5$, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group; and a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group and a dibenzothiophenyl group, each substituted with at least one selected from —F, a cyano group and a nitro group;

a11 and a21 may each independently be 1, 2, 3, or 4; a12 and a22 may each independently be 1, 2, or 3, a13 and a23 may each independently be 1 or 2;

* and *' each indicate a binding site to M in Formula 1.

In an implementation, $L_1$ may be a ligand represented by one of the following Formulae 4-1 to 4-4.

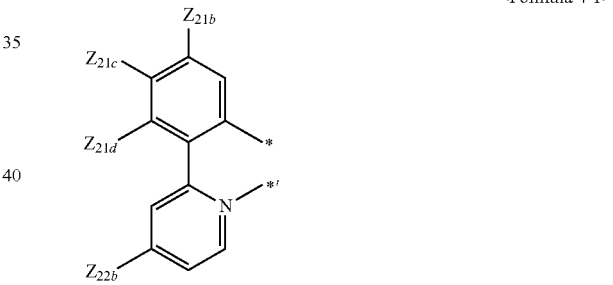
<Formula 4-1>

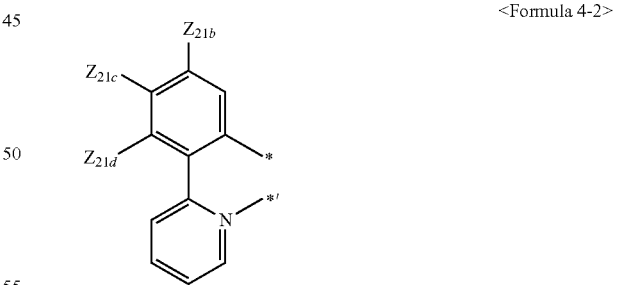
<Formula 4-2>

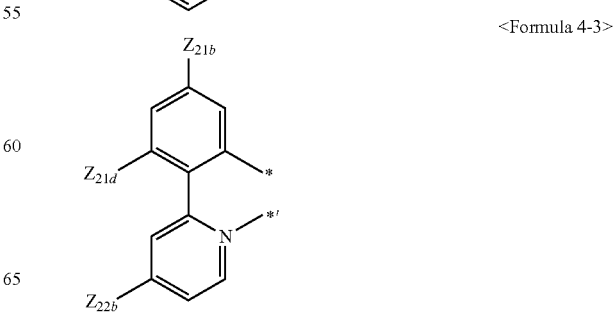
<Formula 4-3>

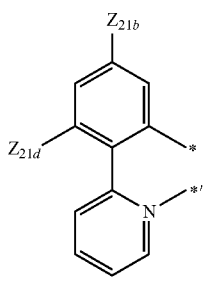

<Formula 4-4>

In Formulae 4-1 to 4-4, $Z_{21b}$, $Z_{21c}$, $Z_{21d}$, and $Z_{22b}$ may each independently be selected from:

—F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group;

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group, each substituted with at least one selected from —F, a cyano group, a nitro group, a phenyl group, a pyridinyl group, a pyrimidinyl group, a triazinyl group, and —Si$(Q_{33})(Q_{34})(Q_{35})$; and —Si$(Q_3)(Q_4)(Q_5)$;

wherein $Q_3$ to $Q_5$ and $Q_{33}$ to $Q_{35}$ may each independently be selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

For example, $Z_{21b}$, $Z_{21c}$, and $Z_{21d}$ may each independently be selected from —F, —Cl, —CN and —NO$_2$; and a $C_1$-$C_{20}$ alkyl group and a $C_1$-$C_{20}$ alkoxy group, each substituted with at least one selected from —F, —Cl, —CN, and —NO$_2$.

$Z_{22b}$ may be selected from a $C_1$-$C_{20}$ alkyl group and —N$(Q_{41})(Q_{42})$, and $Q_{41}$ and $Q_{42}$ may each independently be selected from a hydrogen, a $C_1$-$C_{20}$ alkyl group, a phenyl group, a naphthyl group, and an anthracenyl group.

In an implementation, the organometallic compound represented by Formula 1 may be represented by one of the following Formulae 1-1 to 1-24.

<Formula 1-1>

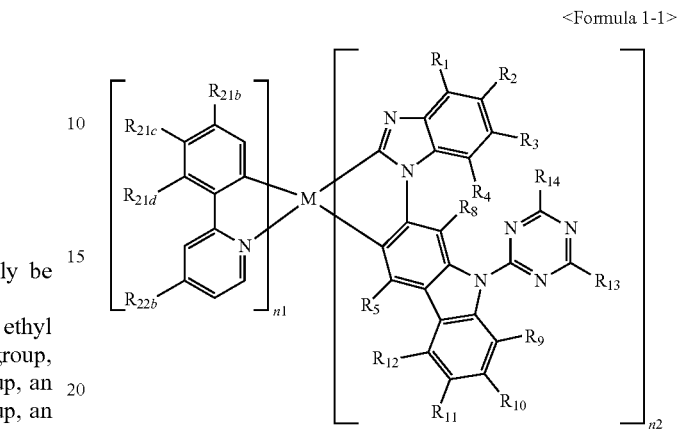

<Formula 1-2>

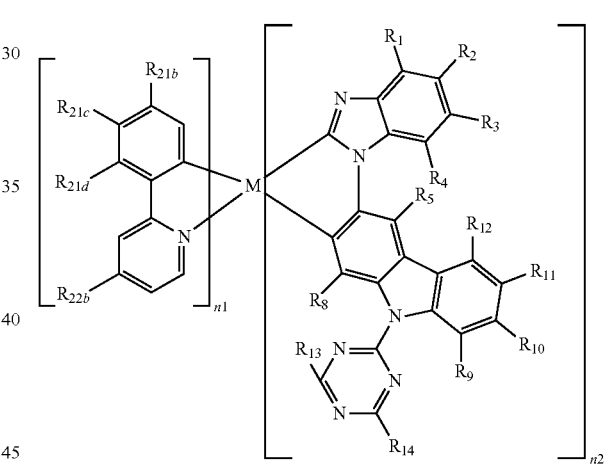

<Formula 1-3>

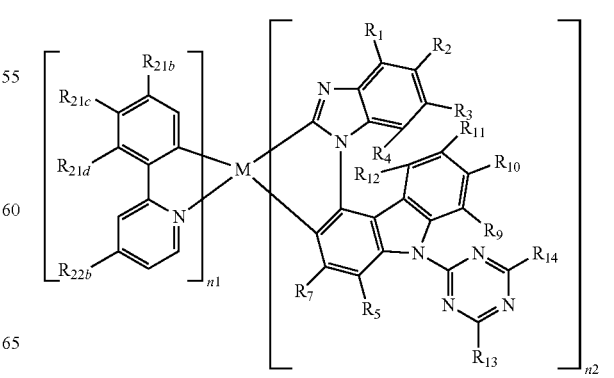

<Formula 1-4>
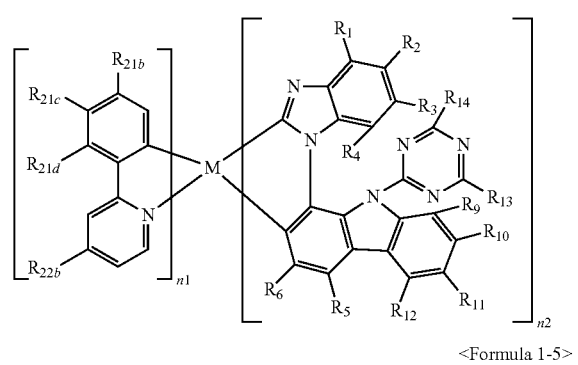
<Formula 1-5>
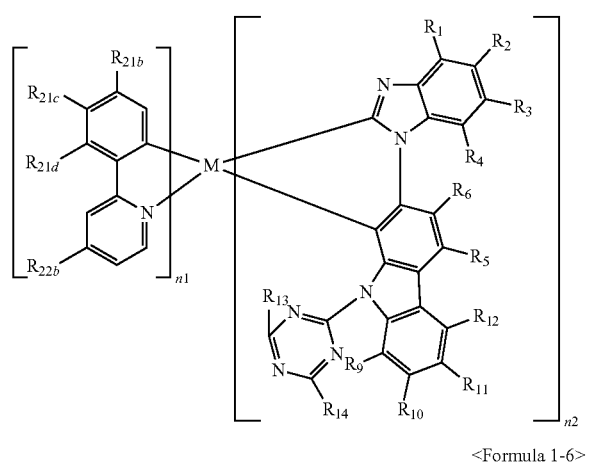
<Formula 1-6>
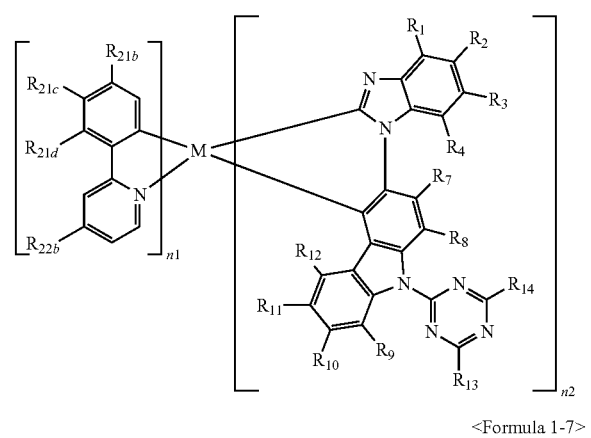
<Formula 1-7>
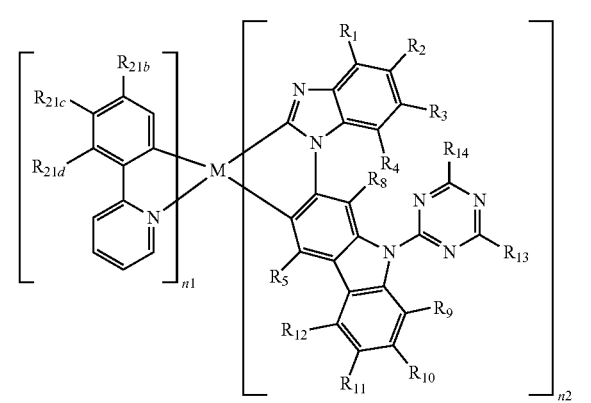
<Formula 1-8>
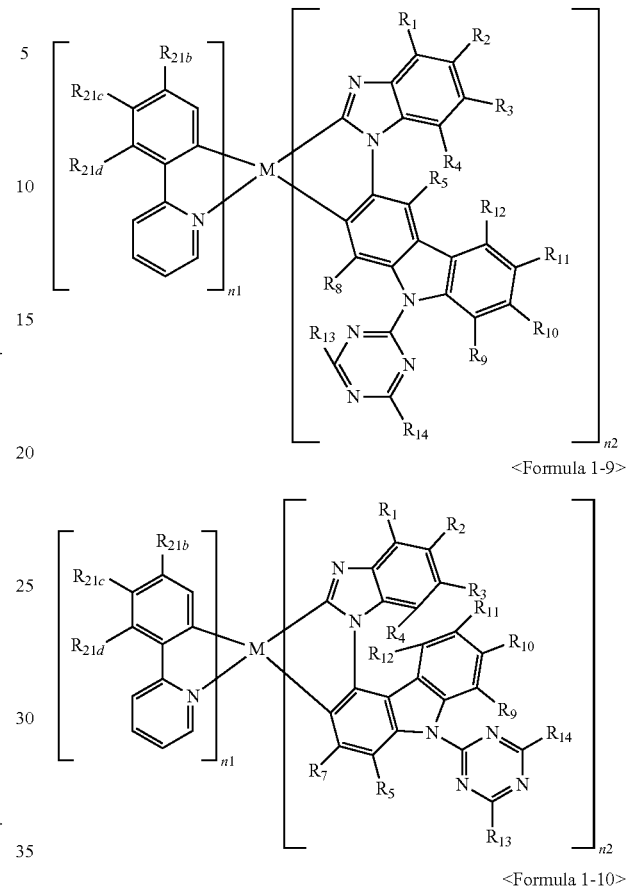
<Formula 1-9>
<Formula 1-10>
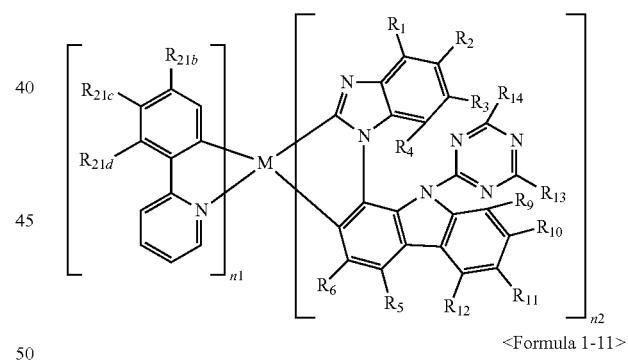
<Formula 1-11>
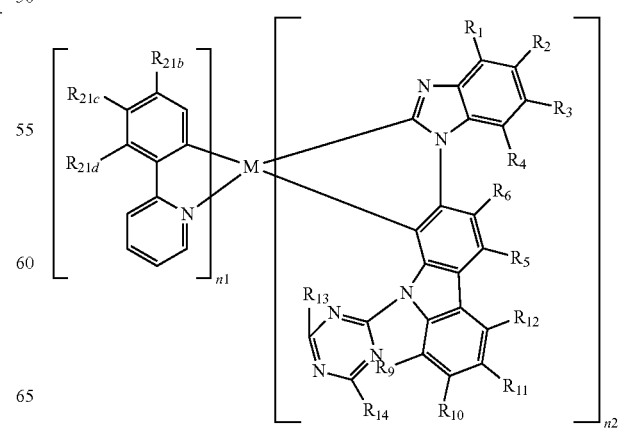

<Formula 1-12>
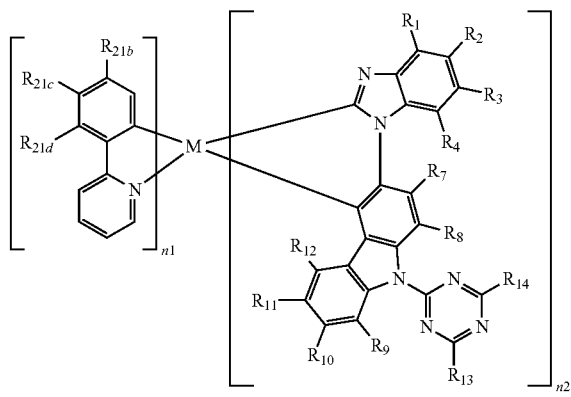
<Formula 1-13>
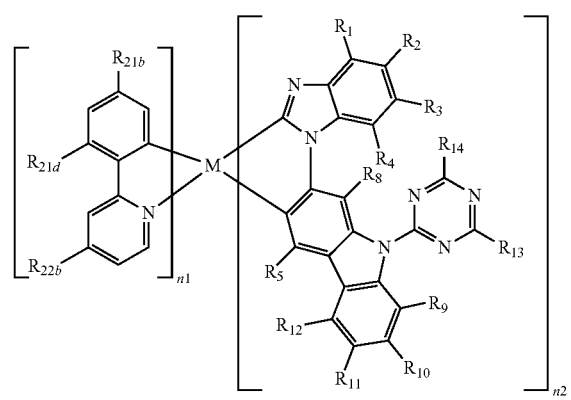
<Formula 1-14>
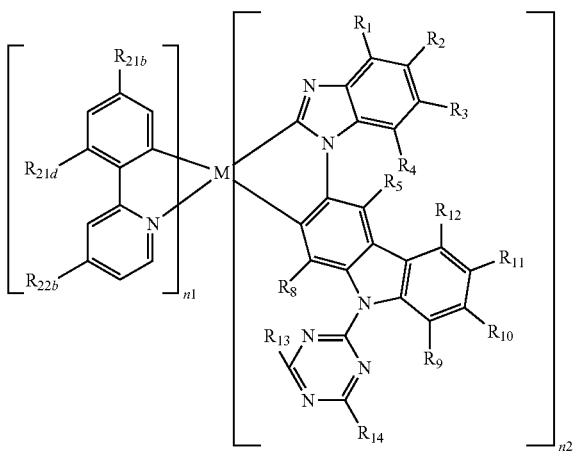
<Formula 1-15>
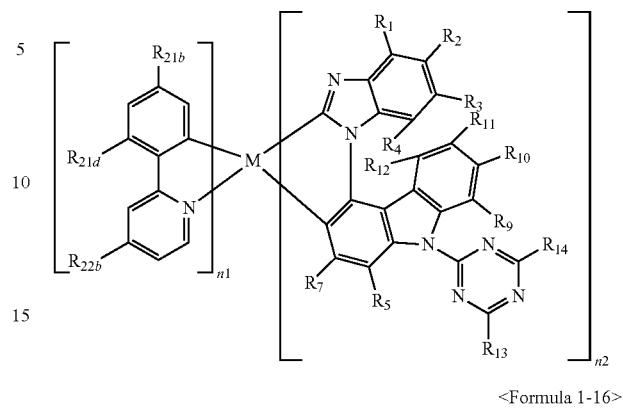
<Formula 1-16>
<Formula 1-17>
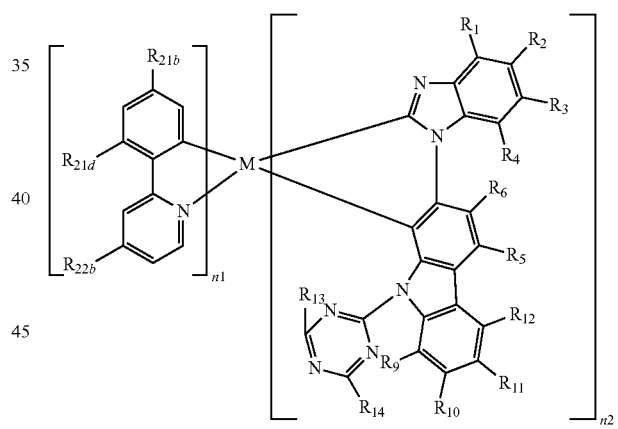
<Formula 1-18>
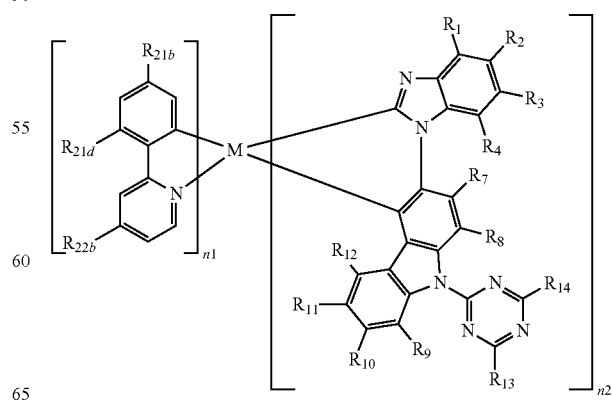

<Formula 1-19>
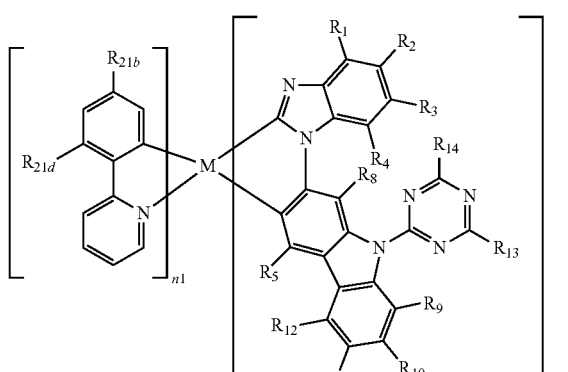

<Formula 1-20>
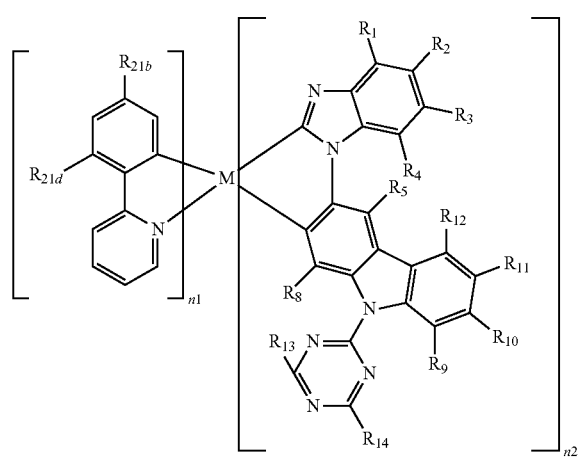

<Formula 1-21>
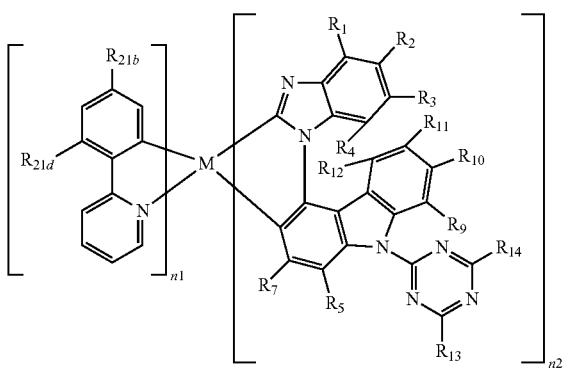

<Formula 1-22>
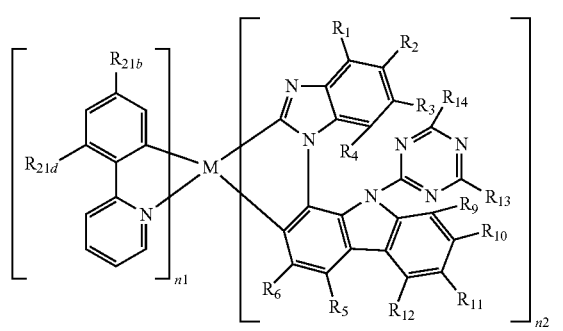

<Formula 1-23>
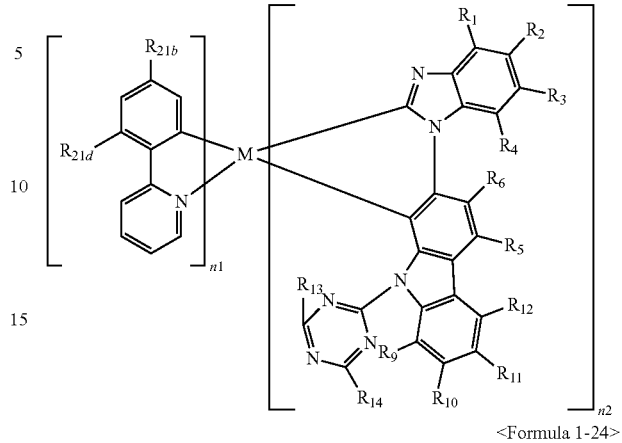

<Formula 1-24>
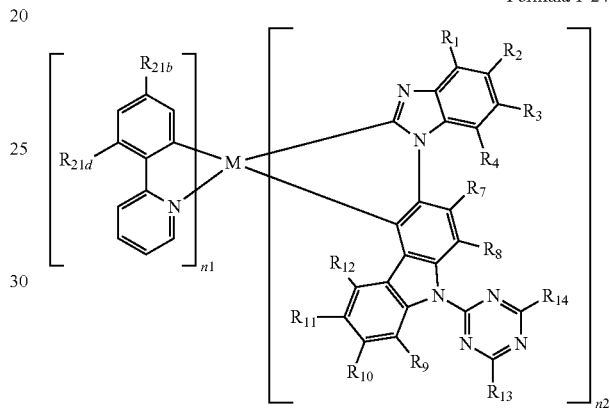

In Formulae 1-1 to 1-24,

M may be, e.g., iridium (Ir) or platinum (Pt);

n1 may be 0, 1, or 2, n2 may be 1, 2, or 3, and a sum of n1 and n2 may be 2 or 3.

$R_1$ to $R_{12}$ may each independently be selected from:

a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, pentoxy group, a phenyl group, a naphthyl group, a pyridinyl group, a pyrimidinyl group, and a triazinyl group;

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group, each substituted with at least one selected from —F, a cyano group, a nitro group, a phenyl group, a naphthyl group, a pyridinyl group, a pyrimidinyl group, a triazinyl group, and —Si($Q_{33}$)($Q_{34}$)($Q_{35}$); and —Si($Q_3$)($Q_4$)($Q_5$), wherein $Q_3$ to $Q_5$ and $Q_{33}$ to $Q_{35}$ may each independently be selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

$R_{13}$ and $R_{14}$ may each independently be selected from a hydrogen or a phenyl group.

$R_{21b}$, $R_{21c}$, and $R_{21d}$ may each independently be selected from —F, —Cl, —CN and —NO$_2$; and a $C_1$-$C_{20}$ alkyl group and a $C_1$-$C_{20}$ alkoxy group, each substituted with at least one selected from —F, —Cl, —CN, and —NO$_2$, $R_{22b}$ may be selected from a $C_1$-$C_{20}$ alkyl group and —N($Q_{41}$)($Q_{42}$), and $Q_{41}$ and $Q_{42}$ may each independently be selected from a hydrogen, a $C_1$-$C_{20}$ alkyl group, a phenyl group, a naphthyl group, and an anthracenyl group.

In an implementation, the organometallic compound represented by Formula 1 may be one of the following Compounds 1 to 5 and 7 to 34.

1

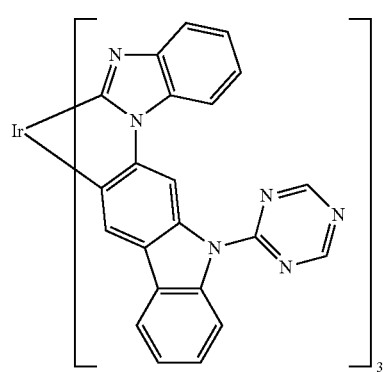

2

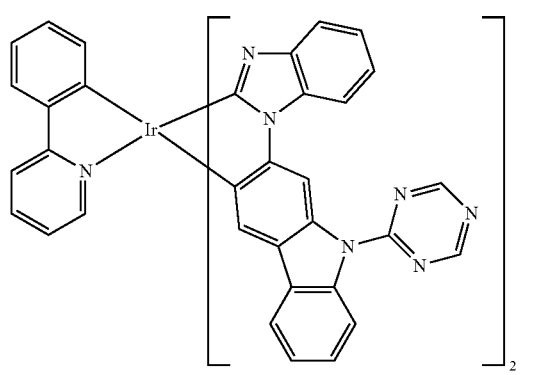

3

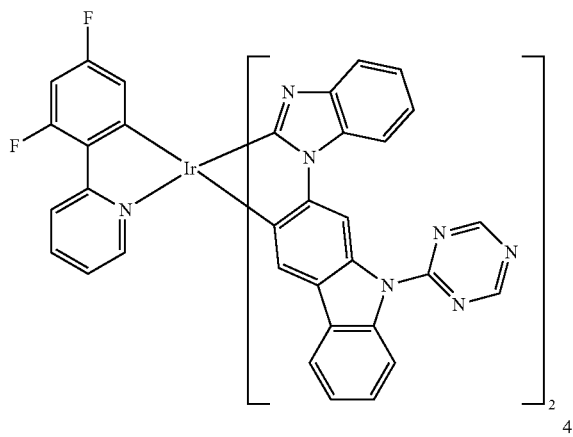

4

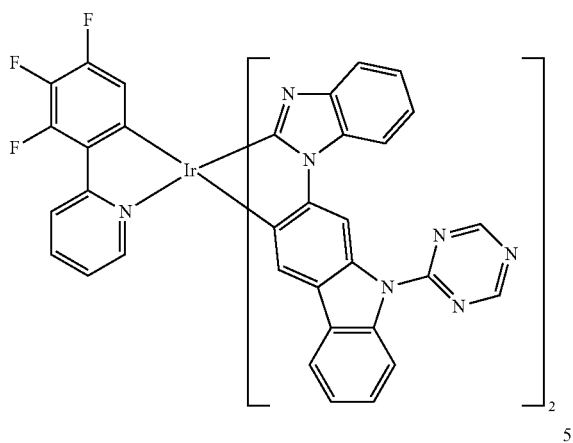

5

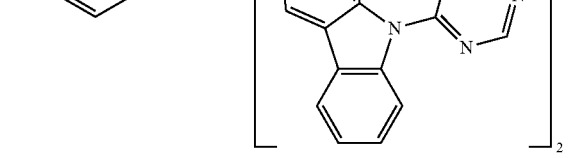

7

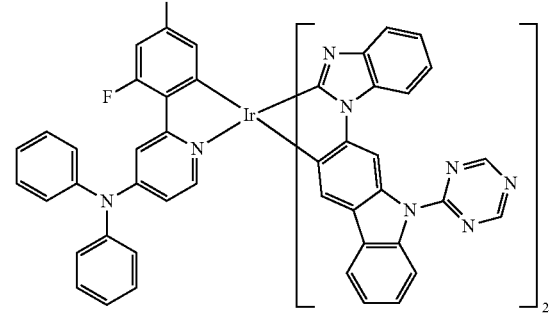

8
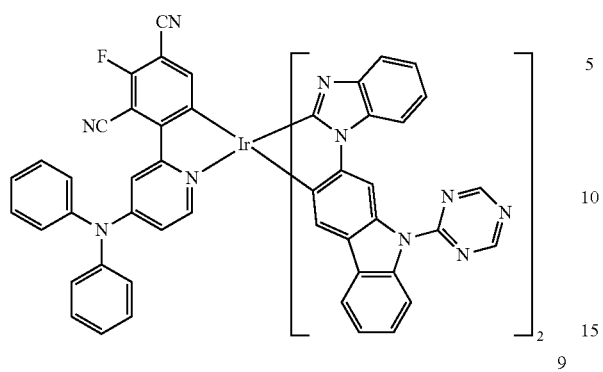
9
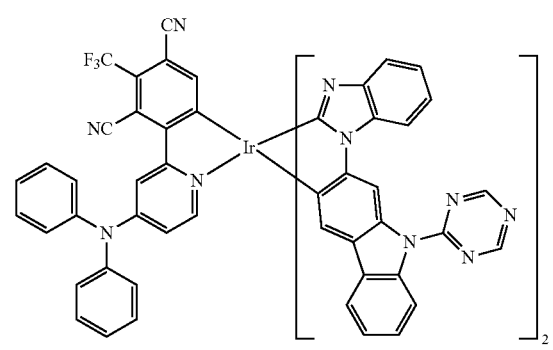
10
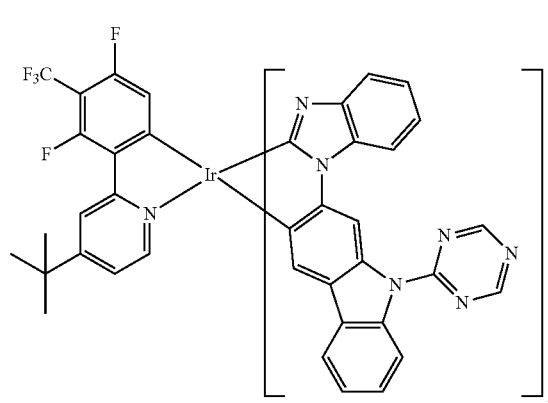
11
12
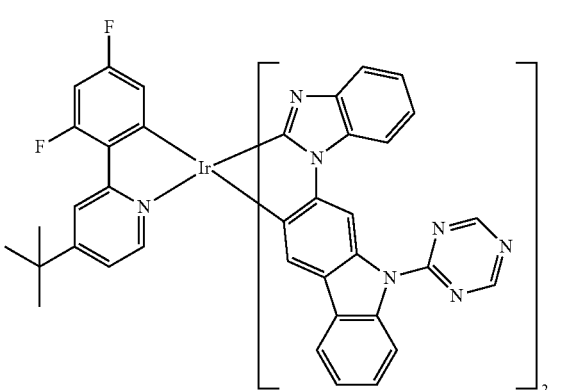
15
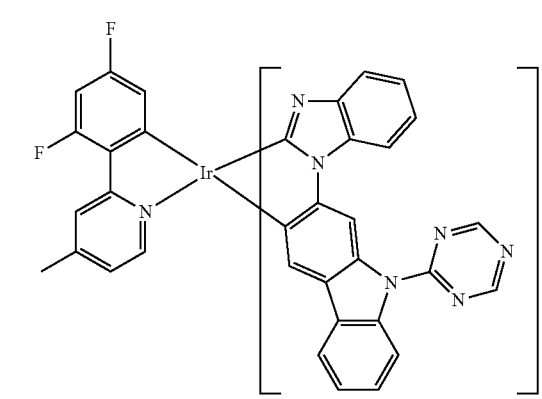
16
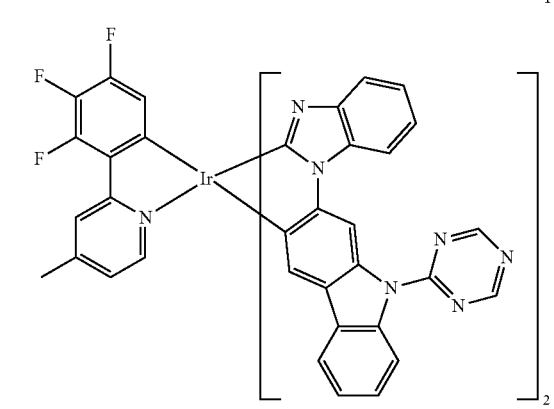
17

18
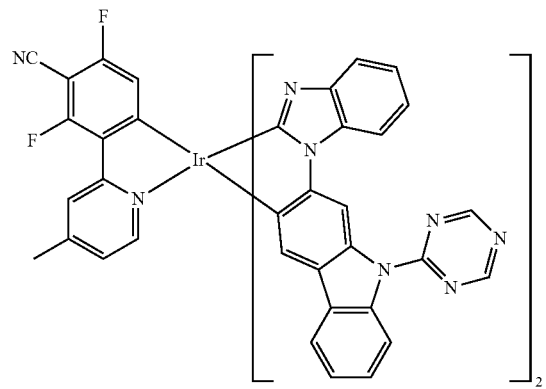
19
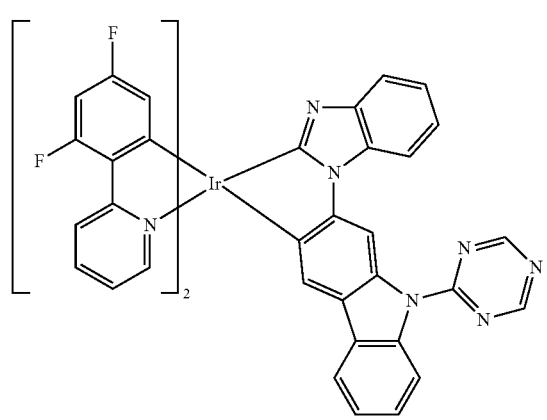
20
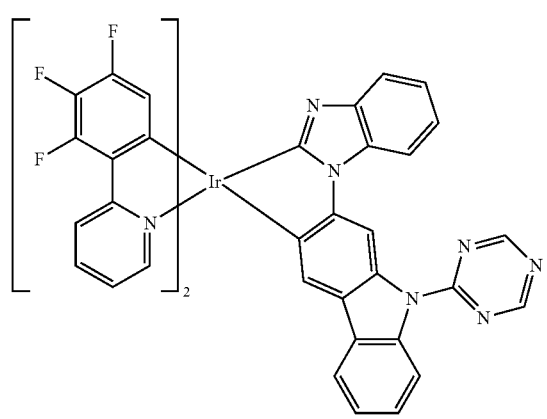
21
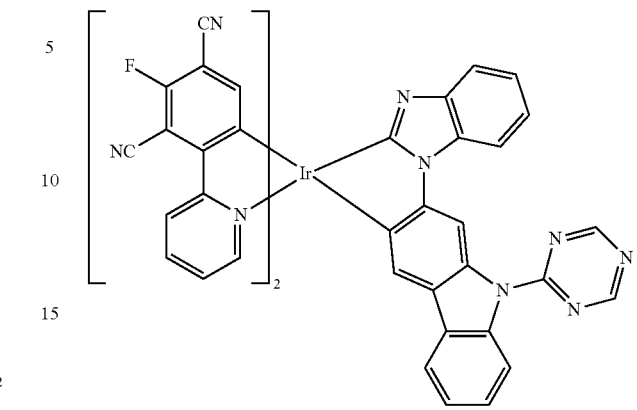
23
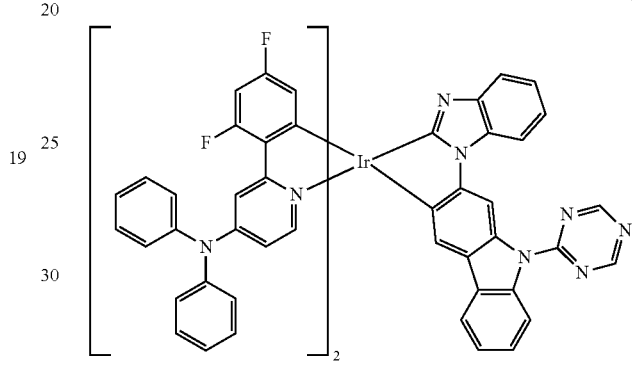
24
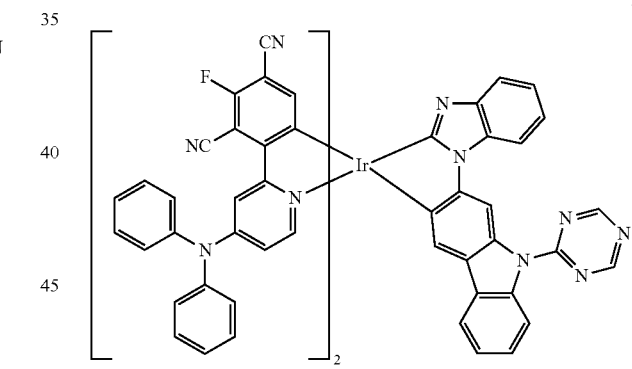
25
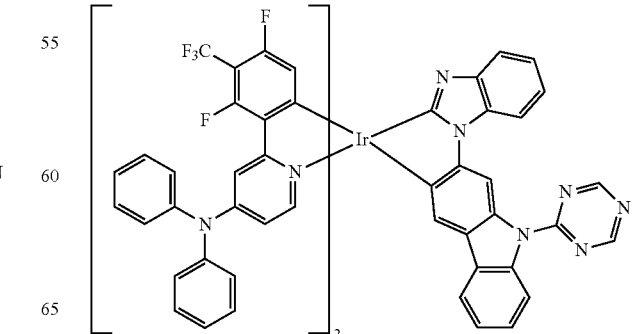

26
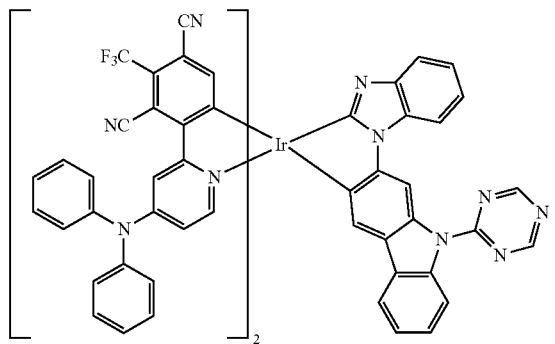
27
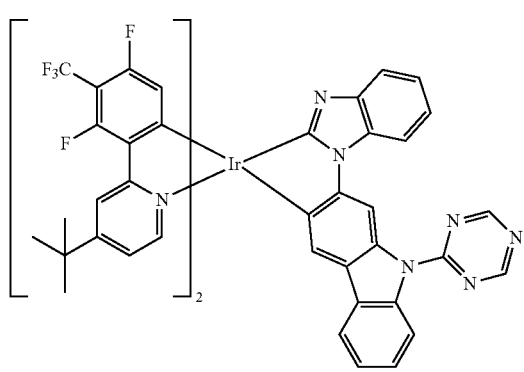
28
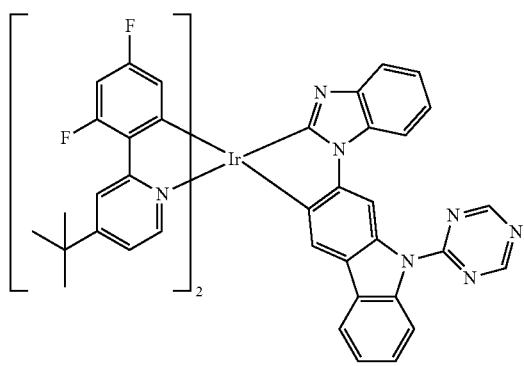
29
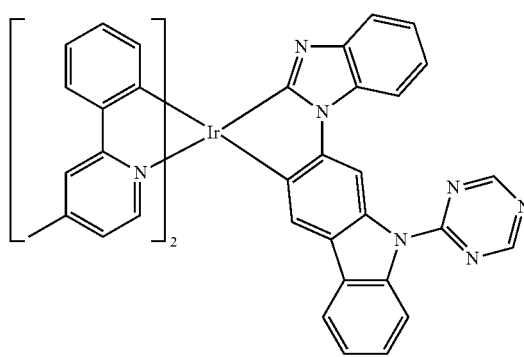
30
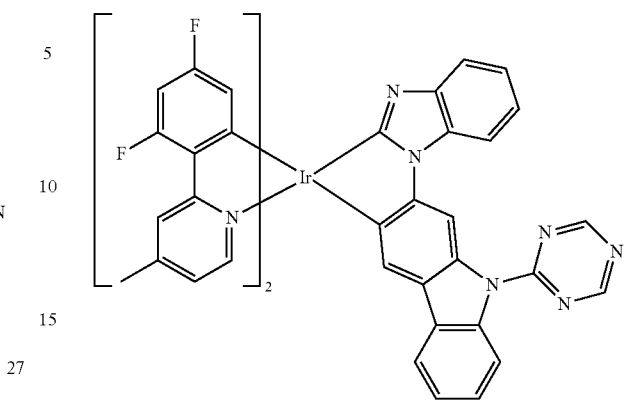
31
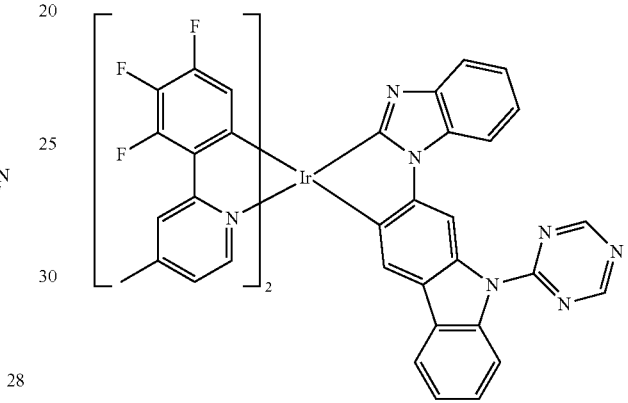
32
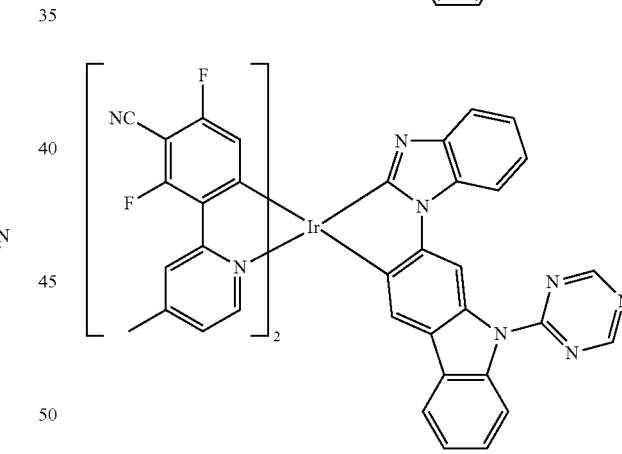
33
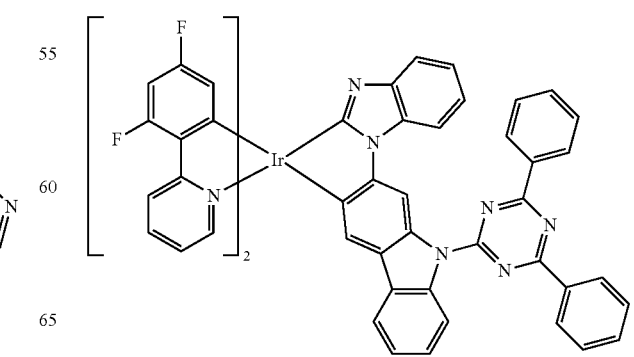

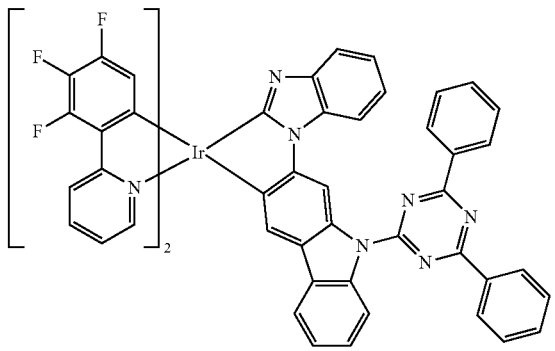

Regarding the organometallic compound, in a ligand illustrated in Formula 2A' below, a benzimidazole-based moiety and a carbazole-based moiety in which a triazolyl group binds to an N atom, may bind to a central metal (M). The benzimidazole-based moiety may be an electron donating group and the carbazole-based moiety may be an electron withdrawing group. Herein, a carbazole-based moiety in the ligand may have lower electron density due to the binding of the trizaolyl group having strong electron withdrawing characteristics to the N atom a carbazole-based moiety. By doing this, in the organometallic compound, electronic stability at a highest occupied molecular orbital (HOMO) level may be increased and electronic unstability at a lowest unoccupied molecular orbital (LUMO) level may be increased. Thus, an energy band gap between a HOMO level and a LUMO level may be increased. As a result, light emitted by the organometallic compound may be light that has been shifted toward a shorter wavelength, e.g., blue-shift light. The ligand of the organometallic compound may easily traps electrons, so that the electrons may form many excitons together with holes provided into an emission layer including the organometallic compound. Accordingly, an organic light-emitting device using the organometallic compound may have high luminescent efficiency.

<Formula 2A'>

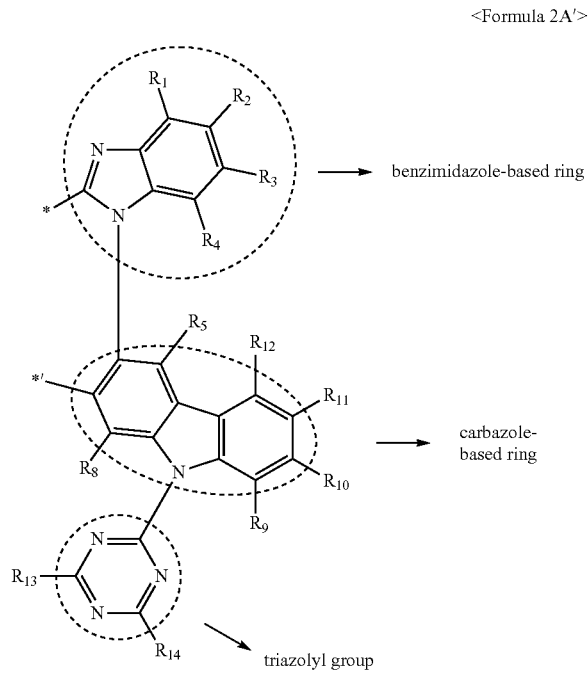

Accordingly, an organic light-emitting device using or including the organometallic compound represented by Formula 1 may have a low-driving voltage and high brightness.

The organometallic compound represented by Formula 1 may be synthesized by a suitable organic synthetic method. A synthesis method of the organometallic compound may be understood in view of the following embodiments.

The organometallic compound of Formula 1 may be used between a pair of electrodes of an organic light-emitting device. In an implementation, the organometallic compound may be included in an electron transport region, e.g., an electron transport layer. In an implementation, the organometallic compound may be included in an emission layer, e.g., as a dopant. For example, an organic light-emitting device according to an embodiment may include: a first electrode; a second electrode facing the first electrode; and an organic layer between the first electrode and the second electrode and that includes an emission layer. The organic layer may include at least one of the organometallic compounds described above.

The expression "(an organic layer) includes at least one organometallic compounds" used herein may include a case in which "(an organic layer) includes identical organometallic compounds of Formula 1 and a case in which (an organic layer) includes two or more different organometallic compounds of Formula 1.

For example, the organic layer may include, as the organometallic compound, only Compound 1. In this regard, Compound 1 may exist in an emission layer of the organic light-emitting device. In some embodiments, the organic layer may include, as the organometallic compound, Compound 1 and Compound 2. In this regard, Compound 1 and Compound 2 may exist in an identical layer (for example, Compound 1 and Compound 2 may all exist in an emission layer), or different layers (for example, Compound 1 may exist in an emission layer and Compound 2 may exist in an electron transport layer).

The organic layer may include i) a hole transport region that is disposed between the first electrode (anode) and the emission layer and includes at least one of a hole injection layer, a hole transport layer, a buffer layer, and an electron blocking layer, and/or ii) an electron transport region that is disposed between the emission layer and the second electrode (cathode) and includes at least one selected from a hole blocking layer, an electron transport layer, and an electron injection layer. The emission layer may include the organometallic compound represented by Formula 1.

The term "organic layer" used herein refers to a single layer and/or a plurality of layers disposed between the first electrode and the second electrode of an organic light-emitting device. A material included in the "organic layer" is not limited to an organic material.

FIG. 1 illustrates a schematic view of an organic light-emitting device 10 according to an embodiment. The organic light-emitting device 10 includes a first electrode 110, an organic layer 150, and a second electrode 190.

Hereinafter, the structure of an organic light-emitting device according to an embodiment and a method of manufacturing an organic light-emitting device according to an embodiment will be described in connection with FIG. 1.

In FIG. 1, a substrate may be additionally disposed under the first electrode 110 or above the second electrode 190. The substrate may be a glass substrate or transparent plastic substrate, each with excellent mechanical strength, thermal stability, transparency, surface smoothness, ease of handling, and water-resistance.

The first electrode 110 may be formed by depositing or sputtering a material for forming the first electrode on the substrate. When the first electrode 10 is an anode, the material for the first electrode may be selected from materials with a high work function to make holes be easily injected. The first electrode 110 may be a reflective electrode or a transmissive electrode. The material for the first electrode may be a transparent and highly conductive material, and examples of such a material are indium tin oxide (ITO), indium zinc oxide (IZO), tin oxide ($SnO_2$), and zinc oxide (ZnO). When the first electrode 110 is a semi-transmissive electrode or a reflective electrode, as a material for forming the first electrode, at least one of magnesium (Mg), aluminum (Al), aluminum-lithium (Al—Li), calcium (Ca), magnesium-indium (Mg—In), magnesium-silver (Mg—Ag) may be used.

The first electrode 110 may have a single-layer structure, or a multi-layer structure including two or more layers. For example, the first electrode 110 may have a three-layered structure of ITO/Ag/ITO.

An organic layer 150 may be disposed on the first electrode 110. The organic layer 150 may include an emission layer.

The organic layer 150 may further include a hole transport region disposed between the first electrode and the emission layer, and/or an electron transport region disposed between the emission layer and the second electrode.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL).

The hole transport region may have a single-layered structure formed of a single material, a single-layered structure formed of a plurality of different materials, or a multi-layered structure having a plurality of layers formed of a plurality of different materials.

For example, the hole transport region may have a single-layered structure formed of a plurality of different materials, or a structure of hole injection layer/hole transport layer, a structure of hole injection layer/hole transport layer/buffer layer, a structure of hole injection layer/buffer layer, a structure of hole transport layer/buffer layer, or a structure of hole injection layer/hole transport layer/electron blocking layer, wherein layers of each structure are sequentially stacked from the first electrode 110 in this stated order.

When the hole transport region includes a hole injection layer, the hole injection layer may be formed on the first electrode 110 by using various methods, such as vacuum deposition, spin coating casting, a Langmuir-Blodgett (LB) method, ink-jet printing, laser-printing, or laser-induced thermal imaging.

When a hole injection layer is formed by vacuum deposition, for example, the vacuum deposition may be performed at a temperature of a deposition temperature of about 100 to about 500° C., at a vacuum degree of about $10^{-8}$ to about $10^{-3}$ torr, and at a deposition rate of about 0.01 to about 100 Å/sec in consideration of a compound for a hole injection layer to be deposited, and the structure of a hole injection layer to be formed.

When a hole injection layer is formed by spin coating, the spin coating may be performed at a coating rate of about 2000 rpm to about 5000 rpm, and at a temperature of about 80° C. to 200° C. in consideration of a compound for a hole injection layer to be deposited, and the structure of a hole injection layer to be formed.

When the hole transport region includes a hole transport layer, the hole transport layer may be formed on the first electrode 110 or the hole injection layer by using various methods, such as vacuum deposition, spin coating, casting, a LB method, ink-jet printing, laser-printing, or laser-induced thermal imaging. When the hole transport layer is formed by vacuum deposition or spin coating, deposition and coating conditions for the hole transport layer may be determined by referring to the deposition and coating conditions for the hole injection layer.

The hole transport region may include at least one selected from m-MTDATA, TDATA, 2-TNATA, NPB, β-NPB, TPD, Spiro-TPD, Spiro-NPB, α-NPB, TAPC, HMTPD, 4,4',4''-tris(N-carbazolyl)triphenylamine (TCTA), polyaniline/dodecylbenzenesulfonic acid (Pani/DBSA), poly(3,4-ethylenedioxythiophene)/poly(4-styrenesulfonate) (PEDOT/PSS), polyaniline/camphor sulfonicacid (Pani/CSA), (polyaniline)/poly(4-styrenesulfonate) (PANI/PSS), a compound represented by Formula 201 below, and a compound represented by Formula 202 below:

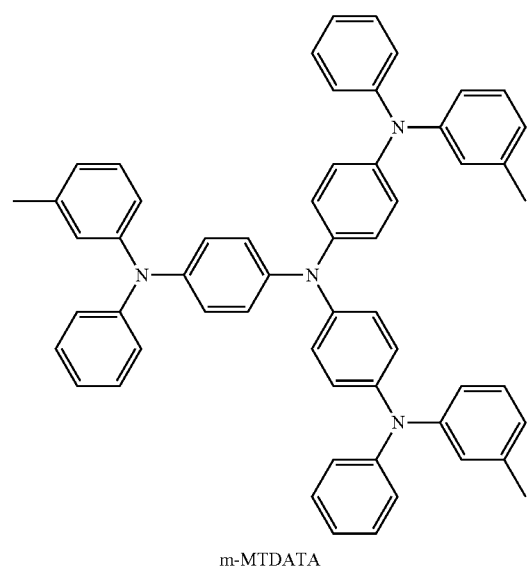

m-MTDATA

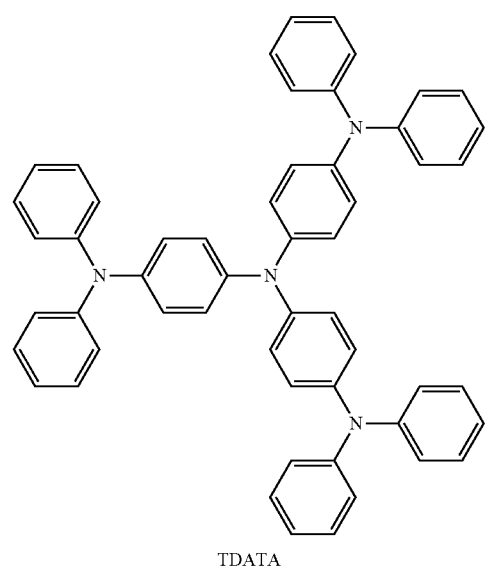

TDATA

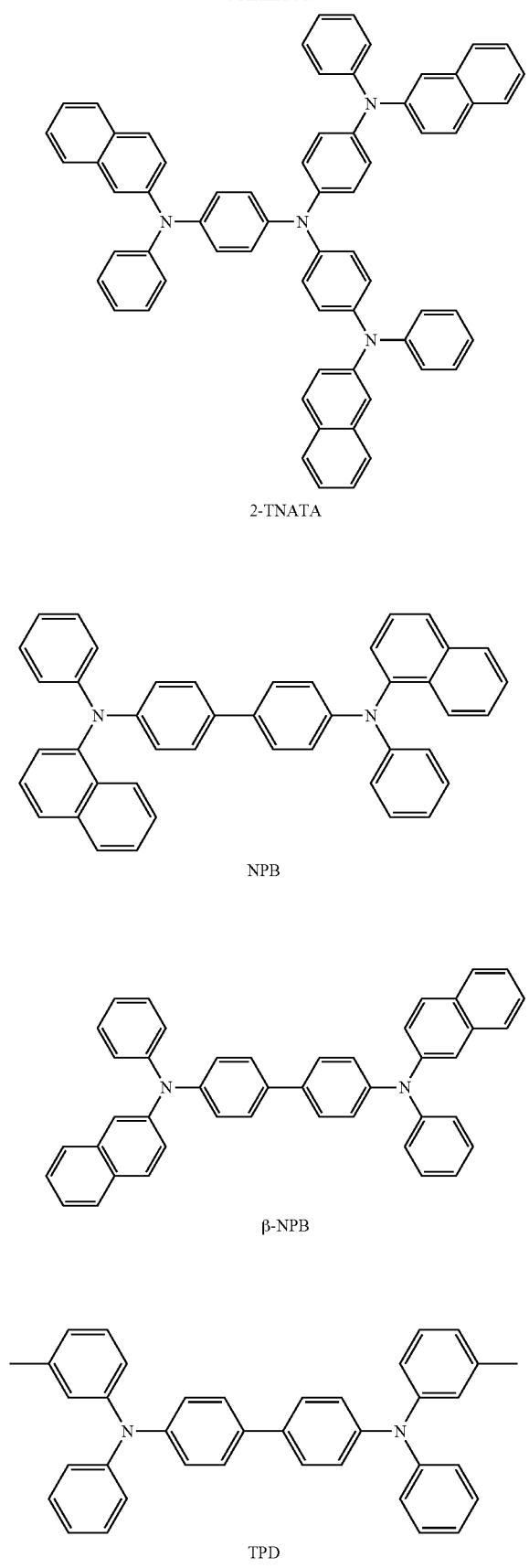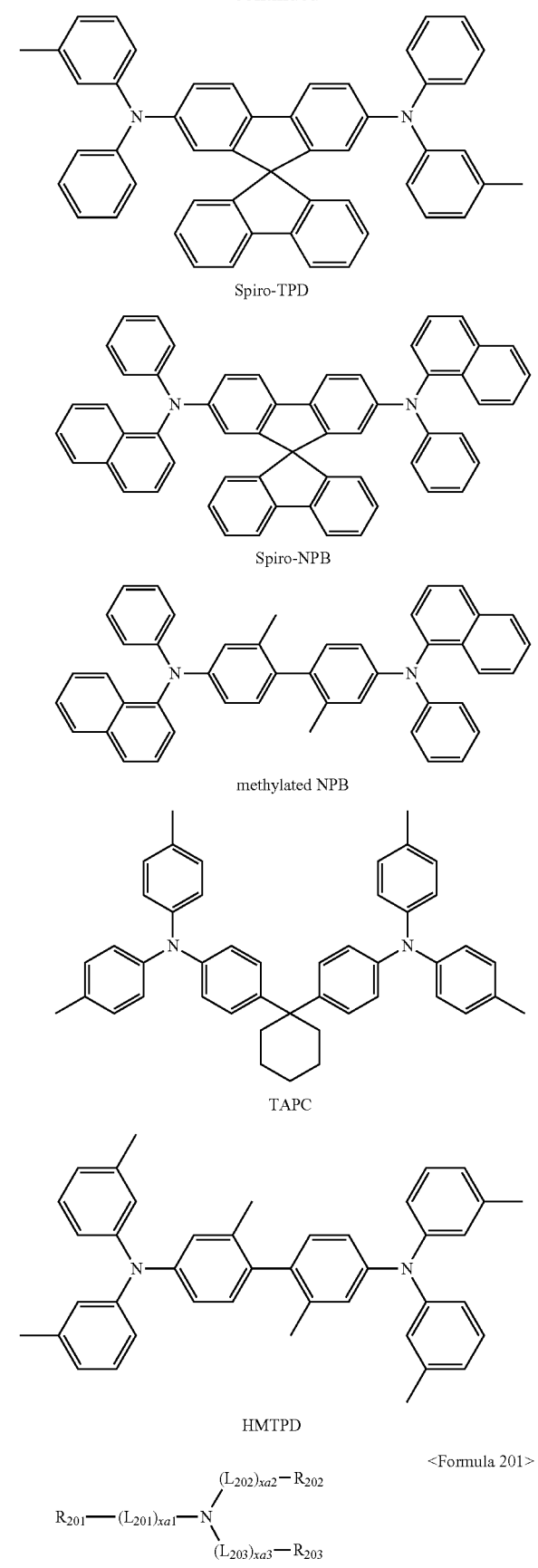

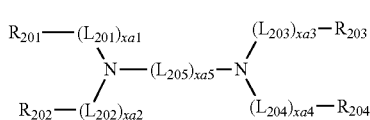
<Formula 202>

In Formulae 201 and 202, $L_{201}$ to $L_{205}$ may each independently be selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, and a substituted or unsubstituted divalent non-aromatic condensed heteropolycyclic group;

xa1 to xa4 may each independently be selected from 0, 1, 2, and 3;

xa5 may be selected from 1, 2, 3, 4, and 5; and $R_{201}$ to $R_{204}$ may each independently be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In some embodiments, in Formulae 201 and 202, $L_{201}$ to $L_{205}$ may each independently be selected from a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may each independently be 0, 1, or 2;

xa5 may be 1, 2, or 3;

$R_{201}$ to $R_{204}$ may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

The compound represented by Formula 201 may be represented by Formula 201A:

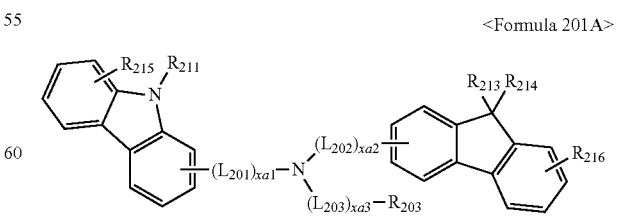
<Formula 201A>

For example, the compound represented by Formula 201 may be represented by Formula 201A-1 below.

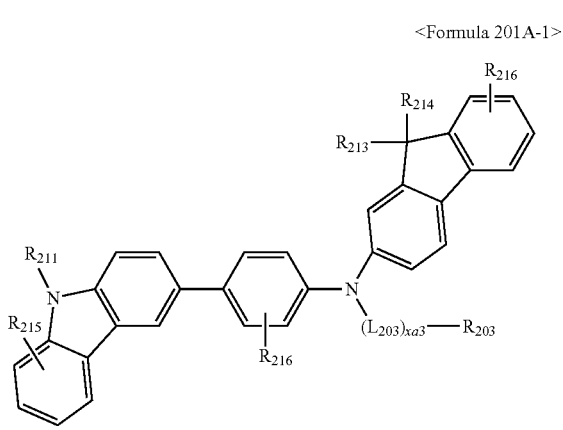

<Formula 201A-1>

For example, the compound represented by Formula 202 may be represented by Formula 202A below.

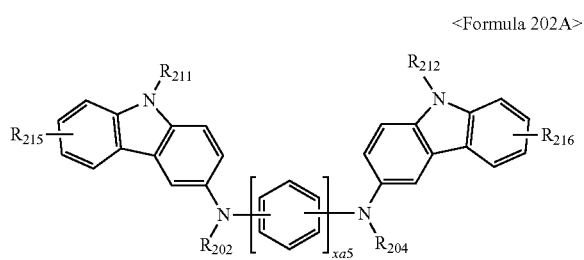

<Formula 202A>

$L_{201}$ to $L_{203}$, xa1 to xa3, xa5, and $R_{202}$ to $R_{204}$ in Formulae 201A, 201A-1, and 202A are already described above, $R_{211}$ is the same as defined in connection with $R_{203}$, and $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monvalent non-aromatic condensed polycyclic group, and a monvalent non-aromatic condensed heteropolycyclic group.

For example, in Formulae 201A, 201A-1, and 202A, $L_{201}$ to $L_{203}$ may each independently be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinoxalinylene group, a quinoxalinylene group, a quinazolinylene group, a carbazolylene group, and a triazinylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may each independently be 0 or 1;

$R_{203}$, $R_{211}$, and $R_{212}$ may each independently be selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may each independently be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may each independently be selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa5 is 1 or 2.

$R_{213}$ and $R_{214}$ in Formulae 201A, and 201A-1 may bind to each other to form a saturated or unsaturated ring.

The compound represented by Formula 201, and/or the compound represented by Formula 202 may include compounds HT1 to HT20 illustrated below.

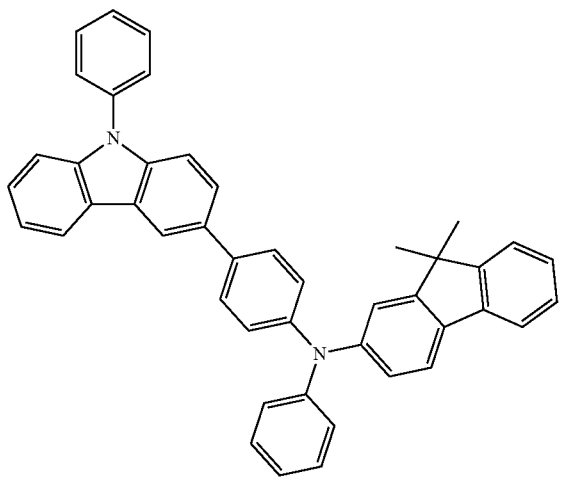

HT1

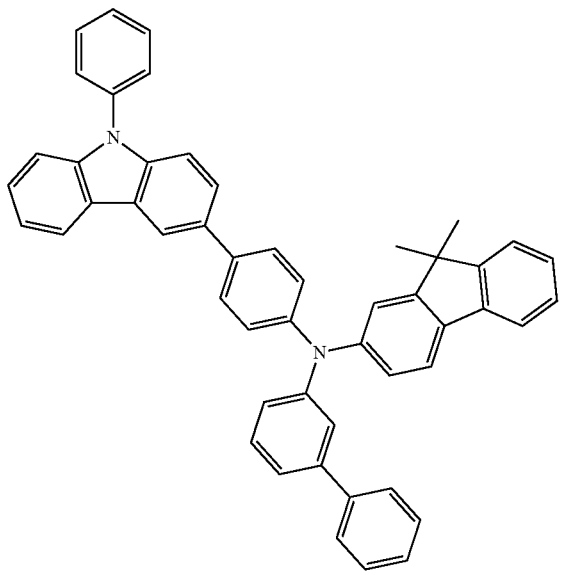

HT2

HT3
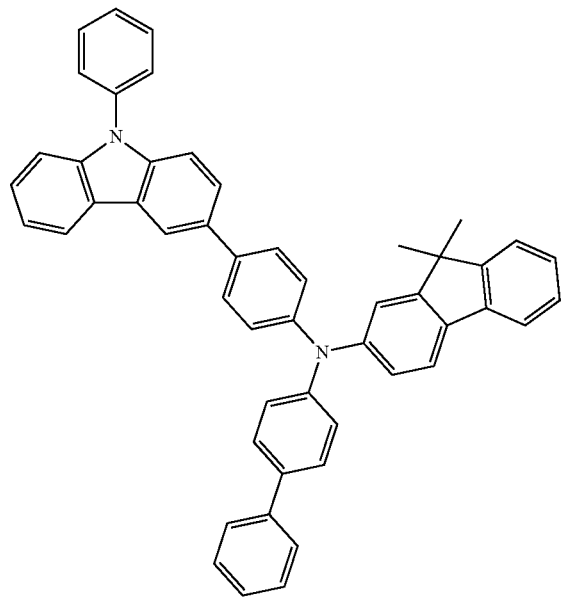
HT5
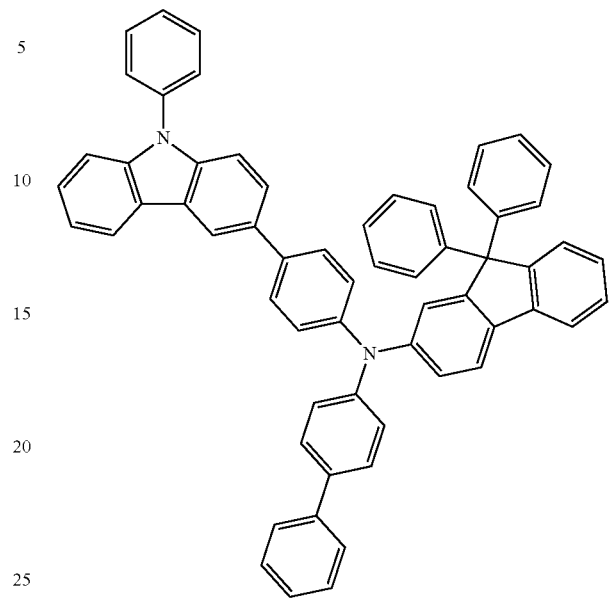
HT4
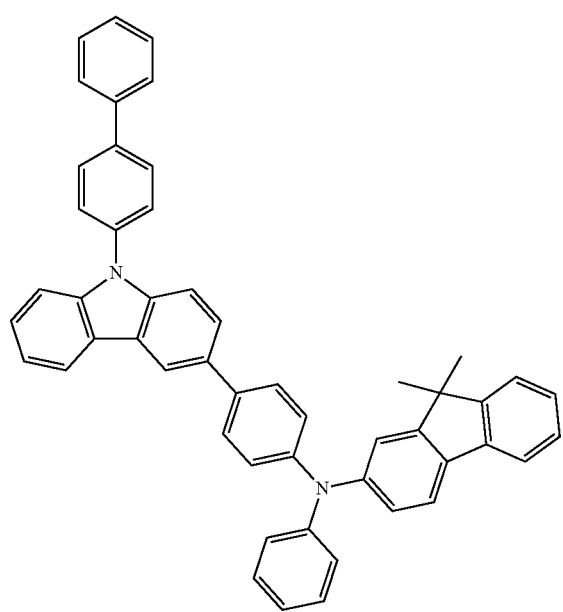
HT6
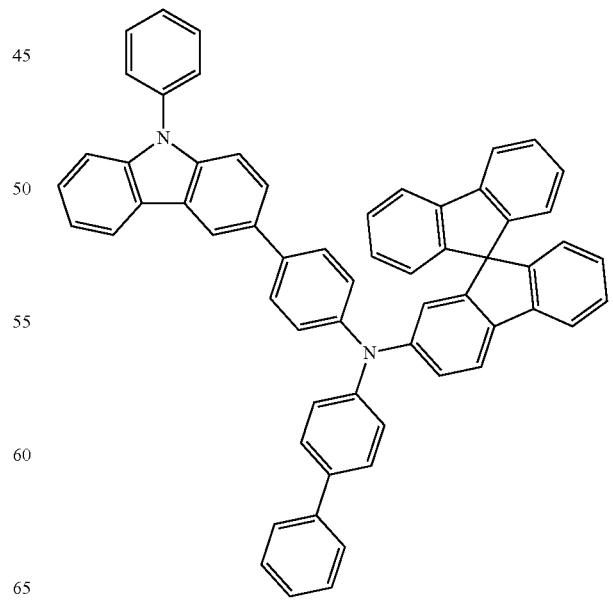

HT7
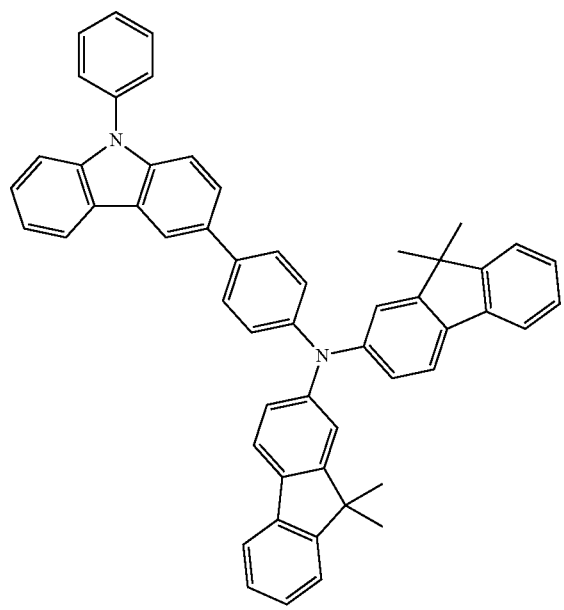
HT9
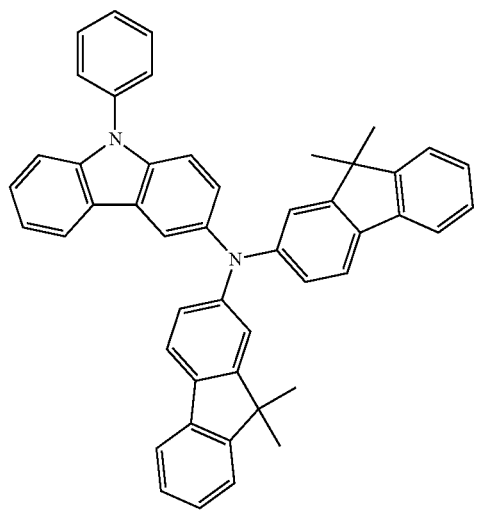
HT8
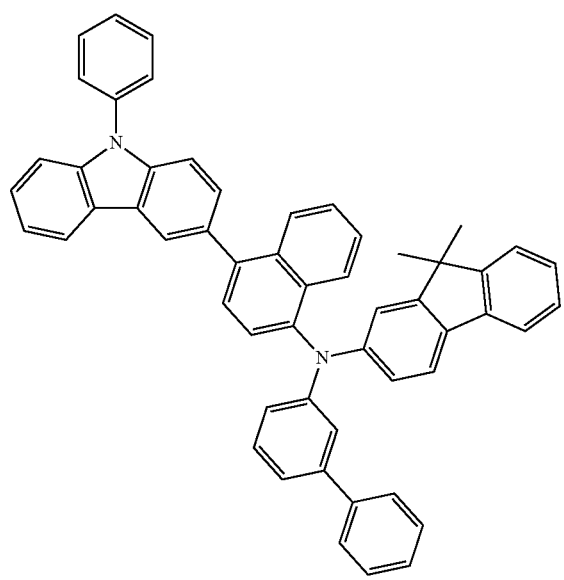
HT10
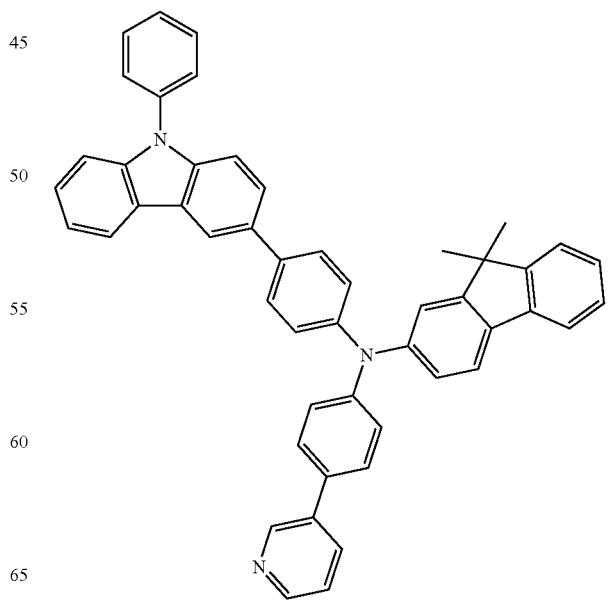

HT11
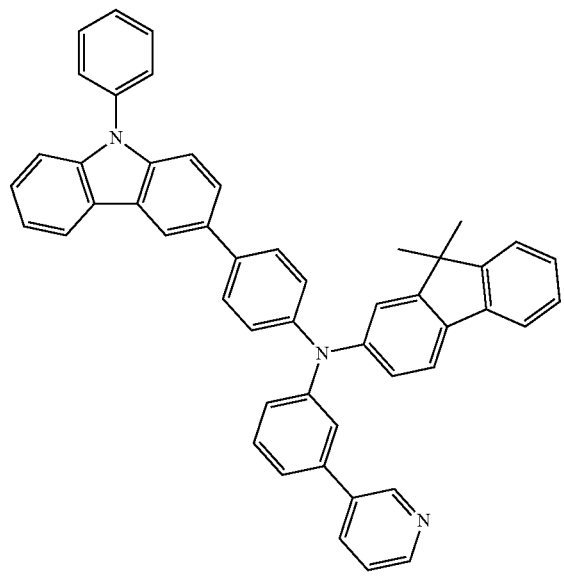
HT12
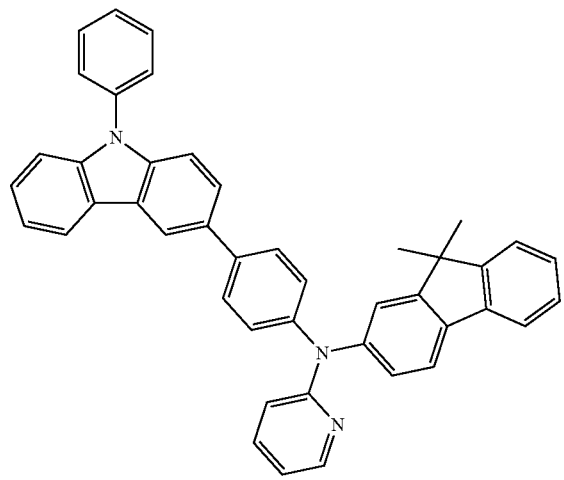
HT13
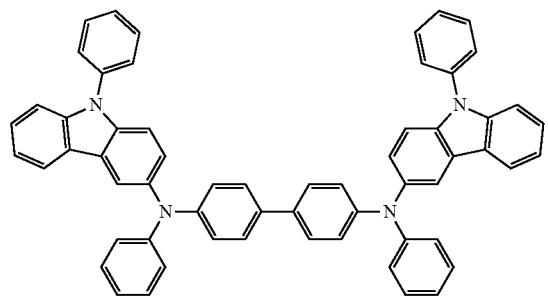
HT14
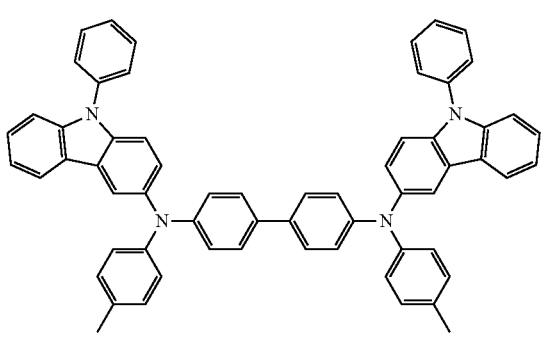
HT15
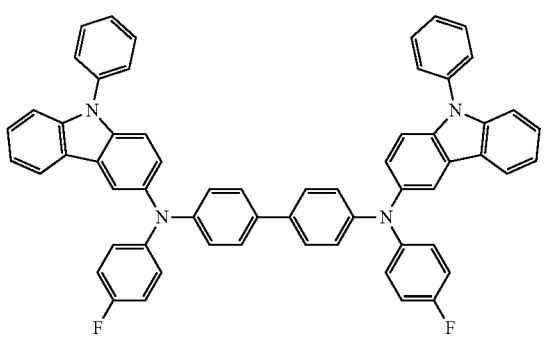
HT16
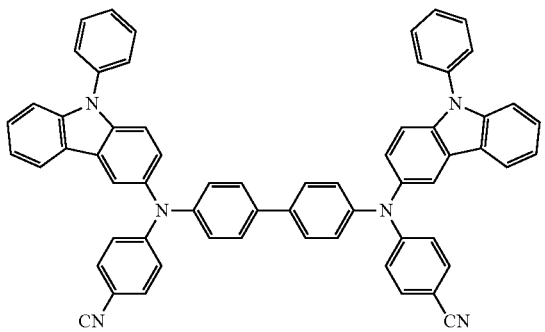
HT17
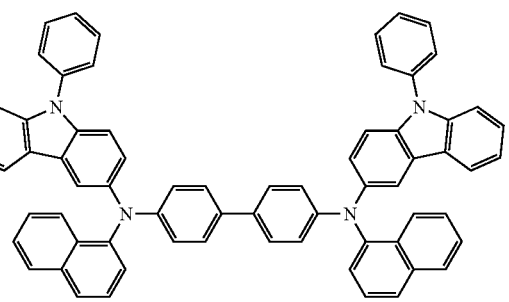

HT18

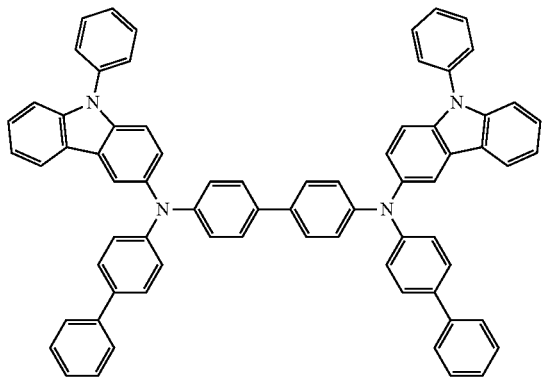

HT19

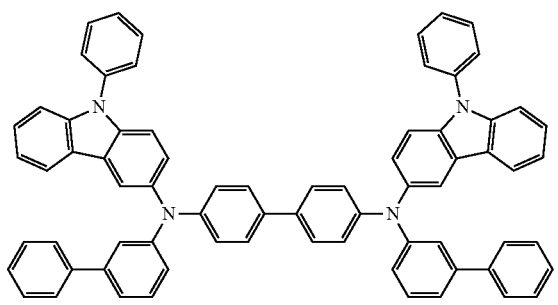

HT20

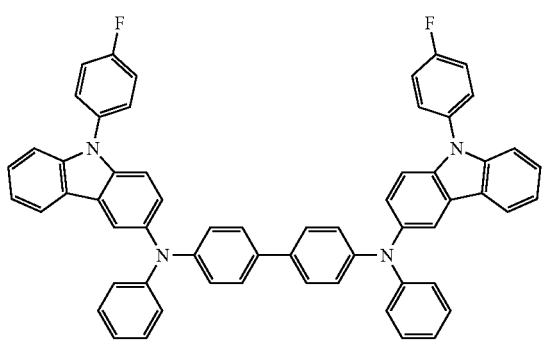

A thickness of the hole transport region may be in a range of about 100 Å to about 10,000 Å, e.g., about 100 Å to about 1000 Å. When the hole transport region includes a hole injection layer and a hole transport layer, the thickness of the hole injection layer may be in a range of about 100 Å to about 10,000 Å, e.g., about 100 Å to about 1,000 Å, and the thickness of the hole transport layer may be in a range of about 50 Å to about 2,000 Å, e.g., about 100 Å to about 1,500 Å. When the thicknesses of the hole transport region, the hole injection layer, and the hole transport layer are within these ranges, satisfactory hole transporting characteristics may be obtained without a substantial increase in driving voltage.

The hole transport region may further include, in addition to these materials, a charge-generation material for the improvement of conductive properties. The charge-generation material may be homogeneously or unhomogeneously dispersed in the hole transport region.

The charge-generation material may be, for example, a p-dopant. The p-dopant may include one selected from a quinone derivative, a metal oxide, and a cyano group-containing compound. Examples of the p-dopant may include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and Compound HT-D1 illustrated below.

<Compound HT-D1>

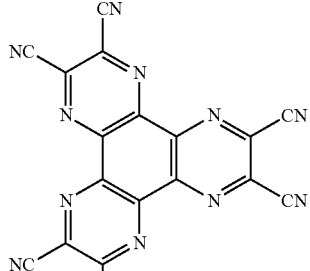

<F4-TCNQ>

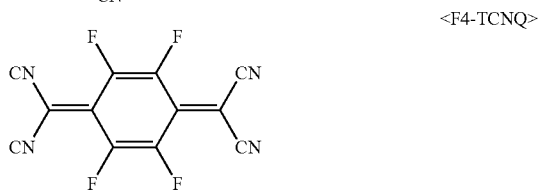

The hole transport region may further include, in addition to the hole injection layer and the hole transport layer, at least one of a buffer layer and an electron blocking layer. Since the buffer layer may compensate for an optical resonance distance according to a wavelength of light emitted from the emission layer, light-emission efficiency of a formed organic light-emitting device may be improved. For use as a material included in the buffer layer, materials that are included in the hole transport region may be used. The electron blocking layer prevents injection of electrons from the electron transport region.

For example, a material for the electron blocking layer may be mCP.

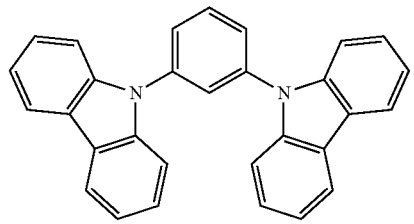

mCP

An emission layer may be formed on the first electrode 110 or the hole transport region by using various methods, e.g., vacuum deposition, spin coating, casting, a LB method, ink-jet printing, laser-printing, or laser-induced thermal imaging. When the emission layer is formed by vacuum deposition or spin coating, deposition and coating conditions for the emission layer may be determined by referring to the deposition and coating conditions for the hole injection layer.

When the organic light-emitting device 10 is a full color organic light-emitting device, the emission layer may be patterned into a red emission layer, a green emission layer, or a blue emission layer, according to a sub pixel. In some embodiments, the emission layer may have a stacked structure of a red emission layer, a green emission layer, and a blue emission layer, or may include a red-light emission material, a green-light emission material, and a blue-light emission material, which are mixed with each other in a single layer, to emit white light.

The emission layer may include the organometallic compound represented by Formula 1.

The emission layer may include a host and a dopant. The dopant may include the organometallic compound represented by Formula 1.

The host may include at least one selected from TPBi, TBADN, ADN (also referred to as "DNA"), CBP, CDBP, and TCP:

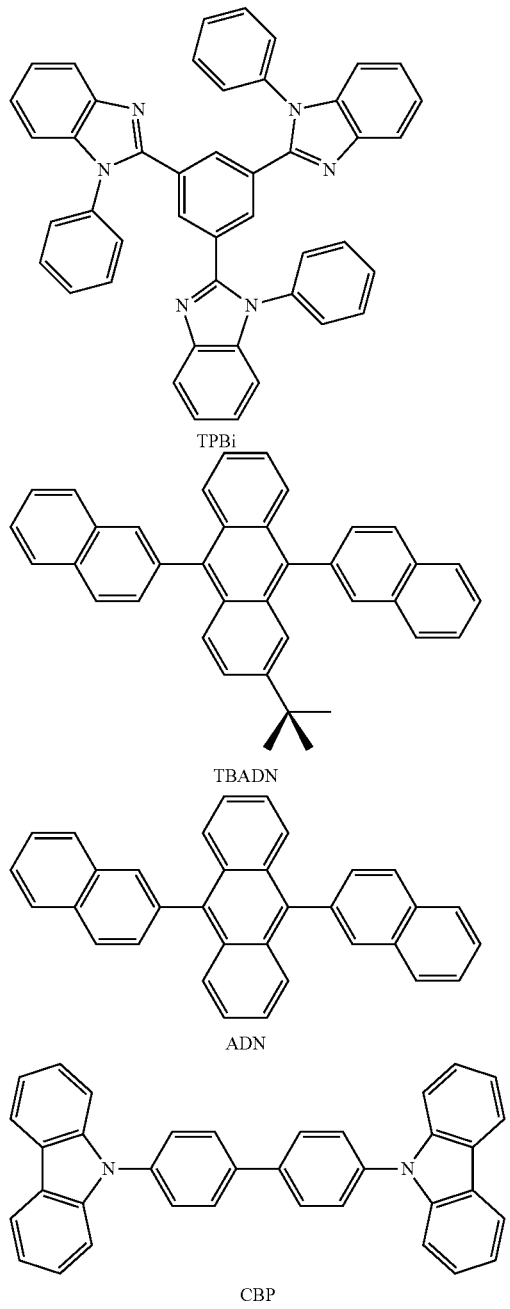

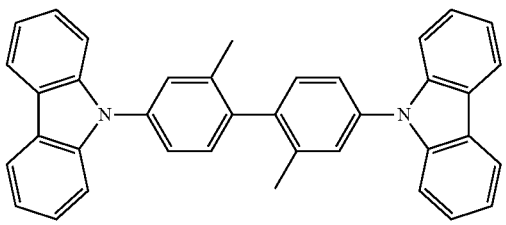

CDBP

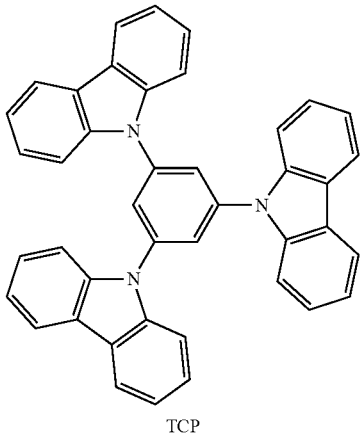

TCP

In some embodiments, the host may include a compound represented by Formula 301 below.

$$Ar_{301}\text{-}[(L_{301})_{xb1}\text{-}R_{301}]_{xb2}$$ <Formula 301> wherein in Formula 301, $Ar_{301}$ may be selected from naphthalene, heptalene, fluorenene, spiro-fluorenene, benzofluorenene, dibenzofluorenene, phenalene, phenanthrene, anthracene, fluoranthene, triphenylene, pyrene, chrysene, naphthacene, picene, perylene, pentaphene, and indenoanthracene;

a naphthalene group, a heptalene group, a fluorenene group, a spiro-fluorenene group, a benzofluorenene group, a dibenzofluorenene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ are each independently selected from a hydrogen, a $C_1$-$C_{60}$ alkyl group, a $C_2$-$C_{60}$ alkenyl group, a $C_2$-$C_{60}$ aryl group, and a $C_1$-$C_{60}$ heteroaryl group);

L₃₀₁ may be the same as explained in connection with L₂₀₁;

R₃₀₁ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazol group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3;

xb2 may be selected from 1, 2, 3, and 4.

wherein in Formula 301,

L₃₀₁ may be selected from a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

R₃₀₁ may be selected from a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group.

For example, the host may include a compound represented by Formula 301A below:

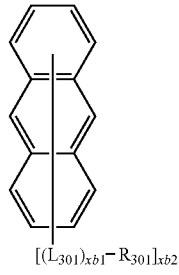

<Formula 301A>

$[(L_{301})_{xb1}-R_{301}]_{xb2}$

Descriptions of substituents of Formula 301A may be understood by referring to the descriptions provided herein.

The compound represented by Formula 301 may include at least one of Compounds H1 to H42.

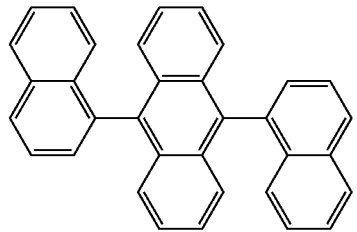

H1

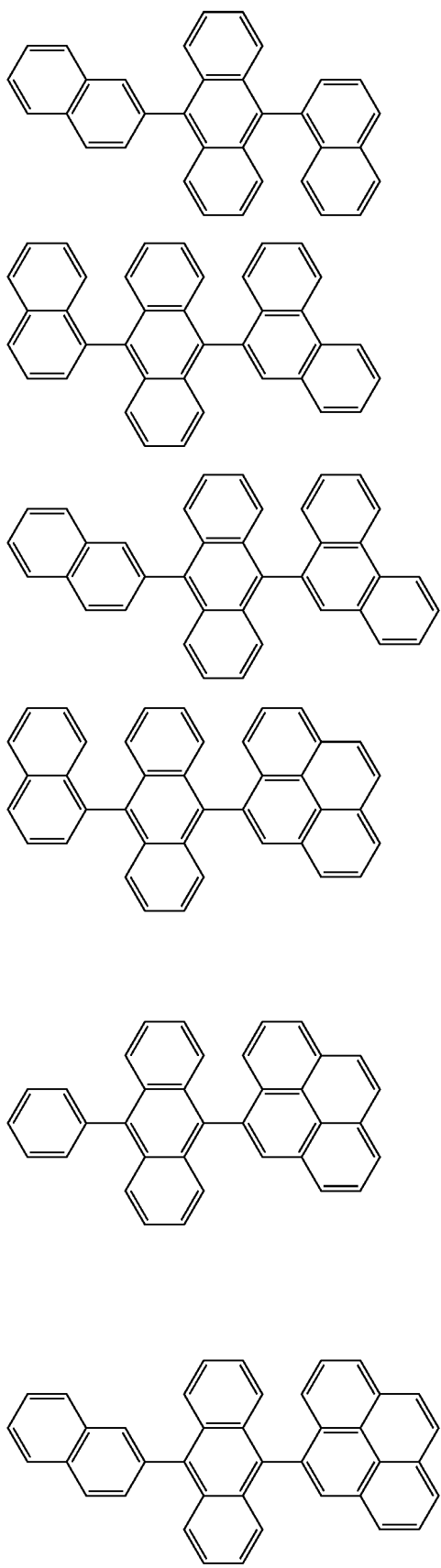
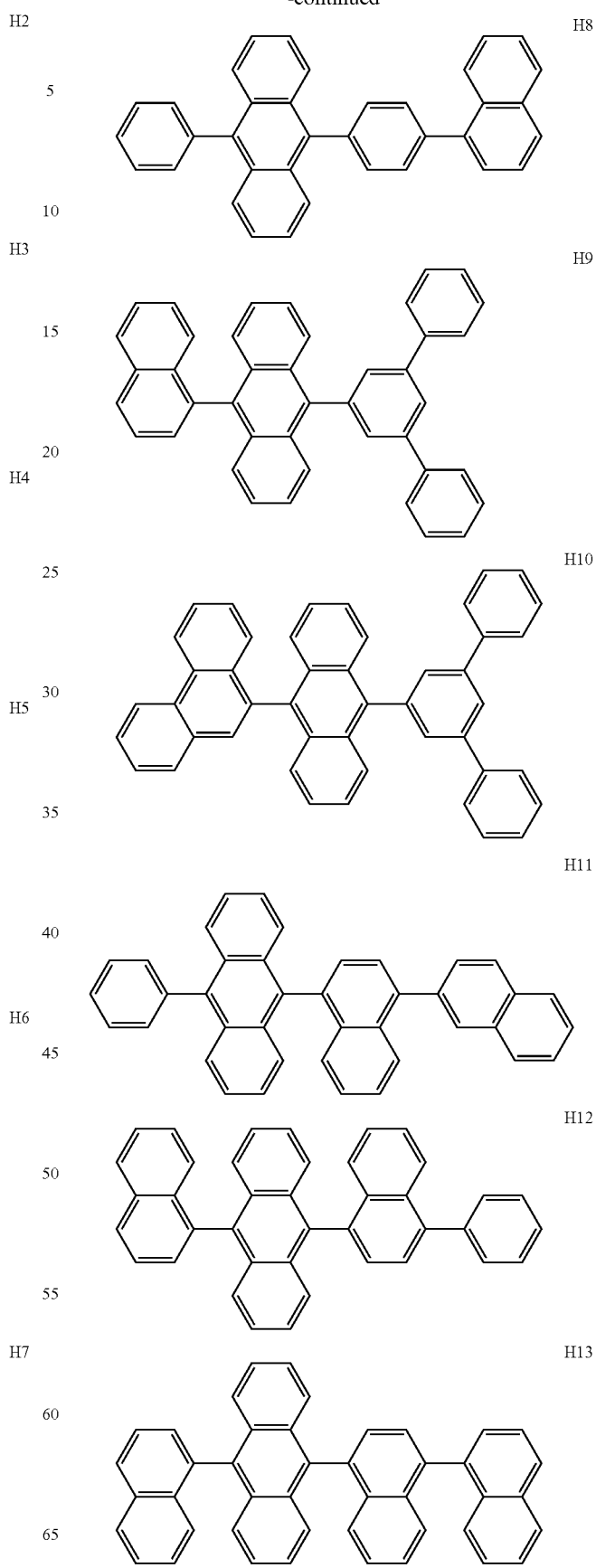

H14
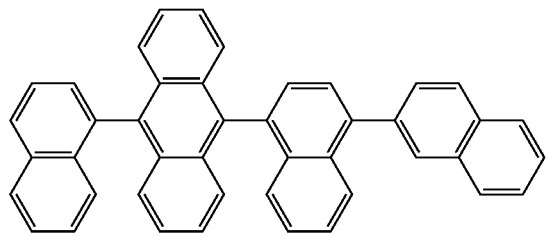
H15
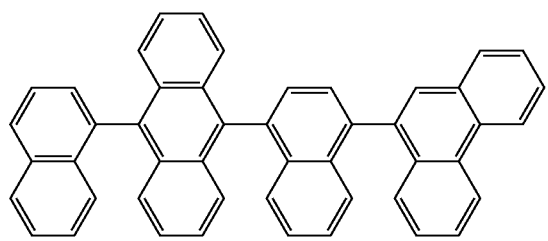
H16
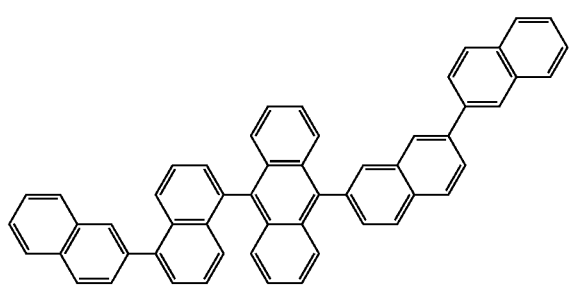
H17
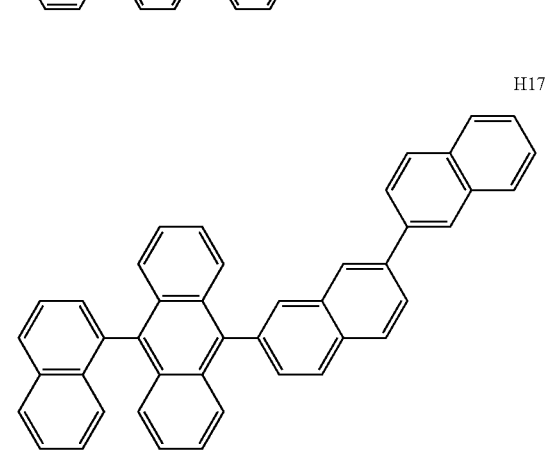
H18
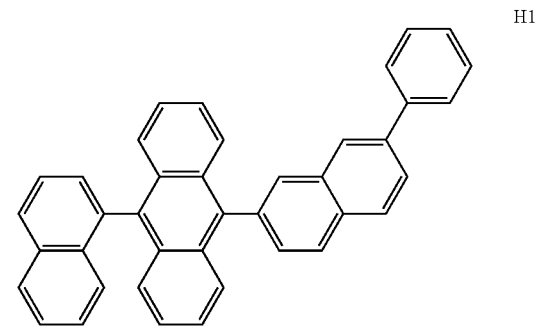
H19
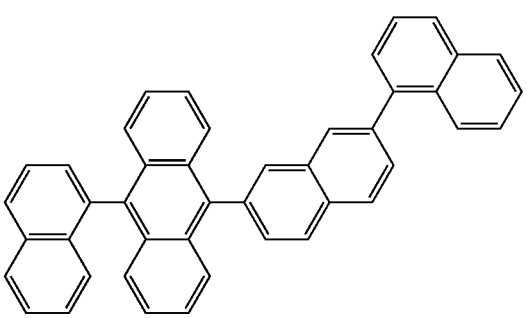
H20
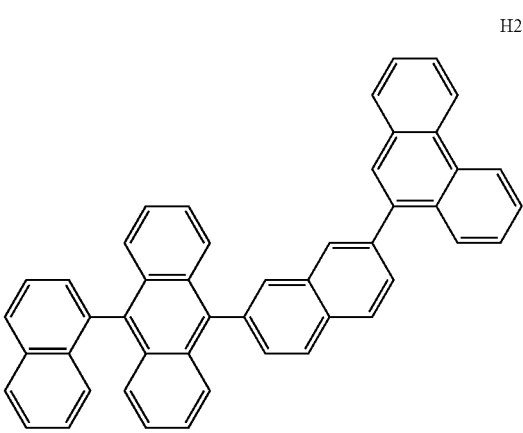
H21
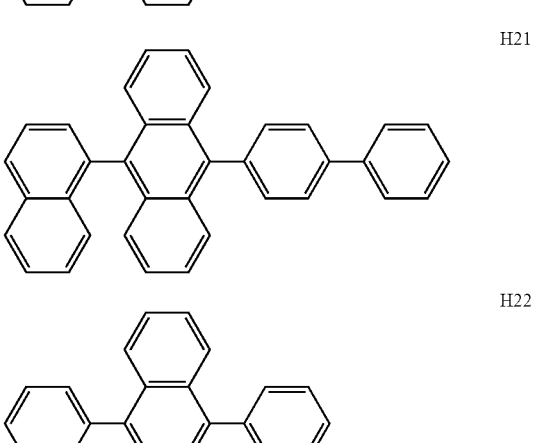
H22
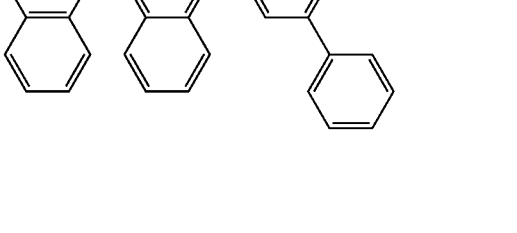
H23
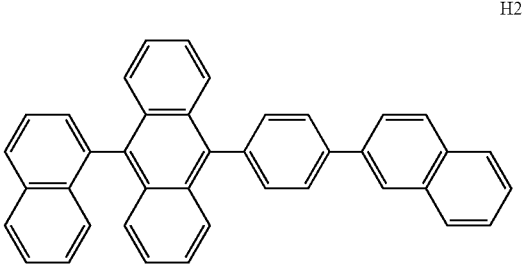

H24
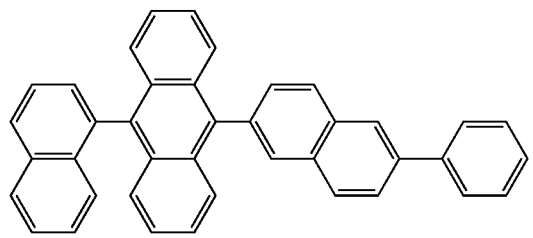
H25
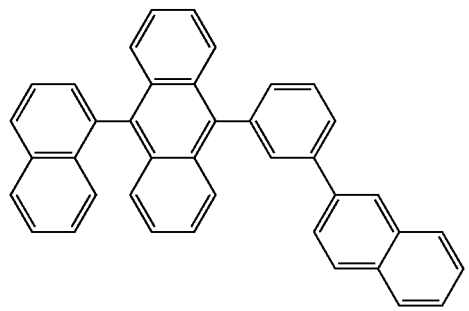
H26
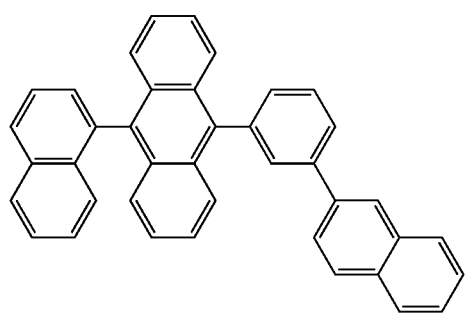
H27
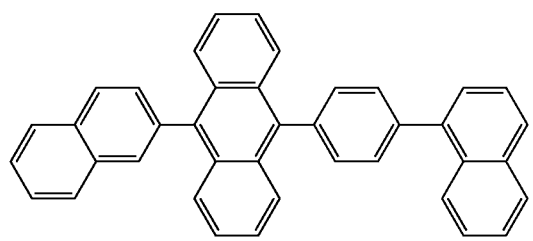
H28
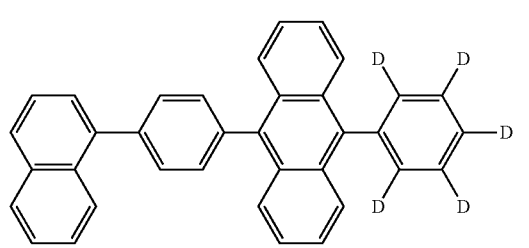
H29
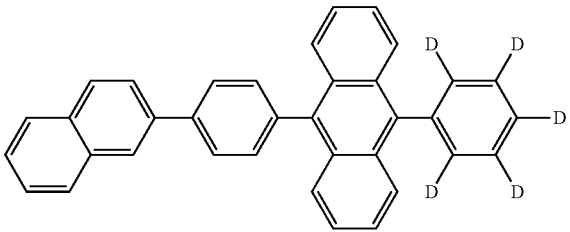
H30
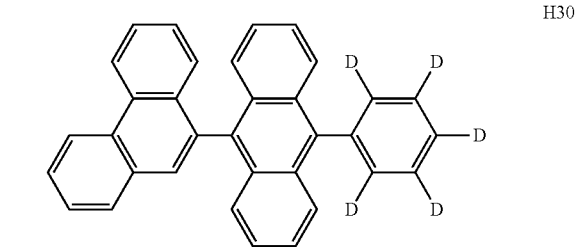
H31
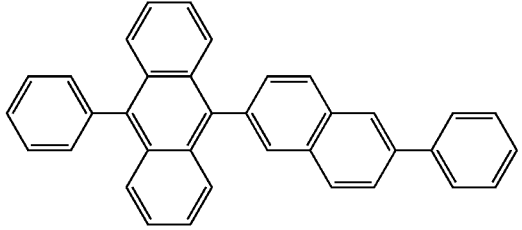
H32
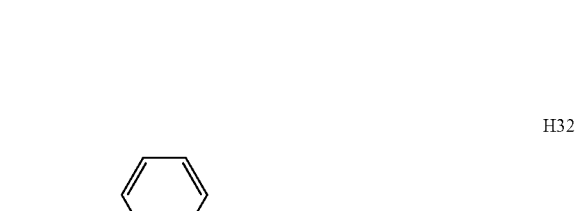
H33
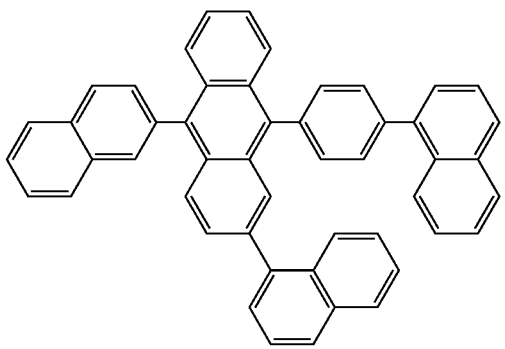

-continued
H34
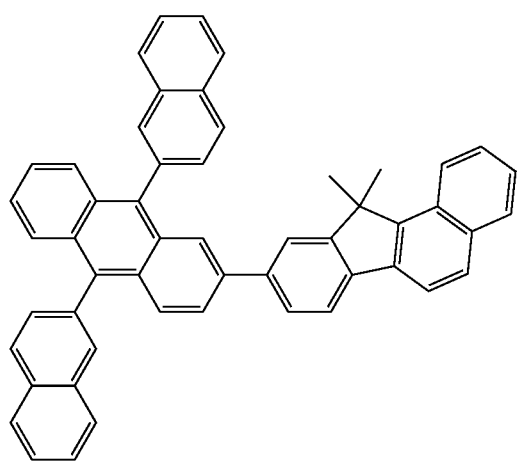
H35
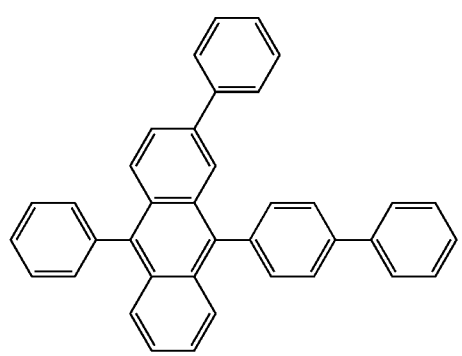
H36
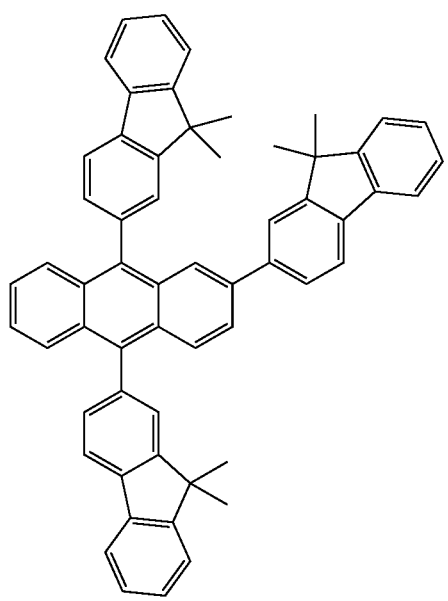
-continued
H37
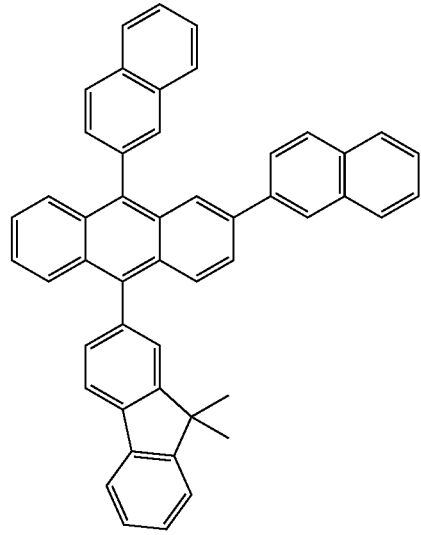
H38
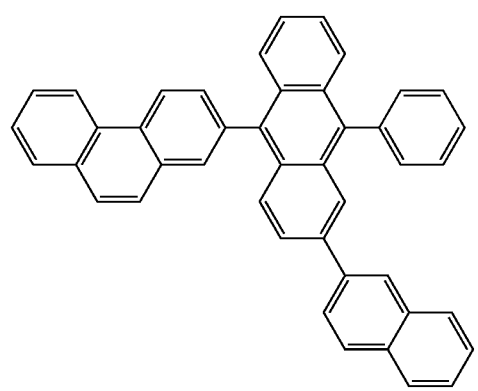
H39
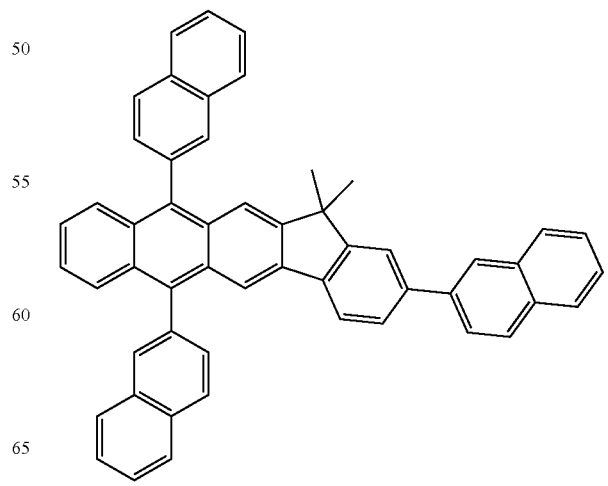

H40
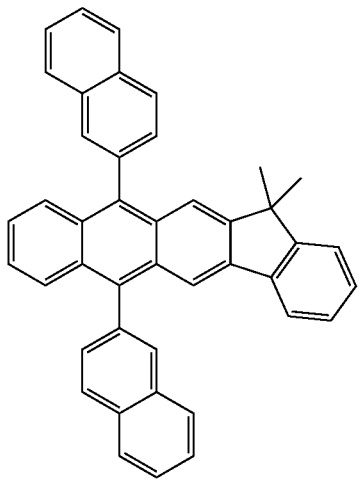
H41
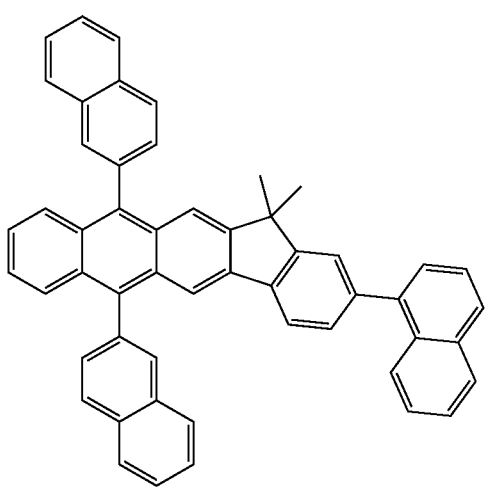
H42
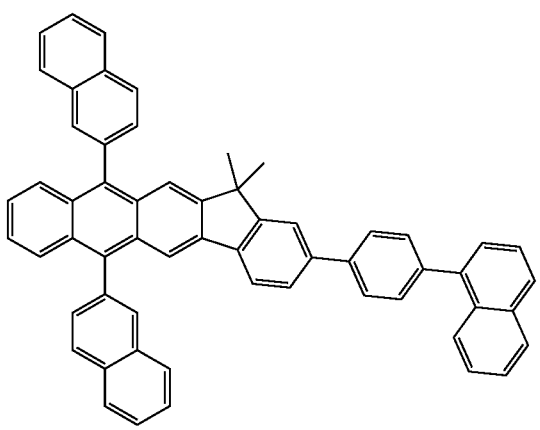
H43
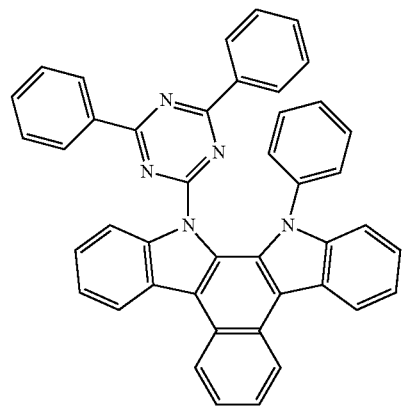
H44
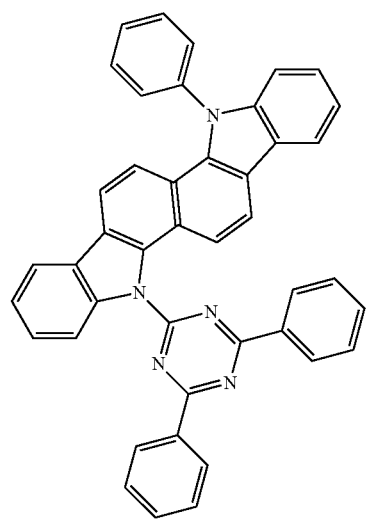
H45
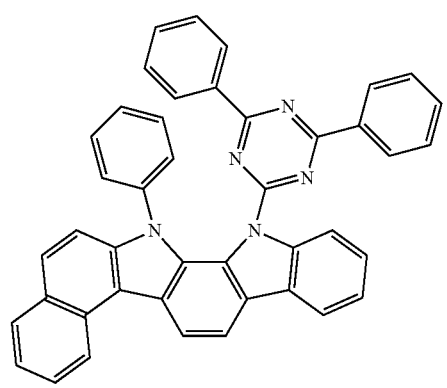
In some embodiments, the host may include at least one of Compounds H43 to H49 below.

71
-continued

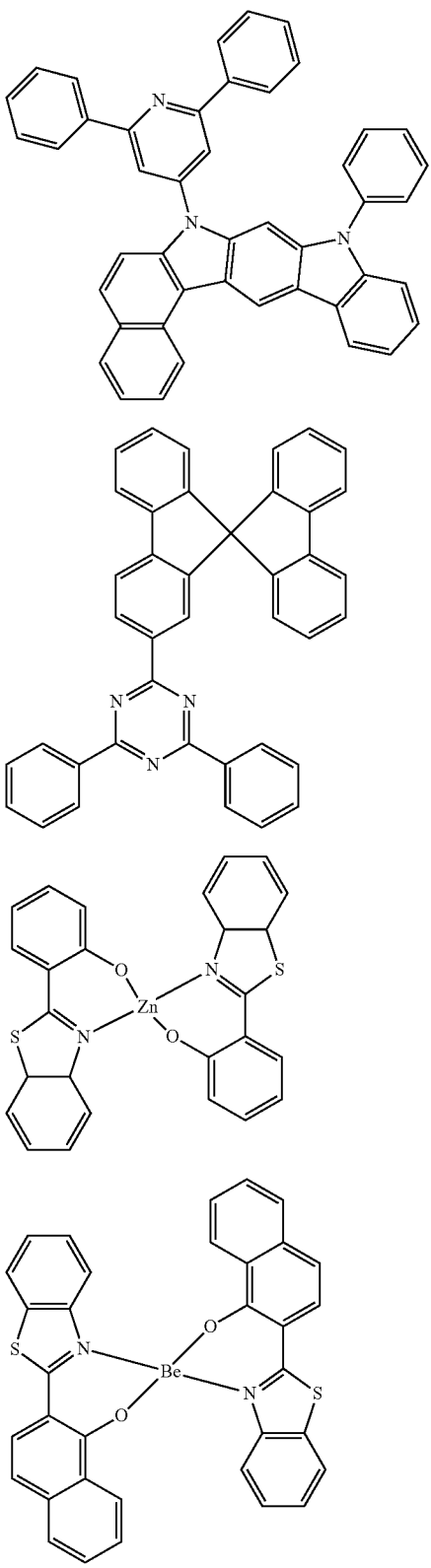

H46

H47

H48

H49

An amount of organometallic compound represented by Formula 1 (e.g., as a dopant) in the emission layer may be, e.g., in a range of about 0.01 to about 15 parts by weight based on 100 parts by weight of the host.

72

A thickness of the emission layer may be in a range of about 100 Å to about 1,000 Å, e.g., about 200 Å to about 600 Å. When the thickness of the emission layer is within this range, excellent light-emission characteristics may be obtained without a substantial increase in driving voltage.

Then, an electron transport region may be disposed on the emission layer.

The electron transport region may include at least one selected from a hole blocking layer, an electron transport layer (ETL), and an electron injection layer.

For example, the electron transport region may have a structure of electron transport layer/electron injection layer or a structure of hole blocking layer/electron transport layer/electron injection layer, wherein layers of each structure are sequentially stacked from the emission layer in the stated order.

In an implementation, the organic layer 150 of the organic light-emitting device may include an electron transport region disposed between the emission layer and the second electrode 190, and the electron transport region may include the organometallic compound represented by Formula 1.

The electron transport region may include a hole blocking layer. The hole blocking layer may be formed, when the emission layer includes a phosphorescent dopant, to prevent diffusion of excitons or holes into an electron transport layer.

When the electron transport region includes a hole blocking layer, the hole blocking layer may be formed on the emission layer by using various methods, such as vacuum deposition, spin coating casting, a LB method, ink-jet printing, laser-printing, or laser-induced thermal imaging. When the hole blocking layer is formed by vacuum deposition or spin coating, deposition and coating conditions for the hole blocking layer may be determined by referring to the deposition and coating conditions for the hole injection layer.

The hole blocking layer may include, for example, at least one of BCP and Bphen.

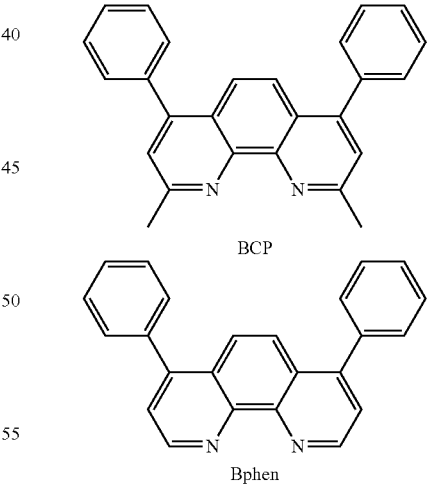

BCP

Bphen

A thickness of the hole blocking layer may be in a range of about 20 Å to about 1,000 Å, e.g., about 30 Å to about 300 Å. When the thickness of the hole blocking layer is within these ranges, the hole blocking layer may have improved hole blocking ability without a substantial increase in driving voltage.

The electron transport region may include an electron transport layer. The electron transport layer may be formed on the emission layer or the hole blocking layer by using various methods, e.g., vacuum deposition, spin coating casting, a LB method, ink-jet printing, laser-printing, or laser-induced thermal imaging. When an electron transport layer is formed by vacuum deposition or spin coating, deposition and coating conditions for the electron transport layer may be determined by referring to the deposition and coating conditions for the hole injection layer.

According to an embodiment, the organic layer 150 of the organic light-emitting device may include an electron transport region disposed between the emission layer and the second electrode 190. The electron transport region may include at least one selected from an electron transport layer and an electron injection layer.

The electron transport layer may further include at least one selected from BCP, Bphen, $Alq_3$, Balq, TAZ, and NTAZ.

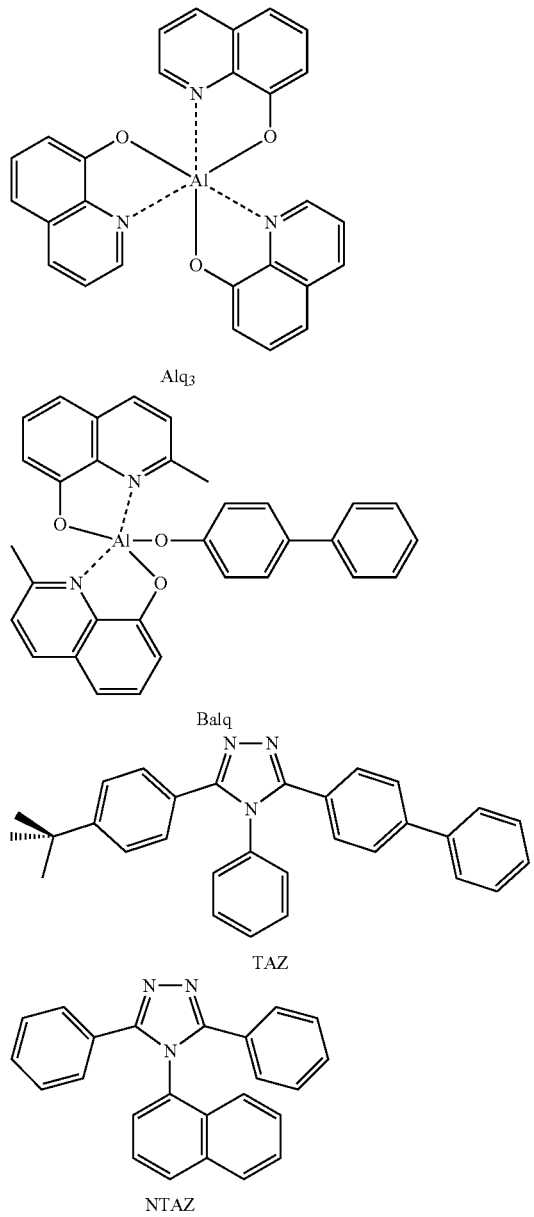

In some embodiments, the electron transport layer may include at least one compound selected from a compound represented by Formula 601 and a compound represented by Formula 602 illustrated below:

$$Ar_{601}\text{-}[(L_{601})_{xe1}\text{-}E_{601}]_{xe2} \quad <\text{Formula 601}>$$

wherein in Formula 601.

$Ar_{601}$ may be selected from a naphthalene, a heptalene, a fluorenene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene group, a heptalene group, a fluorenene group, a spiro-fluorene group, a benzofluorenene group, a dibenzofluorenene group, a phenalene group, a phenanthrene group, a anthracene group, a fluoranthene group, a triphenylene group, a pyrene group, a chrysene group, a naphthacene group, a picene group, a perylene group, a pentaphene group, and an indenoanthracene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ are each independently selected from a hydrogen, a $C_1$-$C_{60}$ alkyl group, a $C_2$-$C_{60}$ alkenyl group, a $C_2$-$C_{60}$ aryl group, and a $C_1$-$C_{60}$ heteroaryl group);

$L_{601}$ may be the same as explained in connection with $L_{201}$;

$E_{601}$ may be selected from a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a furinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, C1-C20 alkyl group, C1-C20 alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

xe1 may be selected from 0, 1, 2, and 3; and
xe2 may be selected from 1, 2, 3, and 4.

<Formula 602>

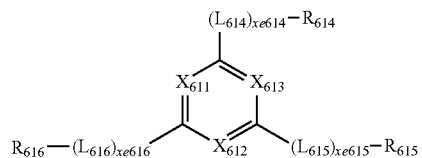

wherein in Formula 602, $X_{611}$ is N or C-$(L_{611})_{xe611}$-$R_{611}$, $X_{612}$ is N or C-$(L_{612})_{xe612}$-$R_{612}$, $X_{613}$ is N or C-$(L_{613})_{xe613}$-$R_{613}$ and, at least one of $X_{611}$ to $X_{613}$ is N;

$L_{611}$ to $L_{616}$ may be the same as explained in connection with $L_{201}$;

$R_{611}$ to $R_{616}$ are each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xe611 to xe616 may be each independently selected from 0, 1, 2, and 3.

The compound represented by Formula 601 and the compound represented by Formula 602 may be selected from Compounds ET1 to ET15 illustrated below.

ET1

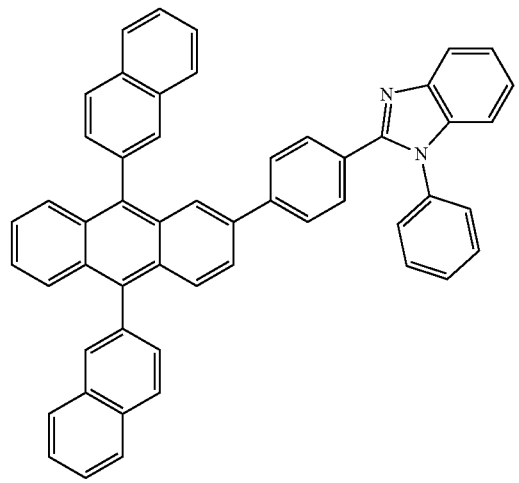

77
-continued
ET2
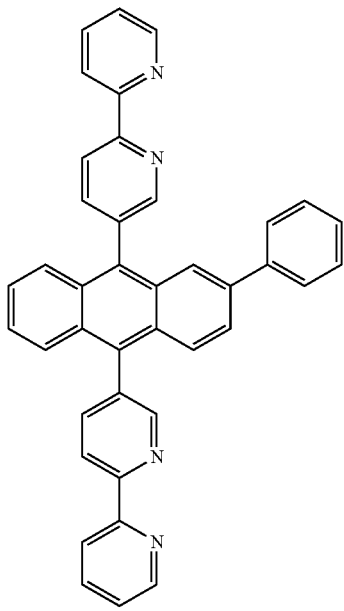
ET3
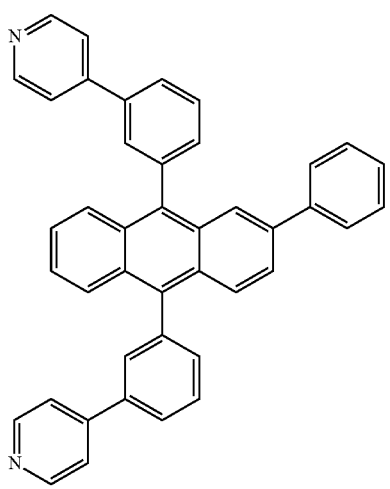
ET4
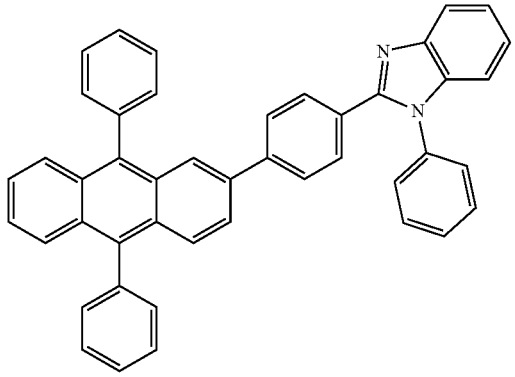
78
-continued
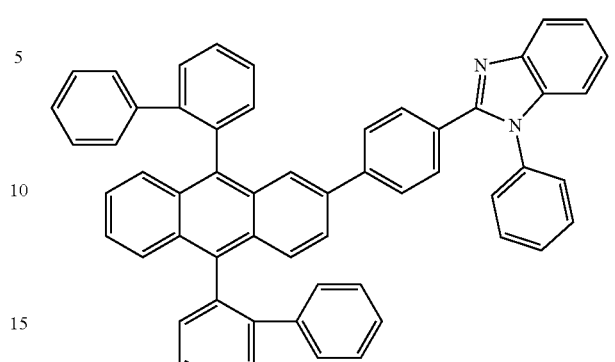

ET8
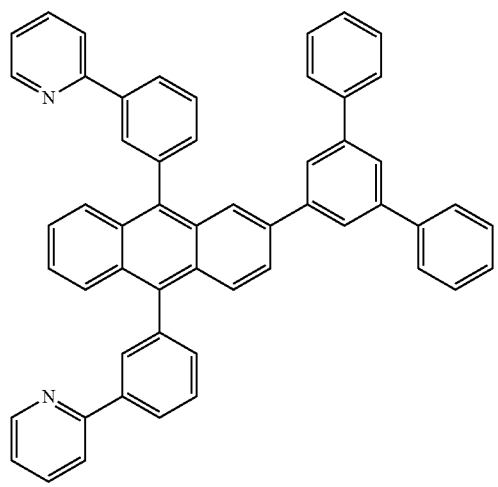
ET9
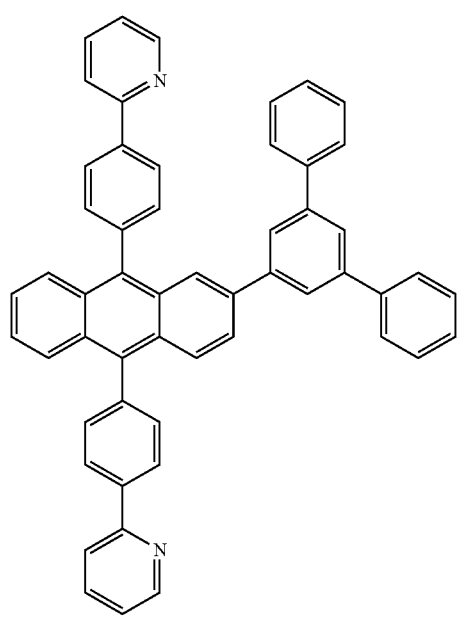
ET10
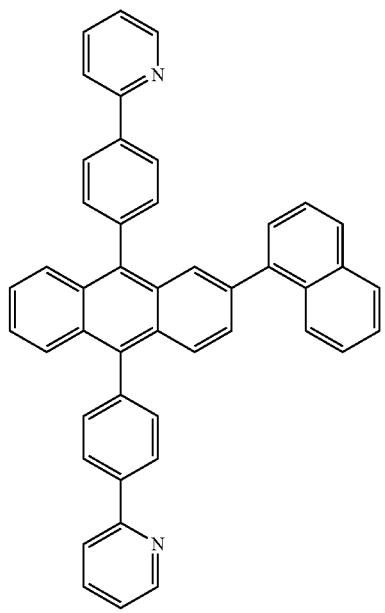
ET11
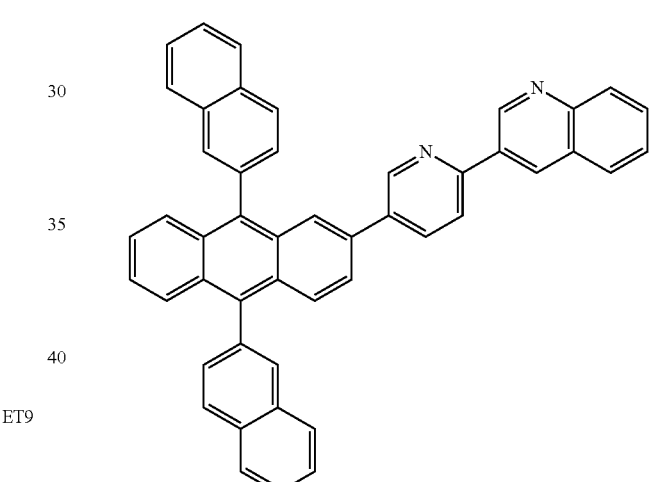
ET12
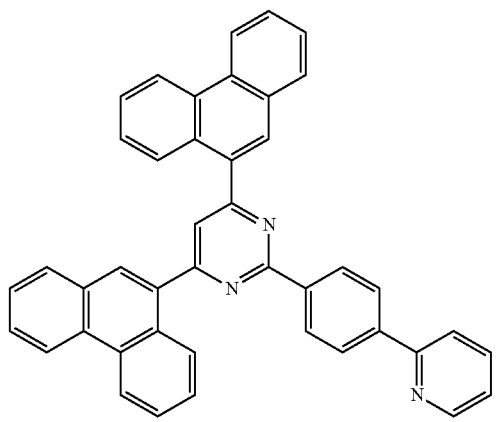

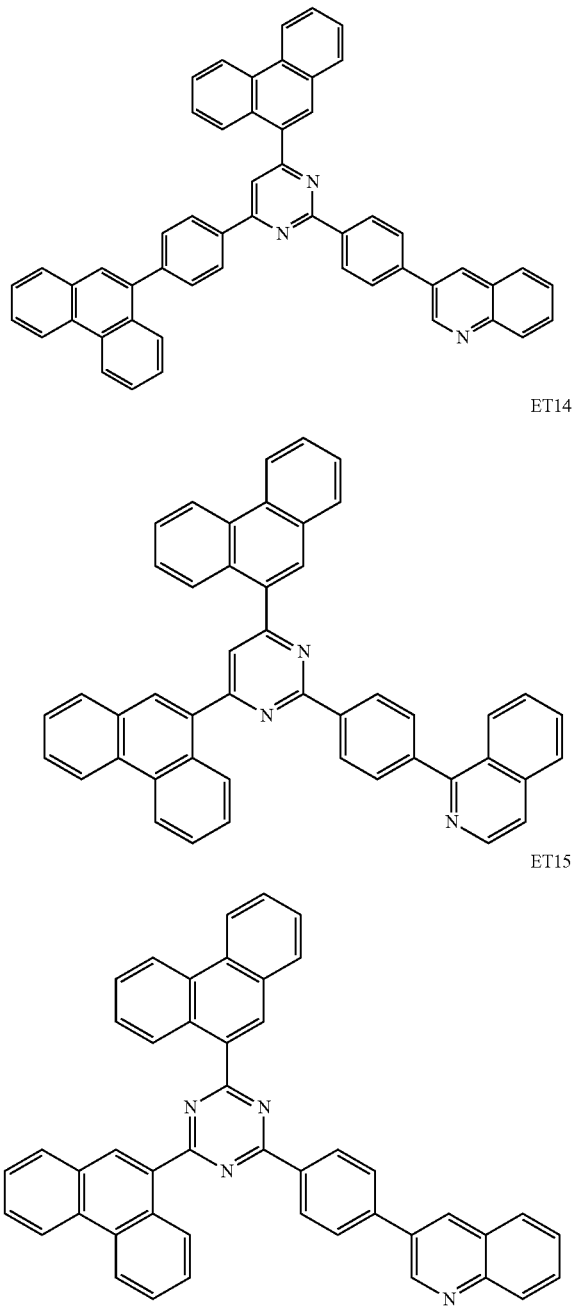

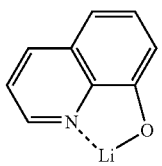

ET-D1

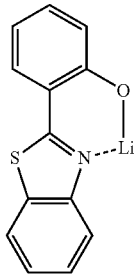

ET-D2

A thickness of the electron transport layer may be in a range of about 100 Å to about 1,000 Å, e.g., about 150 Å to about 500 Å. When the thickness of the electron transport layer is within the range described above, the electron transport layer may have satisfactory electron transport characteristics without a substantial increase in driving voltage.

In an implementation, the electron transport layer may further include, in addition to the materials described above, a metal-containing material.

The metal-containing material may include a Li complex. The Li complex may include, e.g., Compound ET-D1 (lithium quinolate, LiQ) or ET-D2.

The electron transport region may include an electron injection layer that allows electrons to be easily provided from the second electrode 190.

The electron injection layer may be formed on the electron transport layer by using various methods, e.g., vacuum deposition, spin coating casting, a LB method, ink-jet printing, laser-printing, or laser-induced thermal imaging. When an electron injection layer is formed by vacuum deposition or spin coating, deposition and coating conditions for the electron injection layer may be determined by referring to the deposition and coating conditions for the hole injection layer.

The electron injection layer may include at least one selected from, LiF, NaCl, CsF, $Li_2O$, BaO, and LiQ.

A thickness of the electron injection layer may be in a range of about 1 Å to about 100 Å, e.g., about 3 Å to about 90 Å. When the thickness of the electron injection layer is within the range described above, the electron injection layer may have satisfactory electron injection characteristics without a substantial increase in driving voltage.

The second electrode 190 is disposed on the organic layer 150 having such a structure. The second electrode 190 may be a cathode that is an electron injection electrode, and in this regard, a material for forming the second electrode 190 may be a material having a low work function. Such a material may include a metal, alloy, an electrically conductive compound, or a mixture thereof. Examples of the material for the second electrode 190 may include lithium (Li), magnesium (Mg), aluminum (Al), aluminum-lithium (Al—Li), calcium (Ca), magnesium-indium (Mg—In), or magnesium-silver (Mg—Ag). In some embodiments, the material for forming the second electrode 190 may be ITO or IZO. The second electrode 190 may be a reflective electrode, a semi-transmissive electrode, or a transmissive electrode.

Hereinbefore, the organic light-emitting device has been described with reference to FIG. 1.

A $C_1$-$C_{60}$ alkyl group used herein refers to a linear or branched aliphatic hydrocarbon monovalent group having 1 to 60 carbon atoms, and detailed examples thereof are a methyl group, an ethyl group, a propyl group, an isobutyl group, a sec-butyl group, a ter-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group), and detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or at the terminal of the $C_2$-$C_{60}$ alkyl group, and detailed examples thereof are an ethenyl group, a prophenyl group, and a butenyl group. A $C_2$-$C_{60}$ alkylene group used herein refers to a divalent group having the same structure as the $C_2$-$C_{60}$ alkyl group.

A $C_2$-$C_{60}$ alkynyl group used herein refers to a hydrocarbon group formed by substituting at least one carbon trip bond in the middle or at the terminal of the $C_2$-$C_{60}$ alkyl group, and detailed examples thereof are an ethynyl group, and a propynyl group. A $C_2$-$C_{60}$ alkylene group used herein refers to a divalent group having the same structure as the $C_2$-$C_{60}$ alkyl group.

A $C_3$-$C_{10}$ cycloalkyl group used herein refers to a monovalent hydrocarbon monocyclic group having 3 to 10 carbon atoms, and detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_1$-$C_{10}$ heterocycloalkyl group used herein refers to a monovalent monocyclic group having at least one hetero atom selected from N, O, P, and S as a ring-forming atom and 1 to 10 carbon atoms, and detailed examples thereof are a tetrahydrofuranyl group, and a tetrahydrothiophenyl group. A $C_1$-$C_{10}$ heterocycloalkylene group used herein refers to a divalent group having the same structure as the $C_1$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromacity, and detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_1$-$C_{10}$ heterocycloalkenyl group used herein refers to a monovalent monocyclic group that has at least one hetero atom selected from N, O, P, and S as a ring-forming atom, 1 to 10 carbon atoms, and at least one double bond in its ring. Detailed examples of the $C_1$-$C_{10}$ heterocycloalkenyl group are a 2,3-hydrofuranyl group and a 2,3-hydrothiophenyl group. A $C_1$-$C_{10}$ heterocycloalkenylene group used herein refers to a divalent group having the same structure as the $C_1$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

A $C_1$-$C_{60}$ heteroaryl group used herein refers to a monovalent group having a carboncyclic aromatic system that has at least one hetero atom selected from N, O, P, and S as a ring-forming atom, and 1 to 60 carbon atoms. A $C_1$-$C_{60}$ heteroarylene group used herein refers to a divalent group having a carbocyclic aromatic system that has at least one hetero atom selected from N, O, P, and S as a ring-forming atom, and 1 to 60 carbon atoms. Examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

A monovalent non-aromatic condensed polycyclic group used herein refers to a monovalent group (for example, having 8 to 60 carbon atoms) that has two or more rings condensed to each other, only carbon atoms as a ring forming atom, and non-aromacity in the entire molecular structure. A detailed example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group used herein refers to a monovalent group (for example, having 2 to 60 carbon atoms) that has two or more rings condensed to each other, has a heteroatom selected from N, O P, and S, other than carbon atoms, as a ring forming atom, and has non-aromacity in the entire molecular structure. An example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

at least one substituent of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, or a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), —B($Q_{16}$)($Q_{17}$), and —C(=O)($Q_{18}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, or a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), —B($Q_{26}$)($Q_{27}$), and —C(=O)($Q_{28}$); and —N($Q_{31}$)($Q_{32}$), —Si($Q_{33}$)($Q_{34}$)($Q_{35}$), —B($Q_{36}$)($Q_{37}$), and —C(=O)($Q_{38}$);

wherein $Q_1$ to $Q_8$, $Q_{11}$ to $Q_{18}$, $Q_{21}$ to $Q_{28}$, and $Q_{31}$ to $Q_{38}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arythio group, a $C_1$-$C_{60}$ heteroaryl group, a monovalent non-aromatic condensed polycyclic group, or a monovalent non-aromatic condensed heteropolycyclic group.

For example, at least one substituent of substituents of the substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted divalent non-aromatic condensed polycyclic group, substituted divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{11}$)($Q_{12}$), —Si($Q_{13}$)($Q_{14}$)($Q_{15}$), —B($Q_{16}$)($Q_{17}$), and —C(=O)($Q_{16}$);

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group;

a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, —N($Q_{21}$)($Q_{22}$), —Si($Q_{23}$)($Q_{24}$)($Q_{25}$), —B($Q_{26}$)($Q_{27}$), and —C(=O)($Q_{26}$); and —N($Q_{31}$)($Q_{32}$), —Si($Q_{33}$)($Q_{34}$)($Q_{35}$), —B($Q_{36}$)($Q_{37}$), and —C(=O)($Q_{36}$);

wherein $Q_{11}$ to $Q_{18}$, $Q_{21}$ to $Q_{28}$, and $Q_{31}$ to $Q_{38}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, and an imidazopyrimidinyl group.

Hereinafter, an organic light-emitting device according to an embodiment is described in detail with reference to Synthesis Example and Examples. The wording "B was used instead of A" used in describing Synthesis Examples means that a molar equivalent of A was identical to a molar equivalent of B.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

EXAMPLE

Synthesis Example 1

Synthesis of Compound 1

Synthesis of Intermediate 1

Intermediate 1 was synthesized according to Reaction Scheme 1-1 below:

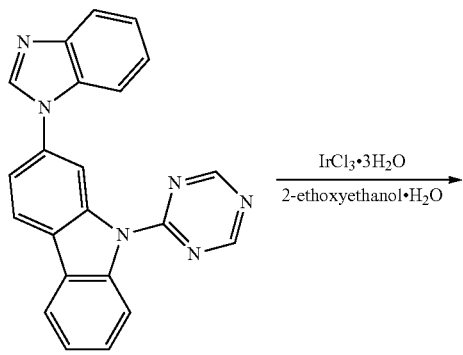

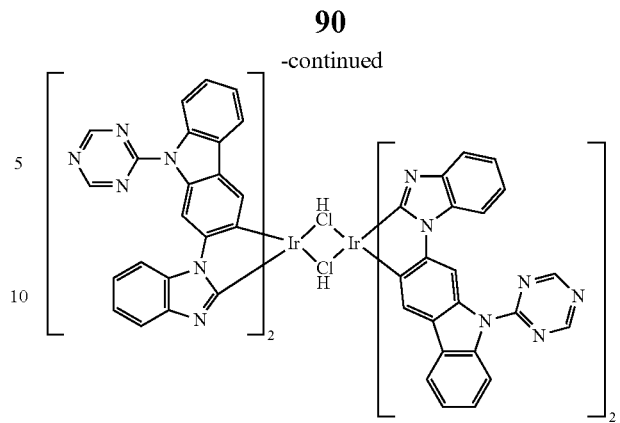

6.26 g (17.3 mmol) of 3-((1H-benzo[d]imidazole-1-yl)methyl)-9-(1,3,5-triazine-2-yl)-9H-carbazole was dissolved in 45 mL of 2-ethoxyethanol, and then, 2.4 g (7.6 mmol) of iridium chloride hydrate ($IrCl_3 \cdot 3H_2O$) and 15 mL of distilled water were added thereto, and the result was stirred at a temperature of 130° C. for 20 hours. Once the reaction was complete, the reaction solution was cooled to ambient temperature and a precipitate was filtered therefrom. The precipitate was washed with methanol and dried in a vacuum condition to produce.

Synthesis of Compound 1

Compound 1 was Synthesized According to Reaction Scheme 1-2 Below:

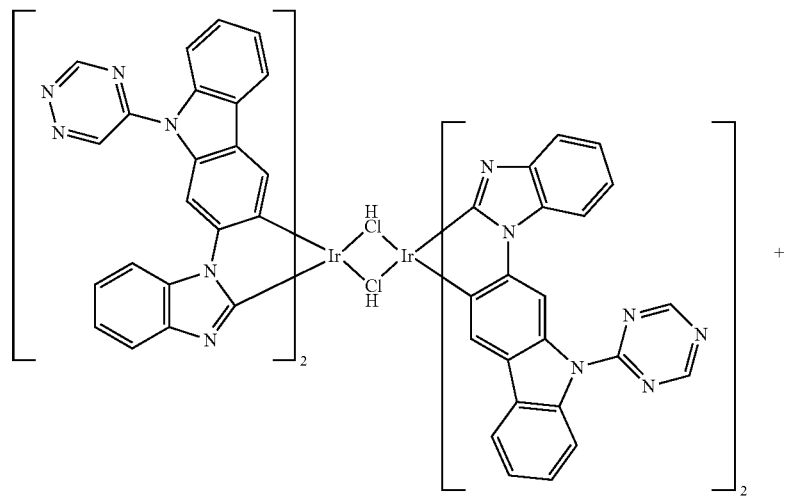

-continued

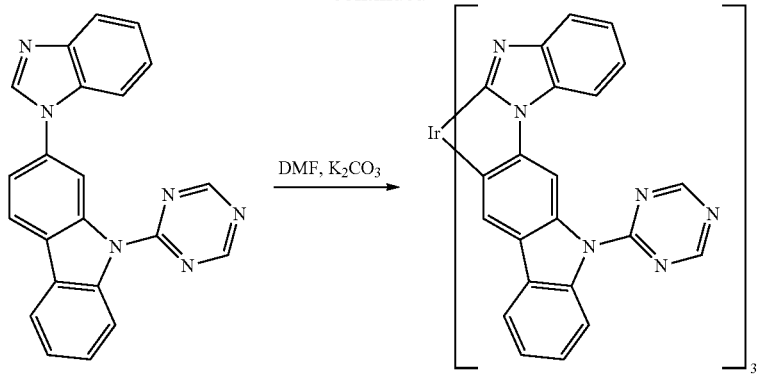

5.37 g (4.56 mmol) of Intermediate 1 obtained through Reaction Scheme 1-1, 4.12 g (11.4 mmol) of 3-((1H-benzo[d]imidazole-1-yl)methyl)-9-(1,3,5-triazine-2-yl)-9H-carbazole, and 0.5 g of $K_2CO_3$ were added to 30 mL of 2-ethoxyethanol, and then, the mixture was stirred at a temperature of 130° C. for 12 hours. Once the reaction was complete, the reaction solution was cooled to ambient temperature (25° C.) and a precipitate was filtered therefrom and washed with methanol. The precipitate was dissolved by using dichloromethane and then filtered through a silica short pad, and the filtered dichloromethane solution was boiled and methanol was slowly added thereto to precipitate 3.20 g (yield: 55%) of Compound 1.

$^1$H-NMR: 8.86 (6H), 8.55 (3H), 8.10 (1H), 7.95 (3H), 7.63 (3H), 7.59 (3H), 7.49 (3H) 7.29 (3H) 7.20 (6H)

APCI-MS (m/z): 1278[M+]

Synthesis Example 2

Synthesis of Compound 2

Synthesis of Intermediate 2

6.26 g (17.3 mmol) of 3-((1H-benzo[d]imidazole-1-yl)methyl)-9-(1,3,5-triazine-2-yl)-9H-carbazole was dissolved in 45 mL of 2-ethoxyethanol, and then, 2.4 g(7.6 mmol) of iridium chloride hydrate ($IrCl_3 \cdot 3H_2O$) and 15 mL of distilled water were added thereto, and the result was stirred at a temperature of 130° C. for 20 hours. When the reaction was complete, the reaction solution was cooled to ambient temperature. A precipitate was filtered therefrom and washed with methanol and dried in a vacuum condition to produce 5.37 g (yield: 60%) of Intermediate 2 that is a dimer.

Synthesis of Compound 2

5.37 g (4.56 mmol) of Intermediate 2, 1.76 g (11.4 mmol) of 2-phenyla pyridine, and 0.5 g of $K_2CO_3$ were added to 30 mL, of 2-ethoxyethanol, and then, the result was stirred at a temperature of 130° C. for 12 hours. Once the reaction was complete, the reaction solution was cooled to ambient temperature (25° C.) and a precipitate was filtered therefrom and washed with methanol. The precipitate was dissolved by using dichloromethane, and then filtered through a silica short pad, and the filtered dichloromethane solution was boiled, and methanol was slowly added thereto to produce 2.93 g (yield: 60%) of Compound 2.

$^1$H-NMR: 8.87 (4H), 8.56 (3H), 8.30 (1H), 8.12 (2H), 7.98 (3H), 7.83 (2H), 7.63 (2H), 7.59 (2H), 7.54 (2H), 7.51 (2H), 7.22 (6H), 7.00 (2H)

APCI-MS (m/z): 1071 [M+]

Synthesis Example 3

Synthesis of Compound 3

Synthesis of Intermediate 3

6.26 g (17.3 mmol) of 3-((1H-benzo[d]imidazole-1-yl)methyl)-9-(1,3,5-triazine-2-yl)-9H-carbazole was dissolved in 45 mL of 2-ethoxyethanol, and then, 2.4 g(7.6 mmol) of iridium chloride hydrate ($IrCl_3 \cdot 3H_2O$) and 15 mL of distilled water were added thereto, and the result was stirred at a temperature of 130° C. for 20 hours. Once the reaction was complete, the reaction solution was cooled to ambient temperature, and a precipitate was filtered therefrom and washed by using methanol and dried in a vacuum condition to produce 5.37 g(yield: 60%) of Intermediate 3 that is a dimer.

Synthesis of Compound 3

5.37 g (4.56 mmol) of Intermediate 3, 2.17 g (11.4 mmol) of 2-(2,4-difluorophenyl)pyridine, and 0.5 g of $K_2CO_3$ were added to 30 mL of 2-ethoxyethanol, and then, the result was stirred at a temperature of 130° C. for 12 hours. Once the reaction was complete, the reaction solution was cooled to ambient temperature (25° C.) and a precipitate was filtered therefrom and washed with methanol. The precipitate was dissolved by using dichloromethane and filtered through a silica short pad, and the filtered dichloromethane solution was boiled and methanol was slowly added thereto to produce 2.92 g (yield: 58%) of Compound 3.

$^1$H-NMR: 8.87 (4H), 8.56 (3H), 8.12 (2H), 7.98 (3H), 7.83 (2H), 7.63 (2H), 7.59 (2H), 7.51 (3H), 7.22 (6H), 7.00 (3H)

APCI-MS (m/z): 1105[M+]

Synthesis Example 4

Synthesis of Compound 5

Synthesis of Intermediate 4

6.26 g (17.3 mmol) of 3-((1H-benzo[d]imidazole-1-yl)methyl)-9-(1,3,5-triazine-2-yl)-9H-carbazole was dissolved in 45 mL of 2-ethoxyethanol, and then, 2.4 g(7.6 mmol) of iridium chloride hydrate ($IrCl_3 \cdot 3H_2O$) and 15 mL of distilled water were added thereto, and the result was stirred at a temperature of 130° C. for 20 hours. Once the reaction was complete, the reaction solution was cooled to ambient temperature, and a precipitate was filtered therefrom and washed by using methanol and dried in a vacuum condition to produce 5.37 g(yield: 60%) of Intermediate 4 that is a dimer.

Synthesis of Compound 5

5.37 g (4.56 mmol) of Intermediate 4, 2.54 g (11.4 mmol) of 2-(2,4-dicyano-3-fluorophenyl)pyridine, and 0.5 g of K$_2$CO$_3$ were added to 30 mL of 2-ethoxyethanol, and then, the result was stirred at a temperature of 130° C. for 12 hours. Once the reaction was complete, the reaction solution was cooled to ambient temperature (25° C.) and a precipitate was filtered therefrom and washed with methanol. The precipitate was dissolved by using dichloromethane and then filtered through a silica short pad, and the filtered dichloromethane solution was boiled and methanol was slowly added thereto to precipitate 2.85 g (yield: 55%) of Compound 5.

$^1$H-NMR: 8.87 (4H), 8.56 (3H), 8.12 (2H), 8.04 (1H) 7.98 (4H), 7.83 (2H), 7.63 (2H), 7.59 (2H), 7.51 (3H), 7.22 (6H), 7.00 (1H)

APCI-MS (m/z): 1136[M+]

Example 1

An ITO glass substrate (a product of Corning Co., Ltd) having a sheet resistance of 15 Ω/cm$^2$ and a thickness of 500 Å as an anode was cut to a size of 50 mm×50 mm×0.7 mm, and then, sonicated by using isopropyl alcohol and pure water each for 5 minutes, and cleaned by the exposure to ultraviolet rays for 30 minutes, and then ozone, and the ITO glass substrate was mounted on a vacuum deposition apparatus.

2-TNATA was vacuum deposited on the ITO glass substrate to form a hole injection layer having a thickness of 600 Å, and then, NPB was vacuum deposited on the hole injection layer to form a hole transport layer having a thickness of 300 Å. Then, Compound 100 (host) and Compound 1 (dopant) were co-deposited at a weight ratio of 95:5 on the hole transport layer layer to form an emission layer having a thickness of 300 Å.

Then. Compound ET1 was deposited on the emission layer to form an electron transport layer having a thickness of 300 Å, and LiF was deposited on the electron transport layer to form an electron injection layer having a thickness of 10 Å, and Al was deposited on the electron injection layer to form a cathode having a thickness of 1,000 Å, thereby completing the manufacture of an organic light-emitting device.

Compound 100

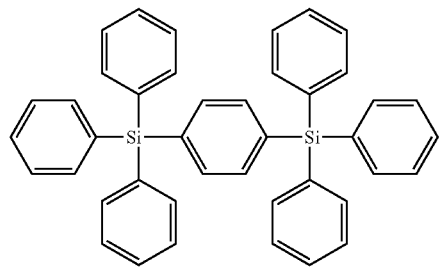

ET1

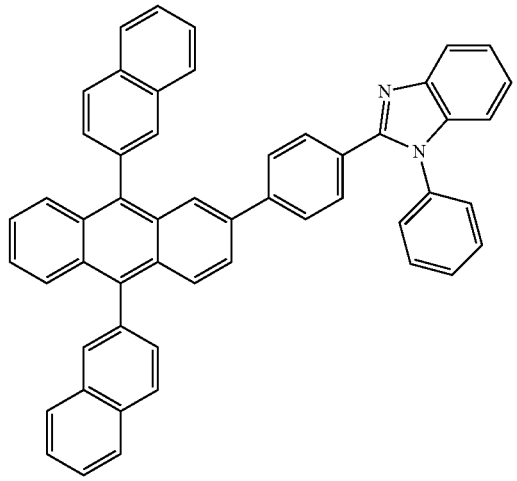

Example 2

An organic light-emitting device was manufactured in the same manner as in Example 1, except that in forming the emission layer, as a dopant, Compound 2 was used instead of Compound 1.

Example 3

An organic light-emitting device was manufactured in the same manner as in Example 1, except that in forming the emission layer, as a dopant, Compound 3 was used instead of Compound 1.

Example 4

An organic light-emitting device was manufactured in the same manner as in Example 1, except that in forming the emission layer, as a dopant, Compound 5 was used instead of Compound 1.

Example 5

An organic light-emitting device was manufactured in the same manner as in Example 1, except that in forming the emission layer, as a dopant, Compound 7 was used instead of Compound 1.

Comparative Example 1

An organic light-emitting device was manufactured in the same manner as in Example 1, except that in forming the emission layer, as a dopant, Compound A was used instead of Compound 1.

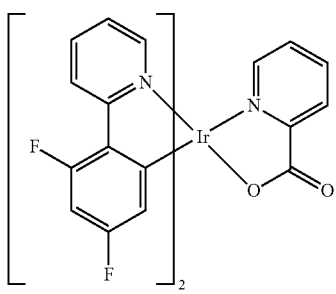

<Compound A>

Comparative Example 2

An organic light-emitting device was manufactured in the same manner as in Example 1, except that in forming the emission layer, as a dopant, Compound B was used instead of Compound 1.

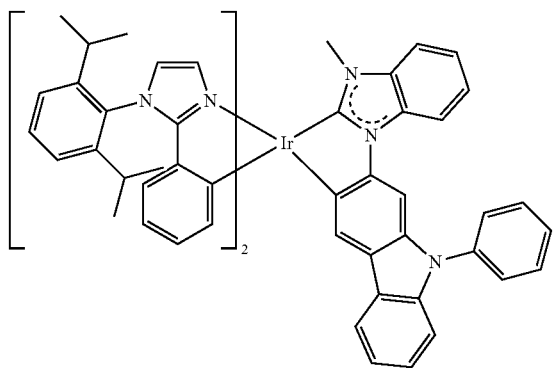

<Compound B>

Evaluation Example 1

The driving voltage and luminescent efficiency (at a current density of 10 mA/cm$^2$) of the organic light-emitting devices manufactured according to Examples 1-5 and Comparative Examples 1 and 2 were measured by using a PR650 Spectroscan Source Measurement Unit. (a product of PhotoResearch Inc.)

TABLE 1

|  | Emission layer dopant | Driving voltage (V) | Efficiency (cd/A) | Emission color |
|---|---|---|---|---|
| Example 1 | Compound 1 | 4.3 | 22.9 | Blue |
| Example 2 | Compound 2 | 4.5 | 21.8 | Blue |
| Example 3 | Compound 3 | 4.6 | 18.3 | Blue |
| Example 4 | Compound 5 | 4.4 | 17.2 | Blue |
| Example 5 | Compound 7 | 4.5 | 19.6 | Blue |
| Comparative Example 1 | Compound A | 4.7 | 15.4 | Blue |
| Comparative Example 2 | Compound B | 4.8 | 13.2 | Blue |

From Table 1, it may be that the driving voltage and luminescent efficiency of the organic light-emitting devices manufactured according to Examples 1 to 5 are higher than the driving voltage and luminescent efficiency of the organic light-emitting devices manufactured according to Comparative Examples 1 and 2.

An organic light-emitting device including the organometallic compound according to an embodiment may have a low driving voltage, high efficiency, high brightness, and a long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. An organometallic compound represented by the following Formula 1:

$$M(L_1)_{n1}(L_2)_{n2}$$ <Formula 1> wherein in Formula 1,

M is selected from iridium (Ir), platinum (Pt), osmium (Os), titanium (Ti), zirconium (Zr), hafnium (Hf), europium (Eu), terbium (Tb), thulium (Tm), and rhodium (Rh);

n1 is 0, 1, 2, or 4;

n2 is 1, 2, or 3;

when n1 is two or more, two or more $L_1$ are identical or different, and when n2 is two or more, two or more $L_2$ are identical or different;

$L_1$ is selected from a monovalent organic ligand, a divalent organic ligand, a trivalent organic ligand, and a tetravalent organic ligand, and is different from $L_2$;

$L_2$ is a ligand represented by the following Formula 2;

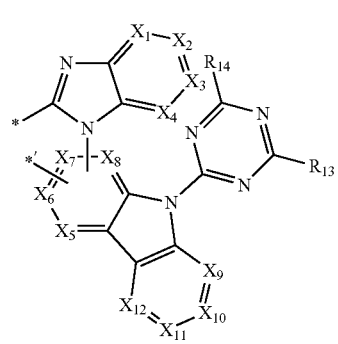

<Formula 2> wherein in Formula 2, $X_1$ is N or $C(R_1)$, $X_2$ is N or $C(R_2)$, $X_3$ is N or $C(R_3)$, and $X_4$ is N or $C(R_4)$;

$X_5$ is N, C, or $C(R_5)$, $X_6$ is N, C, or $C(R_6)$, $X_7$ is N, C, or $C(R_7)$, $X_8$ is N, C, or $C(R_8)$, and two of $X_5$ to $X_8$ are C, when $X_5$ is C, $X_5$ binds to M or N of a benzimidazole-based moiety in Formula 2; when $X_6$ is C, $X_6$ binds to M or N of the benzimidazole-based moiety in Formula 2; when $X_7$ is C, $X_7$ binds to M or N of the benzimidazole-based moiety in Formula 2; when $X_8$ is C, $X_8$ binds to M or N of the benzimidazole-based moiety in Formula 2;

$X_9$ is N or $C(R_9)$, $X_{10}$ is N or $C(R_{10})$, $X_{11}$ is N or $C(R_{11})$, $X_{12}$ is N or $C(R_{12})$;

$R_1$ to $R_{12}$ are each independently selected from:

a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group;

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group, each substituted with at least one selected from —F, a cyano group, a nitro group, a phenyl group, a naphthyl group, a pyridinyl group, a pyrimidinyl group, a triazinyl group, and —$Si(Q_{33})(Q_{34})(Q_{35})$; and —$Si(Q_3)(Q_4)(Q_5)$, wherein $Q_3$ to $Q_5$ are each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group;

$R_{13}$ and $R_{14}$ are each independently a hydrogen or a phenyl group;

$R_1$ to $R_4$ are separate or two of $R_1$ to $R_4$ bind to each other to form a saturated or unsaturated ring, $R_9$ to $R_{12}$ are separate or two of $R_9$ to $R_{12}$ bind to each other to form a saturated or unsaturated ring, $R_{13}$ and $R_{14}$ are separate or $R_{13}$ and $R_{14}$ bind to each other to form a saturated or unsaturated ring;

* and *' each indicate a binding site to M in Formula 1.

2. The organometallic compound as claimed in claim 1, wherein:

M is iridium (Ir), n1 is 0, 1, or 2, n2 is 1, 2, or 3, and a sum of n1 and n2 is 3; or M is platinum (Pt), n1 is 0, 1, or 2, n2 is 1 or 2, and a sum of n1 and n2 is 2.

3. The organometallic compound as claimed in claim 1, wherein $L_2$ in Formula 1 is a ligand represented by one of the following Formulae 2A to 2F:

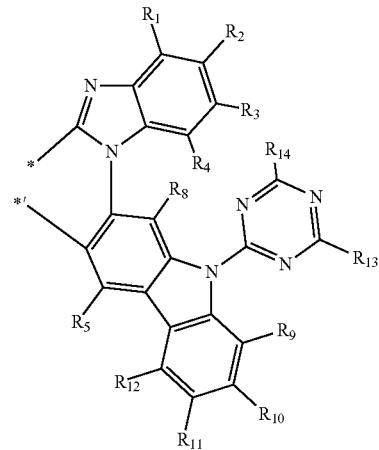

<Formula 2A>

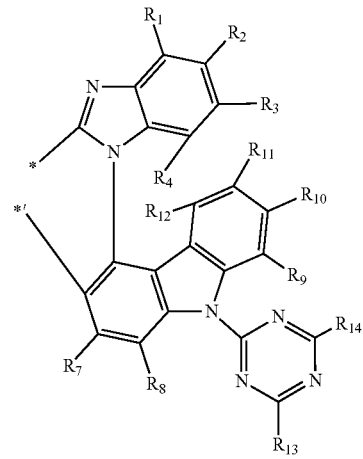

<Formula 2B>

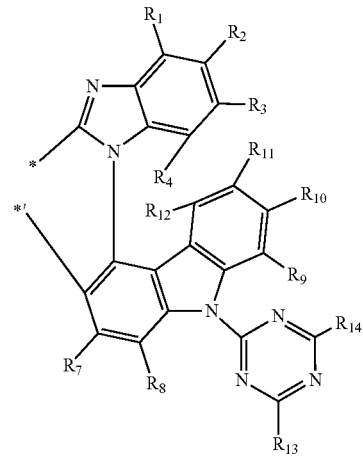

<Formula 2C>

-continued

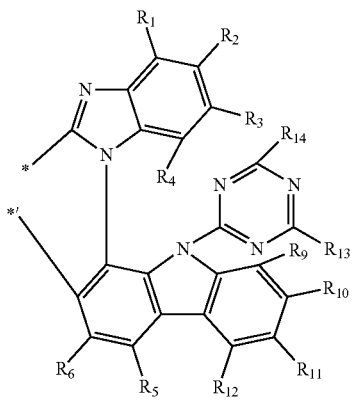
<Formula 2D>

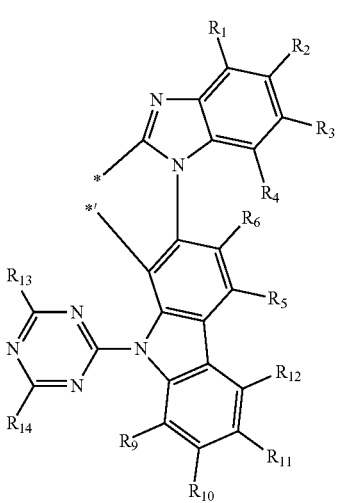
<Formula 2E>

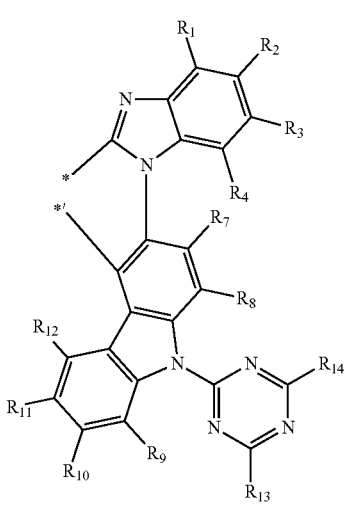
<Formula 2F> wherein, in Formulae 2A to 2F, $R_1$ to $R_{14}$, *, and *' are defined the same as $R_1$ to $R_{14}$, * and *' of Formula 2.

4. The organometallic compound of claim 1, wherein $L_1$ in Formula 1 is a ligand represented by the following Formula 3:

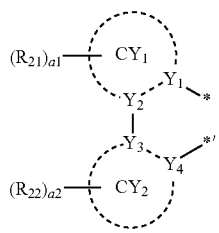
<Formula 3> wherein, in Formula 3, $Y_1$ to $Y_4$ are each independently carbon (C) or nitrogen (N);

$Y_1$ and $Y_2$ are linked to each other via a single bond or a double bond, and $Y_3$ and $Y_4$ are linked to each other via a single bond or a double bond;

$CY_1$ and $CY_2$ are each independently selected from a benzene group, a naphthalene group, a fluorene group, a spiro-fluorene group, an indene group, a pyrrol group, a thiophene group, a furan group, a imidazole group, a pyrazole group, a thiazole group, an isothiazole group, an oxazole group, an isoxazole group, a pyridine group, a pyrazine group, a pyrimidine group, a pyridazine group, a quinoline group, an isoquinoline group, a benzoquinoline group, a quinoxaline group, a quinazoline group, a carbazole group, a benzoimidazole group, a benzofuran group, a benzothiophene group, an isobenzothiophene group, a benzoxazole group, an isobenzoxazole group, a triazole group, a tetrazole group, an oxadiazole group, a triazine group, a dibenzofuran group, and a dibenzothiophene group;

$R_{21}$ and $R_{22}$ are each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, —$SF_5$, a $C_1$-$C_{20}$ alkyl group, and a $c_1$-$C_{20}$ alkoxy group;

a $C_1$-$C_{20}$ alkyl group and a $C_1$-$C_{20}$ alkoxy group, each substituted with at least one selected from a denterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a pyridinyl group, and a pyrimidinyl group;

a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, a isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, and an imidazopyrimidinyl group; and a phenyl group, a naphthyl group, a fluorenyl group, a phenanthrenyl group, an anthracenyl group, a fluoranthyenyl group, a triphenylenyl group, a pyrenyl group, a chrysenyl group, a pyrrolyl group, a thiophenyl group, a furanyl group, an imidazoly; group, a pyrazolyl group, a thiazolyl group, an isothiazolyl group, an oxazoly group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, an imidazopyrimidinyl group, and —Si($O_{41}$)($O_{42}$)($O_{43}$), each substituted with at least one selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a phenanthrenyl group, an anthracenyl group, a fluoranthenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a quinoxalinyl group, a quinazolinyl group, a cinnolinyl group, a carbazolyl group, a phenanthrolinyl group, a benzoimidazolyl group, a benzofuranyl group, a benzothiophenyl group, an isobenzothiazolyl group, a benzoxazolyl group, an isobenzoxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyridinyl group, ans an imidazopyrimidinyl group;

a1 and a2 are each independently 0, 1, 2, or 3;

$O_{41}$ to $O_{43}$ are each independently selected from a hydrogen, a $C_1$-$C_{10}$ alkyl group, a $C_1$-$C_{10}$ alkoxy group, a phenyl group, a naphtlyl group, a pyridinyl group, a pyrimidinyl group, and a triazinyl group; and

* and *' each indicate a binding site to M in Formula 1.

5. The organometallic compound as claimed in claim 4, wherein:

$CY_1$ is a benzene group, a pyridine group, a pyrimidine group, or a triazine group, $CY_2$ is a pyridine group, an imidazole group, a pyrazole group, a triazole group, or a tetrazole group;

$R_{21}$ and $R_{22}$ are each independently selected from:

a hydrogen, —F, a cyano group, a nitro group, —$SF_5$, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group; and a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group and a dibenzothiophenyl group, each substituted with at least one selected from —F, a cyano group and a nitro group; and a1 and a2 are each independently 0, 1, 2, or 3.

6. The organometallic compound as claimed in claim 1, wherein $L_1$ in Formula 1 is a ligand represented by one of the following Formulae 3-1 to 3-24:

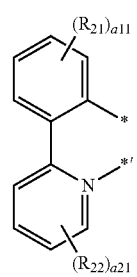

Formula 3-1

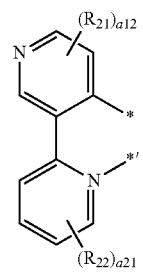

Formula 3-2

Formula 3-3

Formula 3-4

Formula 3-5

Formula 3-6

Formula 3-7

Formula 3-8

Formula 3-9

Formula 3-10

Formula 3-11

Formula 3-12

Formula 3-13

Formula 3-14

Formula 3-15 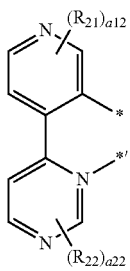
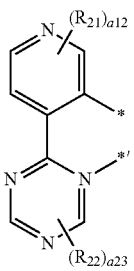

Formula 3-16 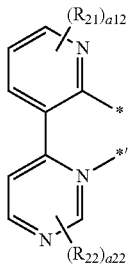
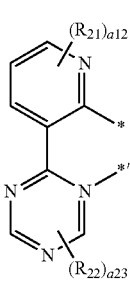 Formula 3-21

Formula 3-17 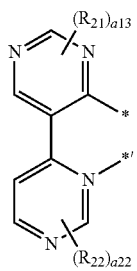
Formula 3-22 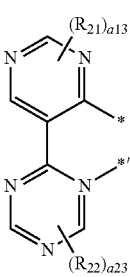

Formula 3-18 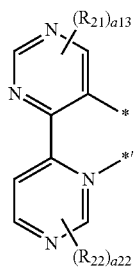
Formula 3-23 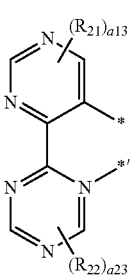

Formula 3-19 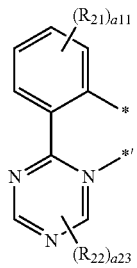

Formula 3-20 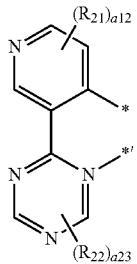

Formula 3-24 wherein, in Formulae 3-1 to 3-24,

R$_{21}$ and R$_{22}$ are each independently selected from:

a hydrogen, —F, a cyano group, a nitro group, —SF$_5$, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group, and a dibenzothiophenyl group; and a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, a triazinyl group, a dibenzofuranyl group and a dibenzothiophenyl group, each substituted with at least one selected from —F, a cyano group and a nitro group;

a11 and a21 are each independently 1, 2, 3, or 4; a12 and a22 are each independently 1, 2, or 3, a13 and a23 are each independently 1 or 2; and \* and \*' each indicate a binding site to M in Formula 1.

7. The organometallic compound as claimed in claim 1, wherein $L_1$ in Formula 1 is a ligand represented by one of the following Formulae 4-1 to 4-4:

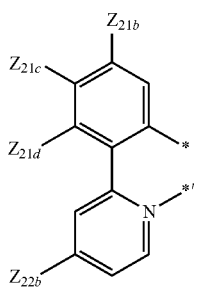

<Formula 4-1>

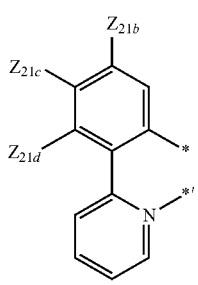

<Formula 4-2>

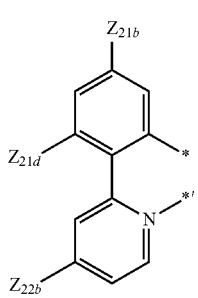

<Formula 4-3>

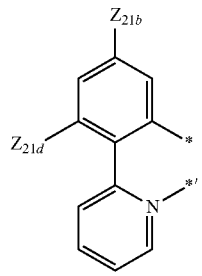

<Formula 4-4> wherein, in Formulae 4-1 to 4-4, $Z_{21b}$, $Z_{21c}$, $Z_{21d}$, and $Z_{22b}$ are each independently selected from:

—F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tort-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group;

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group, each substituted with at least one selected from —F, a cyano group, a nitro group, a phenyl group, a naphthyl group, a pyridinyl group, a pyrimidinyl group, a triazinyl group, and —Si($Q_{33}$)($Q_{34}$)($Q_{35}$); and —Si($Q_3$)($Q_4$)($Q_5$);

wherein $Q_3$ to $Q_5$ and $Q_{33}$ to $Q_{35}$ are each independently selected from a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, and an isoquinolinyl group.

8. The organometallic compound as claimed in claim 7, wherein $Z_{21b}$, $Z_{21c}$, and $Z_{21d}$ are each independently selected from —F, —Cl, —CN and —NO$_2$; and a $C_1$-$C_{20}$ alkyl group and a $C_1$-$C_{20}$ alkoxy group, each substituted with at least one selected from —F, —Cl, —CN, and —NO$_2$, and $Z_{22b}$ is selected from a $C_1$-$C_{20}$ alkyl group and —N($Q_{41}$)($Q_{42}$), wherein $Q_{41}$ and $Q_{42}$ are each independently selected from a hydrogen, a $C_1$-$C_{20}$ alkyl group, a phenyl group, a naphthyl group, and an anthracenyl group.

9. The organometallic compound as claimed in claim 1, wherein the organometallic compound represented by Formula 1 is represented by one of the following Formulae 1-1 to 1-24:

<Formula 1-1>

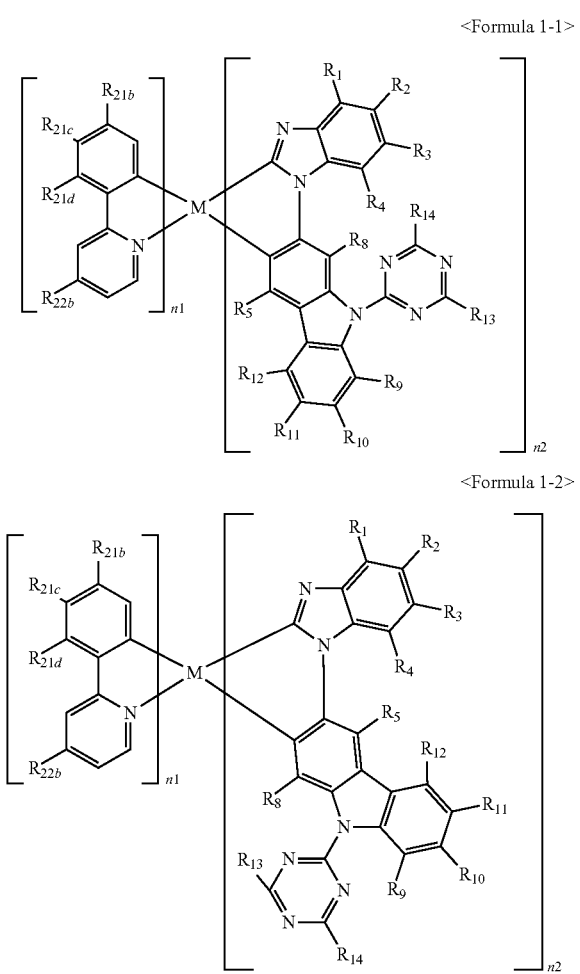

<Formula 1-2>

<Formula 1-3>

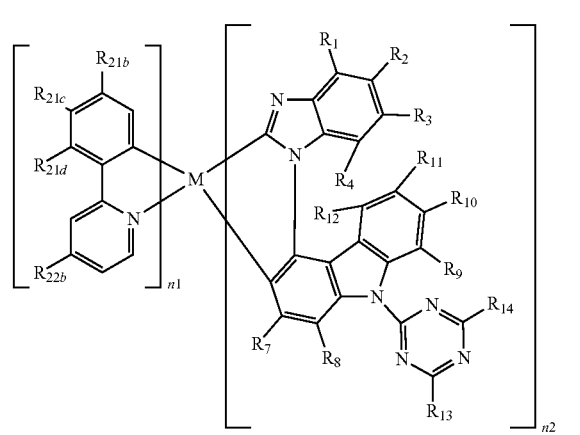

-continued

<Formula 1-4>

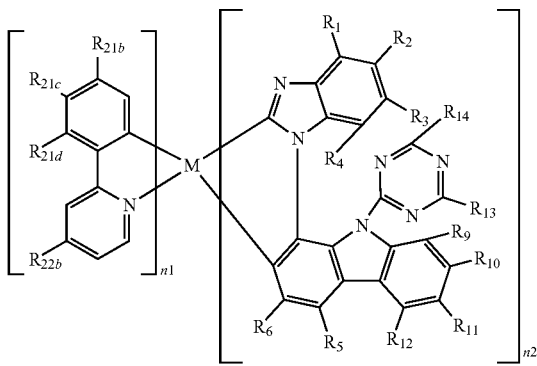

<Formula 1-5>

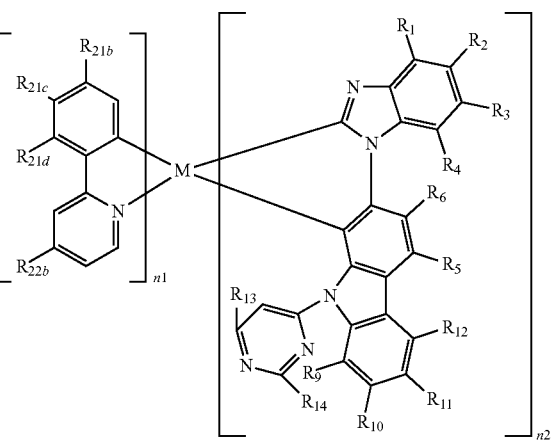

<Formula 1-6>

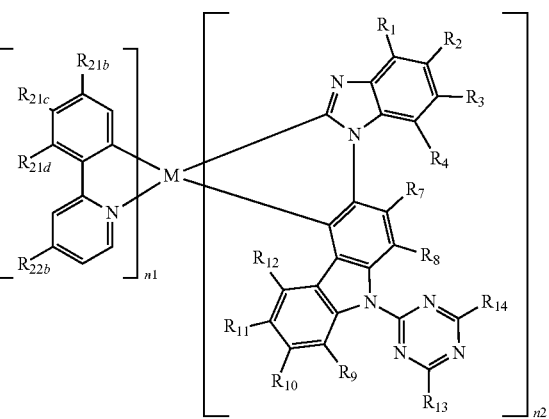

<Formula 1-7>

<Formula 1-8>

<Formula 1-9>

<Formula 1-10>

<Formula 1-11>

<Formula 1-12>

<Formula 1-13>
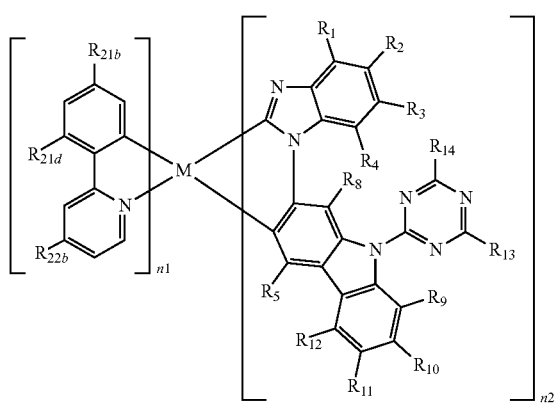
<Formula 1-14>
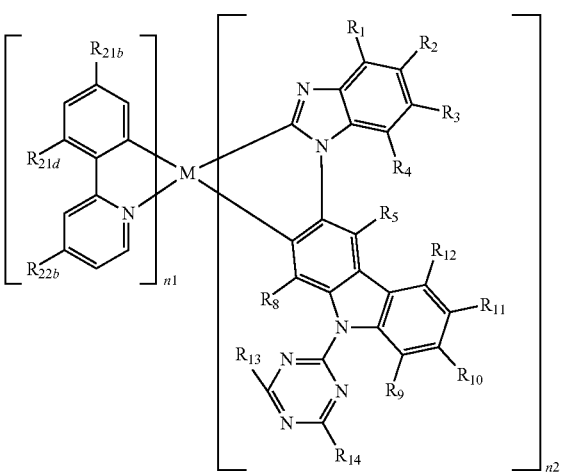
<Formula 1-15>
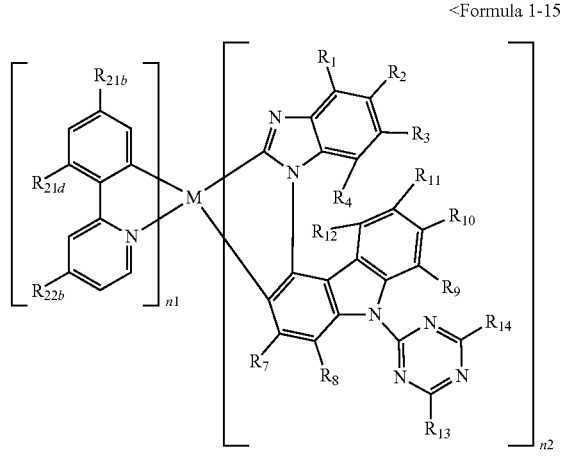
<Formula 1-16>
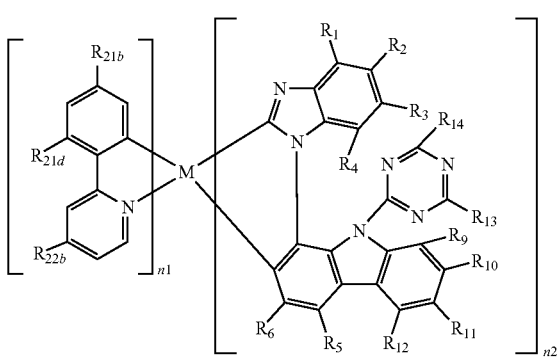
<Formula 1-17>
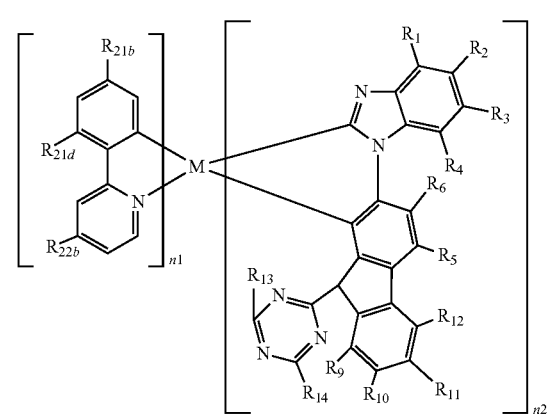
<Formula 1-18>
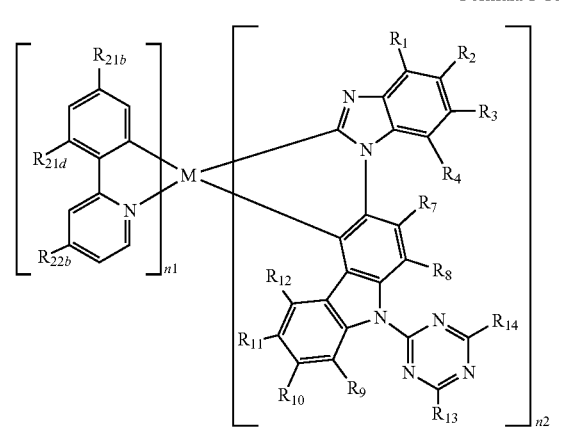

115
-continued

<Formula 1-19>
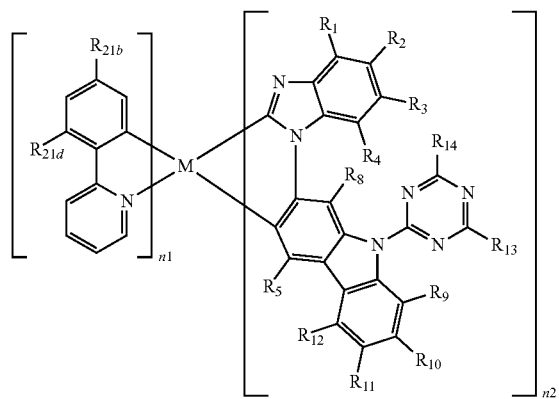

<Formula 1-20>
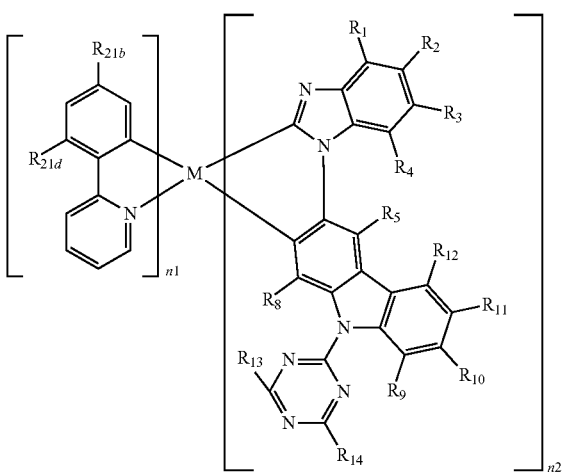

<Formula 1-21>
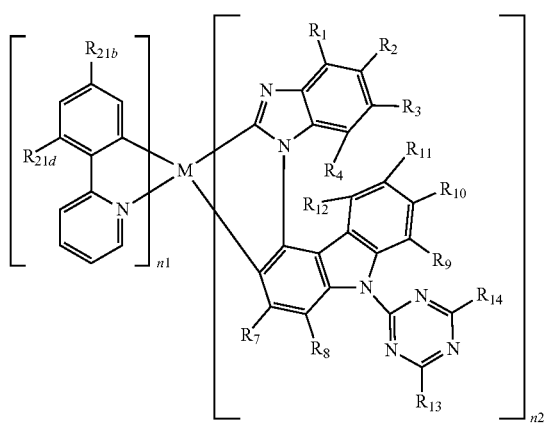

116
-continued

<Formula 1-22>
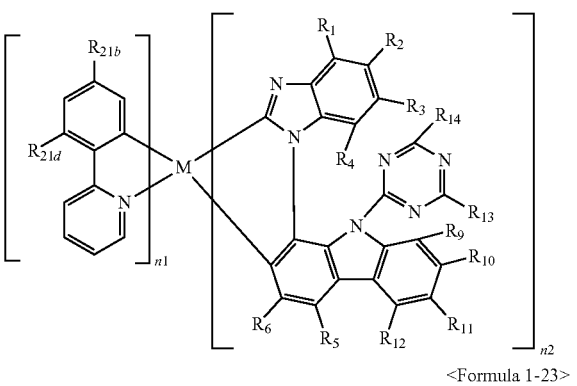

<Formula 1-23>
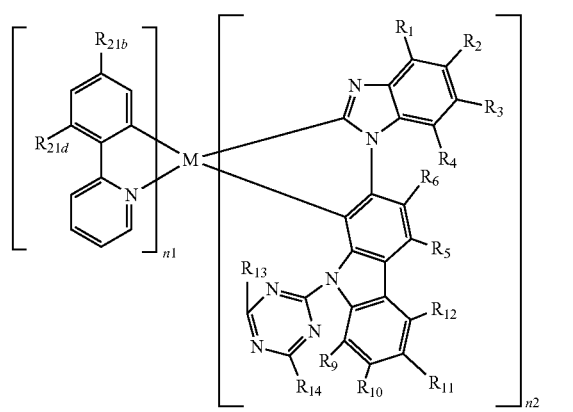

<Formula 1-24>
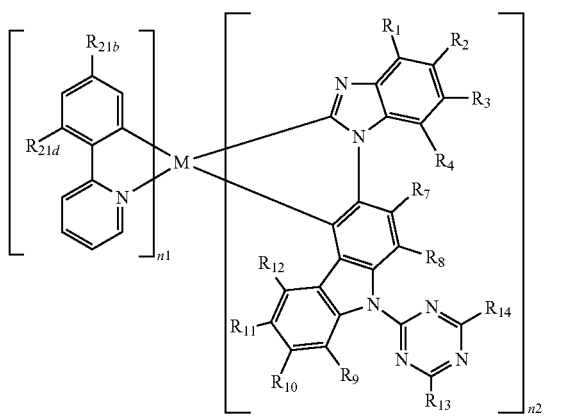

wherein, in Formulae 1-1 to 1-24,

M is iridium (Ir) or platinum (Pt);

n1 is 0, 1, or 2, n2 is 1, 2, or 3, and a sum of n1 and n2 is 2 or 3;

$R_1$ to $R_{12}$ are each independently selected from:

a hydrogen, —F, a cyano group, a nitro group, a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, and a triazinyl group;

a methyl group, an ethyl group, a propyl group, an n-butyl group, an isobutyl group, a sec-butyl group, a tert-butyl group, an n-pentyl group, an isopentyl group, a sec-pentyl group, a tert-pentyl group, an n-hexyl group, an isohexyl group, a sec-hexyl group, a tert-hexyl group, an n-heptyl group, an isoheptyl group, a sec-heptyl group, a tert-heptyl group, an n-octyl group, an isooctyl group, a sec-octyl group, a tert-octyl group, an n-nonyl group, an isononyl group, a sec-nonyl group, a tert-nonyl group, an n-decanyl group, an isodecanyl group, a sec-decanyl group, a tert-decanyl group, a methoxy group, an ethoxy group, a propoxy group, a butoxy group, a pentoxy group, a phenyl group, a naphthyl group, a pyridinyl group, a pyrimidinyl group, or a triazinyl group, each substituted with at least one selected from —F, a cyano group, a nitro group, a phenyl group, a naphthyl group, a pyridinyl group, a pyrimidinyl group, a triazinyl group, and —Si($Q_{33}$)($Q_{34}$)($Q_{35}$); and —Si($Q_3$)($Q_4$)($Q_5$), wherein $Q_3$ to $Q_5$ and $Q_{33}$ to $Q_{35}$ are each independently a hydrogen, a $C_1$-$C_{20}$ alkyl group, a $C_1$-$C_{20}$ alkoxy group, a phenyl group, a naphthyl group, a pyridinyl group, a pyrimidinyl group, a triazinyl group, a quinolinyl group, or an isoquinolinyl group;

$R_{13}$ and $R_{14}$ are each independently selected from a hydrogen or a phenyl group;

$R_{21b}$, $R_{21c}$, and $R_{21d}$ are each independently selected from —F, —Cl, —CN and —NO$_2$; and a $C_1$-$C_{20}$ alkyl group and a $C_1$-$C_{20}$ alkoxy group, each substituted with at least one selected from —F, —Cl, —CN, and —NO$_2$, $R_{22b}$ is selected from a $C_1$-$C_{20}$ alkyl group and —N($Q_{41}$)($Q_{42}$), and $Q_{41}$ and $Q_{42}$ are each independently selected from a hydrogen, a $C_1$-$C_{20}$ alkyl group, a phenyl group, a naphthyl group, and an anthracenyl group.

10. The organometallic compound as claimed in claim 1, wherein the organometallic compound represented by Formula 1 is one of the following Compounds 1 to 5, and 7 to 12, 15 to 21, and 23 to 34:

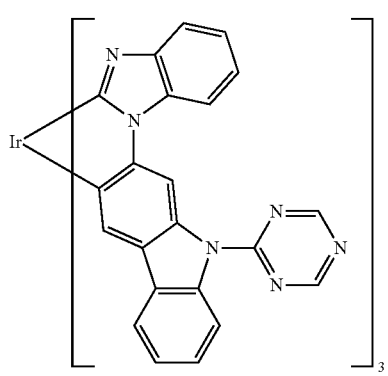

1

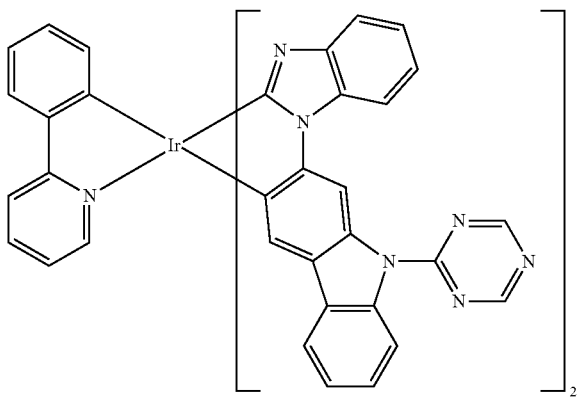

2

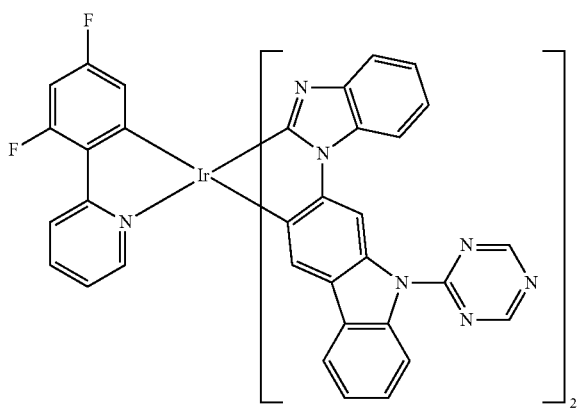

3

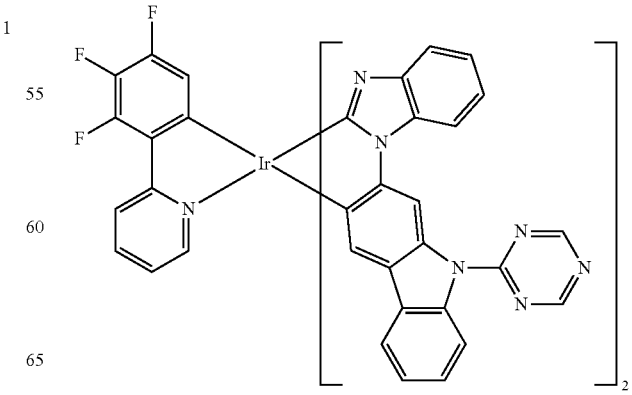

4

5
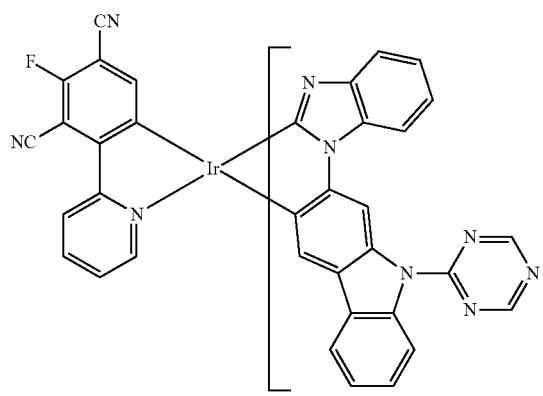
7
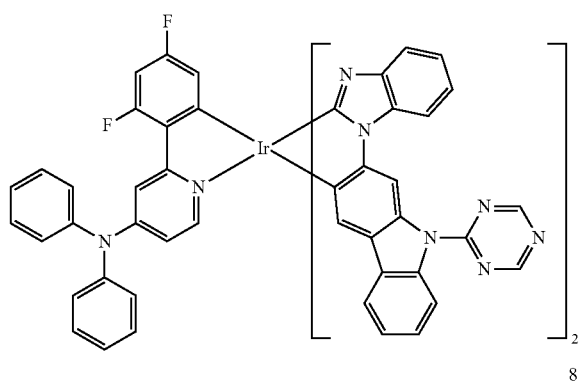
8
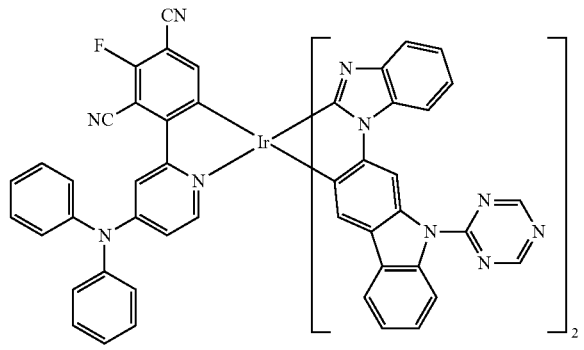
9
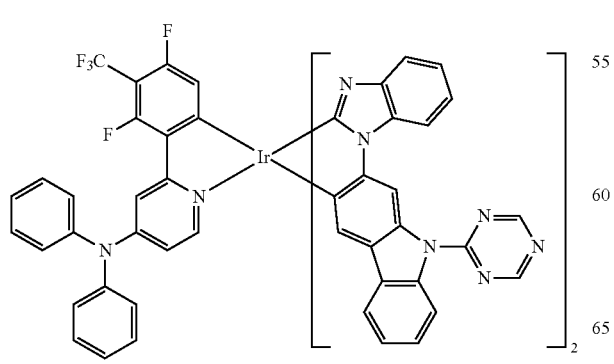
10
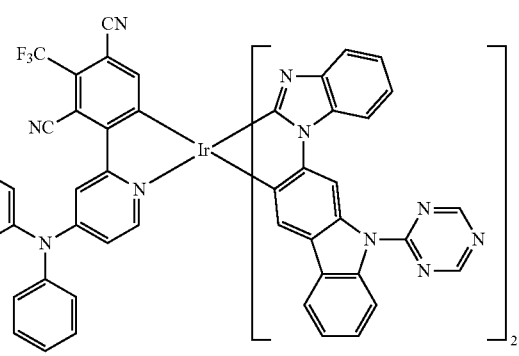
11
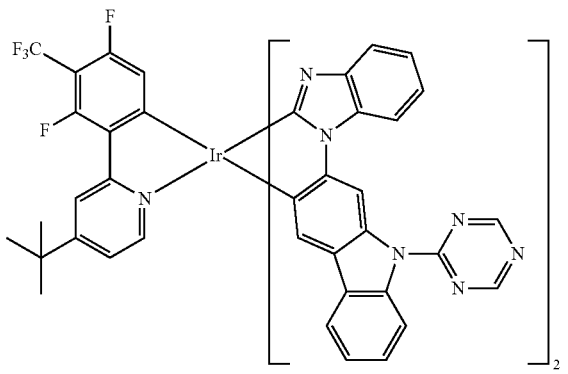
12
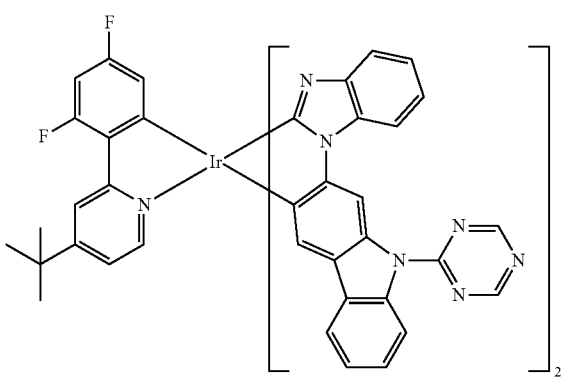
15
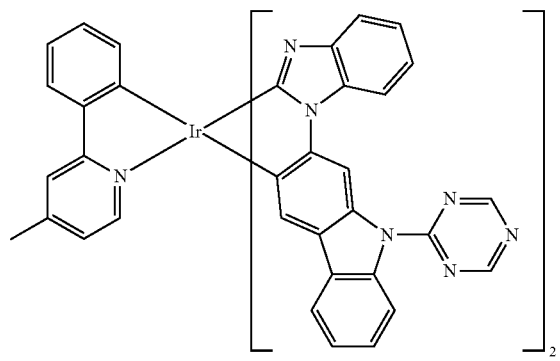

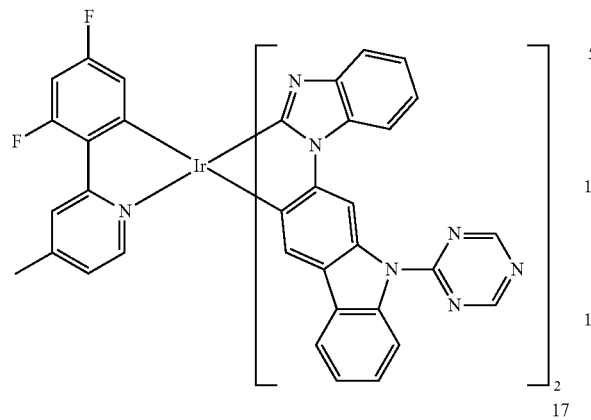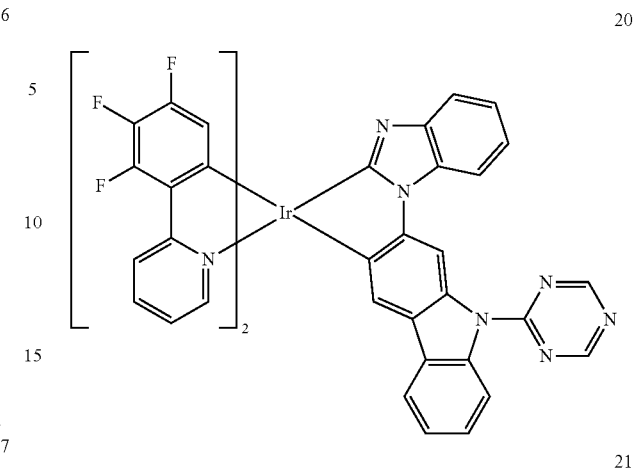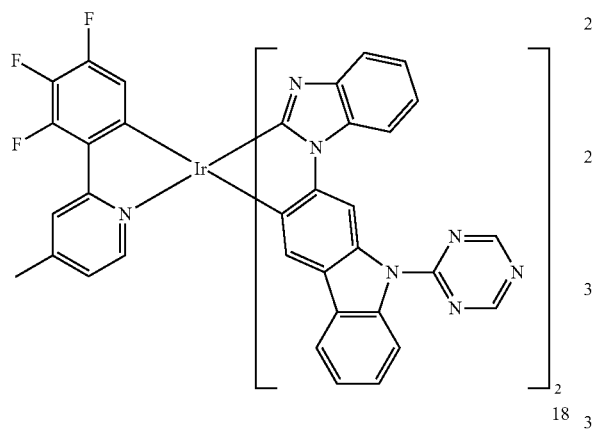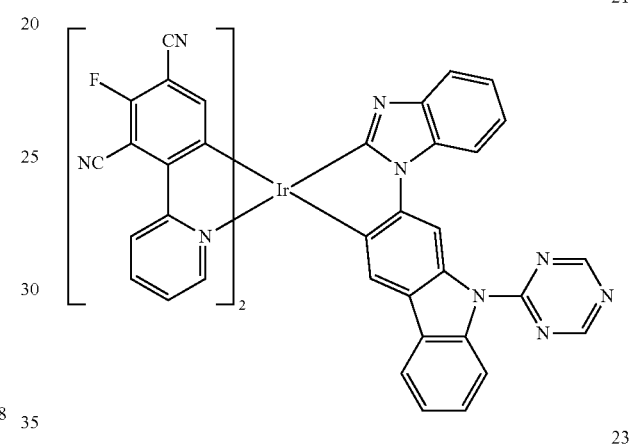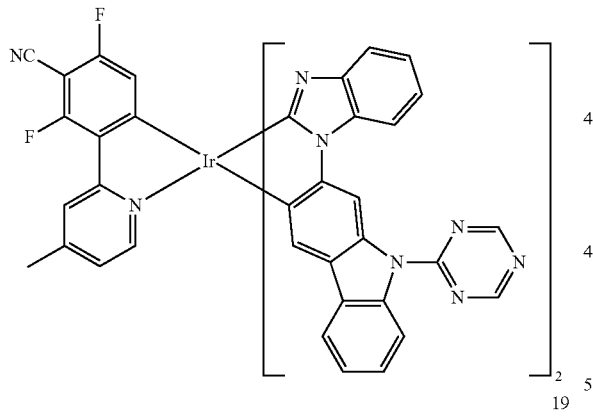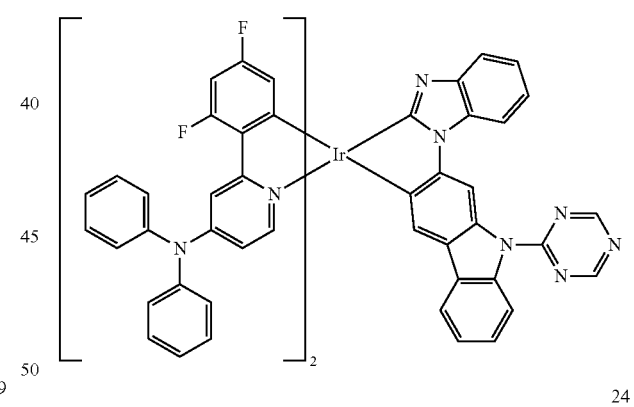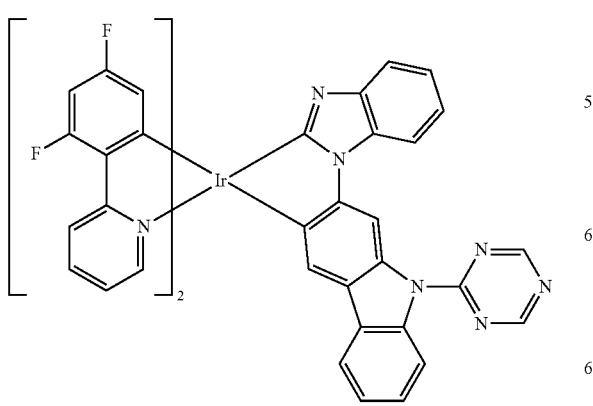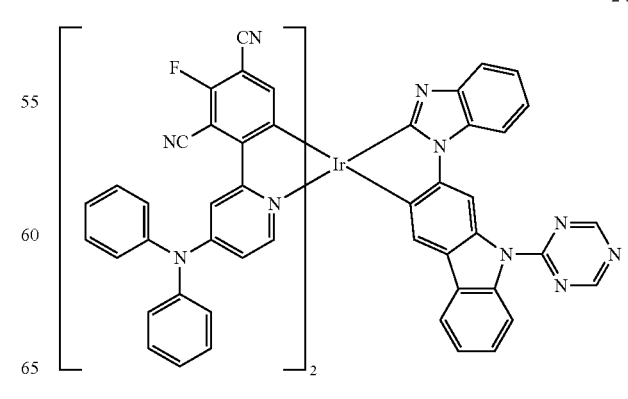

25
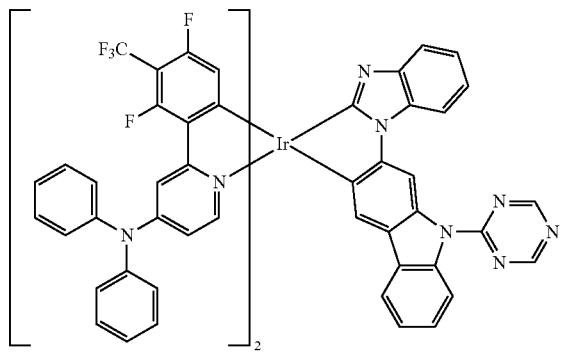
26
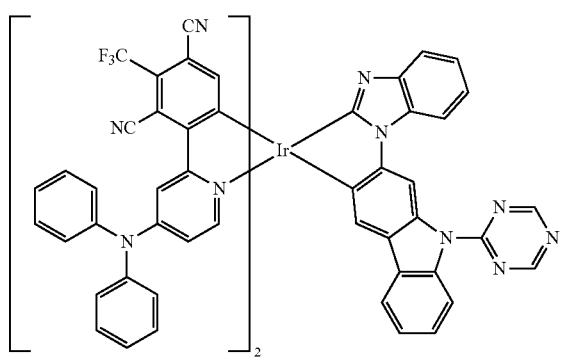
27
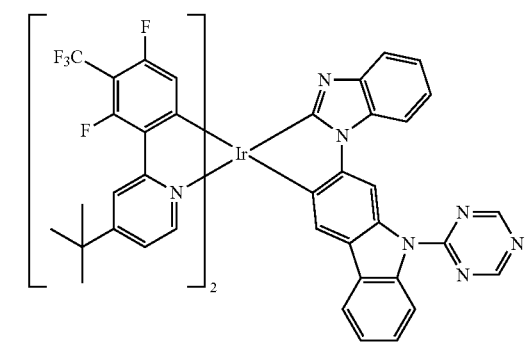
28
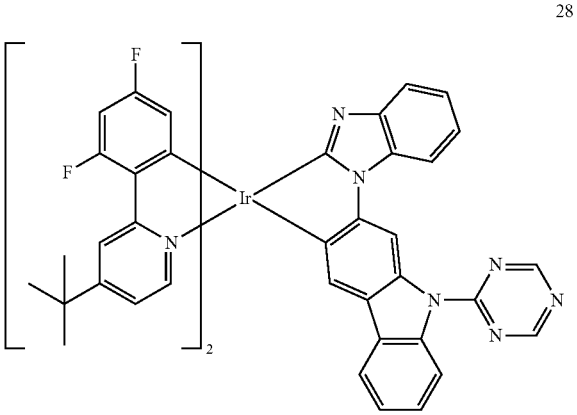
29
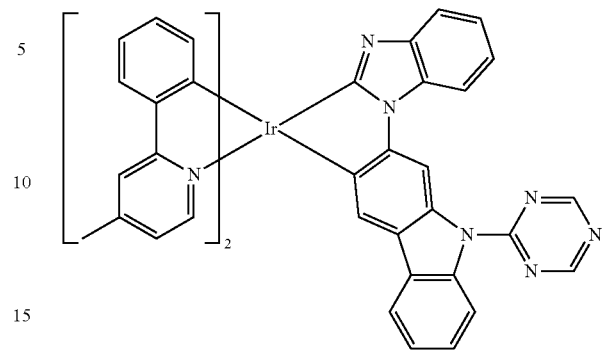
30
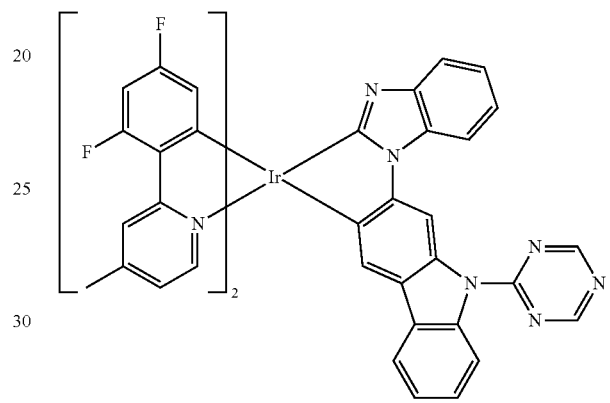
31
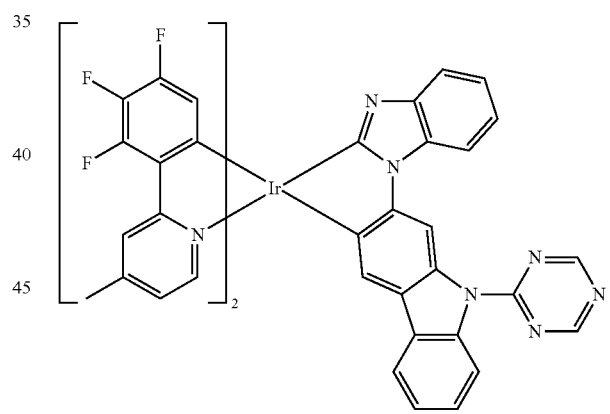
32
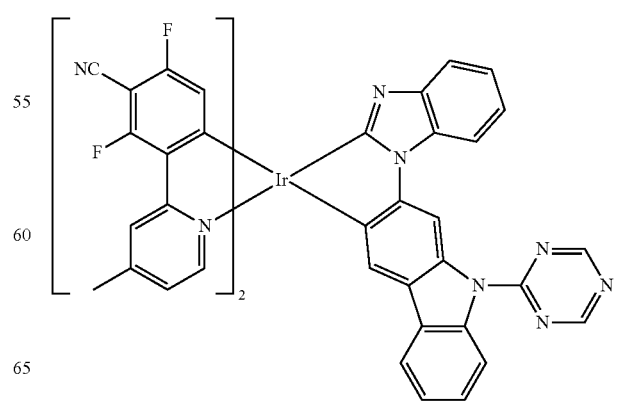

-continued

33

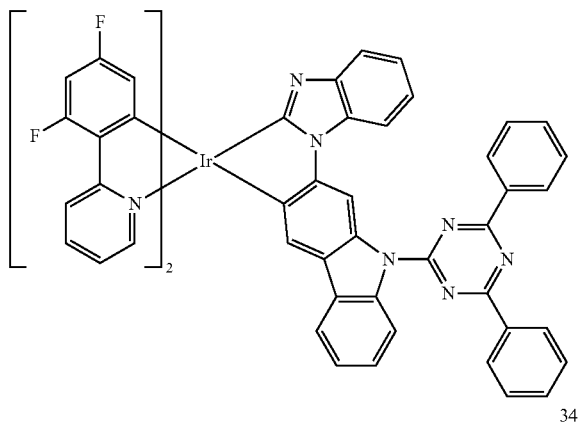

34

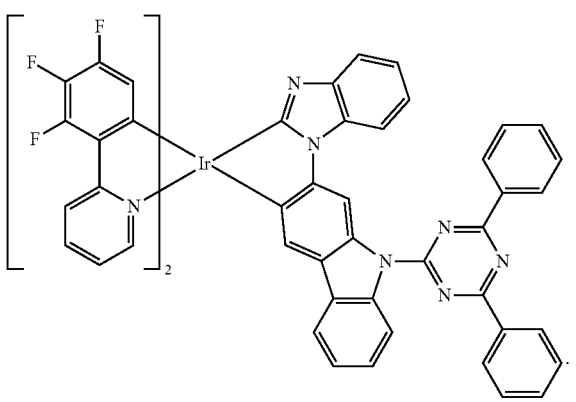

11. An organic light-emitting device, comprising:
   a first electrode;
   a second electrode facing the first electrode; and
   an organic layer between the first electrode and the second electrode, the organic layer including an emission layer,
   wherein the organic layer includes at least one organometallic compound as claimed in claim 1.

12. The organic light-emitting device as claimed in claim 11, wherein
   the first electrode is an anode,
   the second electrode is a cathode, and
   the organic layer includes:
      a hole transport region between the first electrode and the emission layer, the hole transport region including at least one of a hole injection layer, a hole transport layer, a buffer layer, and an electron blocking layer, and
      an electron transport region between the emission layer and the second electrode, the electron transport region including at least one of a hole blocking layer, an electron transport layer, and an electron injection layer.

13. The organic light-emitting device as claimed in claim 11, wherein the emission layer includes the at least one organometallic compound.

14. The organic light-emitting device as claimed in claim 13, wherein the emission layer further includes a host.

* * * * *